(12) United States Patent
Hosaka et al.

(10) Patent No.: US 10,876,160 B2
(45) Date of Patent: Dec. 29, 2020

(54) METHOD FOR DETECTING TARGET NUCLEIC ACID

(71) Applicant: Eiken Kagaku Kabushiki Kaisha, Tokyo (JP)

(72) Inventors: Norimitsu Hosaka, Tochigi (JP); Satoshi Higashide, Tochigi (JP)

(73) Assignee: Eiken Kagaku Kabushiki Kaisha, Tokyo (JP)

( * ) Notice: Subject to any disclaimer, the term of this patent is extended or adjusted under 35 U.S.C. 154(b) by 237 days.

(21) Appl. No.: 14/354,991

(22) PCT Filed: Oct. 25, 2012

(86) PCT No.: PCT/JP2012/077596
§ 371 (c)(1),
(2) Date: Aug. 13, 2014

(87) PCT Pub. No.: WO2013/065574
PCT Pub. Date: May 10, 2013

(65) Prior Publication Data
US 2014/0349295 A1   Nov. 27, 2014

(30) Foreign Application Priority Data
Oct. 31, 2011   (JP) .................................. 2011-238174

(51) Int. Cl.
*C12Q 1/6816* (2018.01)
*C12Q 1/6844* (2018.01)
*C12Q 1/6876* (2018.01)
*C12N 15/10* (2006.01)

(52) U.S. Cl.
CPC ....... *C12Q 1/6876* (2013.01); *C12N 15/1034* (2013.01); *C12Q 1/6816* (2013.01); *C12Q 2600/156* (2013.01)

(58) Field of Classification Search
CPC .................................. C12Q 1/68; C07H 21/00
See application file for complete search history.

(56) References Cited

U.S. PATENT DOCUMENTS

| | | | | |
|---|---|---|---|---|
| 4,996,143 A * | 2/1991 | Heller | .................. | C12Q 1/6818 435/6.12 |
| 6,670,467 B2 * | 12/2003 | Barbour | ............... | C07K 14/415 435/252.3 |
| 7,919,252 B2 * | 4/2011 | Nakamura | ........... | C12Q 1/6813 435/6.12 |
| 2003/0096254 A1 * | 5/2003 | Reed | ..................... | C07C 245/08 435/6.12 |
| 2004/0076974 A1 * | 4/2004 | Kier | ..................... | C12Q 1/6883 435/6.11 |
| 2004/0086879 A1 * | 5/2004 | Li | ........................ | C12Q 1/6818 435/6.11 |
| 2005/0260619 A1 * | 11/2005 | Brousseau | ............. | C12Q 1/689 435/6.18 |
| 2006/0115838 A1 * | 6/2006 | Bazar | .................. | C12Q 1/6823 435/6.16 |
| 2006/0240462 A1 * | 10/2006 | Todd | .................... | C12Q 1/6816 435/6.16 |
| 2007/0031857 A1 * | 2/2007 | Makarov | ................. | C12P 19/34 435/6.18 |
| 2008/0228406 A1 * | 9/2008 | Denning | ............. | G01N 33/569 702/19 |
| 2009/0042197 A1 * | 2/2009 | Hayashizaki | ........ | C12Q 1/6844 435/6.12 |
| 2012/0276538 A1 * | 11/2012 | Nadeau | ................ | C12Q 1/6865 435/6.11 |
| 2014/0342933 A1 * | 11/2014 | Reitmair | .............. | C12Q 1/6825 506/9 |

FOREIGN PATENT DOCUMENTS

| | | |
|---|---|---|
| CN | 1348096 A | 5/2002 |
| JP | S61-274697 | 12/1986 |
| JP | H2-002934 | 1/1990 |
| JP | H2-005864 | 1/1990 |
| JP | 5-192195 | 8/1993 |
| JP | 1994-500021 | 1/1994 |
| JP | H10-262700 | 10/1998 |
| JP | S62-000281 | 7/1999 |
| JP | 2001-272475 | 10/2001 |
| JP | 2001-286300 | 10/2001 |
| JP | 2001-521622 | 11/2001 |
| JP | 3313358 | 8/2002 |
| JP | 2004-511227 | 4/2004 |
| JP | 2004-283161 | 10/2004 |
| TW | 1221855 | 10/2004 |
| WO | 1997/01755 A | 1/1997 |
| WO | WO 97/29210 | 8/1997 |
| WO | 1998/45481 | 10/1998 |
| WO | 2002/024902 | 3/2002 |
| WO | WO 2002/030946 | 4/2002 |
| WO | 2009/051214 | 4/2009 |
| WO | WO 2011/163425 | 12/2011 |
| WO | 2012/014778 | 2/2012 |

OTHER PUBLICATIONS

Amagliani et al., Development of a magnetic capture hybridization-PCR assay for Listeria monocytogenes direct detection in milk samples. J. of Applied Microbiology 100 : 375 (2006).*

(Continued)

*Primary Examiner* — Bradley L. Sisson
(74) *Attorney, Agent, or Firm* — Fish & Richardson P.C.

(57) ABSTRACT

The purpose of the present invention is to provide: a novel method for detecting a target nucleic acid; and a kit for use in the method. In the detection method according to the present invention, a fluorophore-labeled primer/probe and a quencher-labeled probe, which have complementarity to each other, are so designed as to have different melting temperatures (Tm) from each other so that the fluorophore-labeled primer can anneal preferentially to the target nucleic acid. The detection method is so designed that the fluorophore-labeled primer/probe that is not bound to the target nucleic acid is bound to the quenching probe so as to emit no fluorescence. The method enables the detection of the target nucleic acid in a simpler manner, at lower cost, and without requiring the use of any technique or device.

12 Claims, 15 Drawing Sheets

Specification includes a Sequence Listing.

(56) References Cited

OTHER PUBLICATIONS

Curtis et al., Rapid detection of HIV-1 by reverse-transcription, loop-mediated isothermal amplification (RT-LAMP). J. of Virological Methods 151 :264 (2008).*
Dunbar et al., Applications of LuminexR xMAPi technology for rapid, high-throughput multiplexed nucleic acid detection. Clinica Chemica Acta 363 : 71 (2006).*
Kennedy et al., Locked nucleic acids for optimizing displacement probes for quantitative real-time PCR. Analytical Biochemistry 348 : 294(2006).*
Tyagi et al., Multicolor molecular beacons for allele discrimination. Nature Biotechnology 16: 49 (1998).*
Uemura et al., Development of a loop-mediated isothermal amplification method for diagnosing Pneumocystis pneumonia. J. Medical Microbiology 57 : 50 (2008).*
Holland et al., Detection of specific polymerase chain reaction product by utilizing the 5'----3'exonuclease activity of Thermus aquaticus DNA polymerase. PNAS 88 :7276 (1991).*
Little et al., Strand Displacement Amplification and Homogeneous Real-Time Detection Incorporated in a Second-Generation DNA Probe System,BDProbe T ecET. Clinical Chemistry 88 :7276 (1991).*
Marras et al., Multiplex detection of single-nucleotide variations using molecular beacons. Genetic Analysis :Biomolecular Engineering 14 : 151 (1999).*
Walker et al., Strand displacement amplification—an isothermal, in vitro DNA amplification technique. Nucleic Acids Research 20 (7) : 1691 (1992).*
Braasch et al., Locked nucleic acid (LNA): fine-tuning the recognition of DNA and RNA. Chemistry & Biology 8 :1-7 (Year: 2001).*
Levin, R.E. The Application of Real-Time PCR to Food and Agricultural Systems. A Review. Food Biotechnology 18(1) :97-133 (Year: 2004).*
Tyagi et al., Multicolor molecular beacons for allele discrimination. Nature Biotechnology 16 : 49 (Year: 1998).*
Walker et al., Isothermal in vitro amplification of DNA by a restriction enzyme/DNA polymerase system. PNAS 89 : 392 (Year: 1992).*
Li et al., A new class of homogeneous nucleic acid probes based on specific displacement hybridization. Nucleic Acids Research 30(2) : e5 (Year: 2002).*
Zhang et al., Optimizing the specificity of nucleic acid hybridization. Nature Chemistry 4: 208 (Jan. 2012).*
Li et al., "A new class of homogeneous nucleic acid probes based on specific displacement hybridization". Nucleic Acids Research, vol. 30, No. 2, e5. (Year: 2002).*
Mitani et al., Rapid SNP diagnostics using asymmetric isothermal amplification and a new mismatch suppression technology. Nature Methods 4(3) :257. (Year: 2007).*
Tyagi et al., "Multicolor molecular beacons for allele discrimination", Nature Biotechnology, vol. 16, Jan. 1998, pp. 49-53. (Year: 1998).*
Luk et al., "Partially double-stranded linear DNA probes: Novel design for sensitive detection of genetically polymorphic targets", Journal of Virological Methods, vol. 144, Issues 1-2, Sep. 2007, pp. 1-11. (Year: 2007).*
Office Action issued in corresponding Chinese Application No. CN201280058995.6, dated Aug. 21, 2015, 15 pages.
Curtis et al., "Sequence-Specific Detection Method for Reverse Transcription, Loop-Mediated Isothermal Amplification of HIV-1", Journal of Medical Virology 81: 966-972 (2009).
Fire and Xu, "Rolling replication of short DNA Circles", Proceedings of the National Academy of Sciences of the United States of America 92: 4641-4645 (1995).
International Preliminary Report for PCT/JP2012/077596 dated May 6, 2014.
Kennedy et al., "Locked nucleic acids for optimizing displacement probes for quantitative real-time PCR", Analytical Biochemistry 348(2): 294-299 (2006).
Luk et al., "Partially double-stranded linear DNA probes: Novel design for sensitive detection of genetically polymorphic targets", J,Virol. Methods 144(1-2): 1-11 (2007).
Mitani et al., "Rapid SNP diagnostics using asymmetric isothermal amplification and a new mismatch-suppression technology", Nature Methods 4: 257-262 (2007).
Re-issued Extended European Search Report in corresponding European Application No. 12845733.0, dated Dec. 7, 2015, 9 pages.
Office Action issued in Taiwanese Application No. 101140141, dated May 10, 2016, 5 pages.
Baar et al., "One-Tube Real-Time Isothermal Amplification Assay to Identify and Distinguish Human Immunodeficiency Virus Type 1 Subtypes A, B, and C and Circulating Recombinant Forms AE AG", Journal of Clinical Microbiology, May 2001, May 2001, 39(5):1895-1902.
Doseeva et al., "Multiplex isothermal helicase-dependent amplification assay for detection of *Chlamydia trachomatis* and *Neisseria gonorrhoeae*", Diagnostics Microbiology and Infectious Disease, Dec. 2011 71(4):354-65.
Extended European Search Report for EP Application No. 12845733.0 dated Jun. 3, 2015.
Li et al., "A new class of homogeneous nucleic acid probes based on specific displacement hybridization", Nucleic Acid Research, vol. 30, e5, pp. 1-9 (2002).
Office Action for corresponding CN Application No. 201280058995.6 dated Dec. 25, 2014.

* cited by examiner

METHOD FOR DETECTING TARGET NUCLEIC ACID

TECHNICAL FIELD

The present invention relates to a method for detecting a target nucleic acid and a kit for use in the detection.

BACKGROUND ART

Methods for detecting a target nucleic acid using the complementarity of nucleic acid sequences have been improved or modified variously from traditional Southern hybridization up to the present date. Particularly, the establishment of in vitro nucleic acid amplification methods has enabled much smaller amounts of the target nucleic acid to be detected.

Detection methods using label (e.g., radioisotope (RI), luminescent agent, or fluorophore)-bounded probes comprising nucleic acids having complementarity to target nucleic acids have been developed as methods for detecting target nucleic acids. Multiple-item detection can be achieved by labeling with a plurality of RIs differing in released energy or by labeling with a plurality of luminescent agents (or fluorophores) differing in the wavelength of emitted light. In addition, methods for determining single nucleotide polymorphisms (SNPs) have also been established as quenching probe (Q probe) methods (Patent Literature 1).

On the other hand, methods for detecting target nucleic acids using the complementarity of nucleic acid sequences, such as so-called DNA chips or microarrays, which have enabled the amounts of a plurality of target nucleic acids to be detected, have also been practiced by labeling target nucleic acids with radioisotopes or the like and annealing the labeled target nucleic acids to oligonucleotide probes (having complementarity to the target nucleic acid) immobilized on a solid-phase surface (Patent Literature 2).

Examples of the nucleic acid amplification methods include polymerase chain reaction (PCR) (Patent Literatures 3 and 4), strand displacement amplification (SDA) (Patent Literature 5), nucleic acid sequence-based amplification (NASBA) (Patent Literature 6), rolling circle amplification (RCA) (Non Patent Literature 1), and loop-mediated isothermal amplification (LAMP) (Patent Literature 7). These nucleic acid amplification methods also provide for detection of target nucleic acids.

There exists another nucleic acid amplification method using ligase, such as ligase chain reaction (LCR) (Patent Literature 8).

At the moment, PCR is frequently used as a nucleic acid amplification method. The PCR method amplifies target nucleic acids in an exponential fashion by using thermostable polymerase and two primers having complementarity to each target nucleic acid and repetitively performing three steps with temperatures controlled: (1) denaturation of double-stranded target nucleic acids, (2) annealing of the primers to the denatured target nucleic acids, and (3) extension reaction from the primers. After the reaction, amplification products are electrophoresed, and the presence or absence of the amplification product of interest can be detected by use of an intercalator such as ethidium bromide (EtBr) or SYBR® Green. In another method, the amplification product is detected by use of fluorophore-attached nucleobases in the extension reaction.

Alternative established methods involve quantitatively detecting the amplification of target nucleic acids by use of a fluorophore and a quencher (Patent Literature 9). Specifically, an oligonucleotide probe typified by TaqMan® probe, to which a fluorophore and a quencher are adjacently attached, is added for PCR amplification reaction to perform PCR reaction. In the step (2) of PCR, the probe is also annealed to the target nucleic acid. Along with the extension reaction of the step (3), the probe is degraded by the 5'→3' exonuclease activity of polymerase. The emitted light of the fluorophore liberated from the quencher can be detected to thereby detect the target nucleic acid.

Various nucleic acid detection methods using such a combination of a fluorophore and a quencher have been formulated on the premise of PCR amplification (Patent Literatures 10 and 11). In both of these methods, a fluorophore is attached to one of complementary oligonucleotide probes, and a quencher is attached to the other probe. These methods have been formulated for the purpose of detecting target nucleic acids during amplification in the annealing step (the step (2)) of PCR.

The feature of the LAMP method is that 4 primers (FIP, BIP, F3, and B3) are designed for 6 regions in each target nucleic acid, which is in turn amplified at a constant temperature through the use of strand displacement reaction. A sample containing target nucleic acids, the primers, strand displacement-type DNA synthetase, a substrate, and the like are mixed and incubated at a constant temperature (around 65° C.) to promote reaction. In this method, the process to detection can be performed in one step. Additional use of a loop primer B (LB) and/or a loop primer F (LF) can shorten the time required for amplification by ½ to ⅓ (Patent Literature 12). Because of high amplification efficiency, target nucleic acids can be amplified $10^9$- to $10^{10}$-fold in 15 minutes to 1 hour. In addition, because of very high specificity, the presence or absence of the target gene sequence of interest can be determined on the basis of the presence or absence of amplification products. One of such methods detects the presence of amplification products by converting a pyrophosphate ion obtained as a by-product of nucleic acid amplification reaction into an insoluble salt (magnesium salt) and measuring the turbidity of the reaction solution or by reacting the pyrophosphate ion with a calcein-manganese complex and detecting the fluorescence of liberated calcein (fluorescent material) (Patent Literature 13). Detection methods using fluorescent probes have been further established (Patent Literatures 14 and 15).

There has also been reported a method for detecting amplified target nucleic acids by the LAMP method using fluorophore-labeled primers and quencher-labeled probes (Non Patent Literature 2). Specifically, target nucleic acids are amplified by the LAMP method using fluorophore-labeled primers. After the amplification, quencher-labeled probes are added thereto to anneal the quencher-labeled probes to free fluorophore-labeled primers that have not contributed to the amplification of the target nucleic acid. In this method, only the emitted light of fluorophores in the fluorophore-labeled primers that have contributed to the amplification of the target nucleic acid, i.e. have become a part of amplification products, is detected.

Any of the above nucleic acid detection methods have their respective advantages and disadvantages. These methods require expensive sensitive equipment, particularly, for reaction or detection, and further involve various steps. Skills are therefore required for carrying out the methods. These nucleic acid detection techniques have been practiced mainly in specific laboratories dedicated to nucleic acid amplification. For example, the detection method described in Non Patent Literature 2 has the risk of causing the contamination between samples or of experimental environments due to the release of amplification products at the time of opening and closing of the lid of a reaction container, because quenchers need to be added after amplification reaction.

In recent years, there have been growing demands for nucleic acid amplification tests (NATs) in various fields including industry, medicine, and research, while the types of test items have been expanded. Accordingly, the nucleic acid amplification tests have been being more widespread than ever. The nucleic acid amplification tests are also used in, for example, tests conducted with the aim of securing the safety of blood products against various viruses in the pharmaceutical field. Owing to the tide of such proliferation or universalization, there have been demands for conveniently usable nucleic acid detection techniques without contaminating test environments, and by extension, techniques capable of multiple-item simultaneous detection such that the nucleic acid amplification tests, which have previously been practiced only in specific laboratories dedicated to nucleic acid amplification, can be conducted at every site or situation such as general laboratories, field works, or bedside.

CITATION LIST

Patent Literature
Patent Literature 1: JP 2001-286300 A
Patent Literature 2: JP 2001-521622 A
Patent Literature 3: JP 61-274697 A
Patent Literature 4: JP 62-000281 A
Patent Literature 5: JP 5-192195 A
Patent Literature 6: JP 2-005864 A
Patent Literature 7: Japanese Patent No. 3313358
Patent Literature 8: JP 2-002934 A
Patent Literature 9: JP 1994-500021 A
Patent Literature 10: JP 10-262700 A
Patent Literature 11: JP 2004-511227 A
Patent Literature 12: International Publication No. WO 2002/024902
Patent Literature 13: JP 2004-283161 A
Patent Literature 14: JP 2001-272475 A
Patent Literature 15: International Publication No. WO 2009/051214
Non Patent Literature
Non Patent Literature 1: Proceedings of the National Academy of Sciences of the United States of America 92: 4641-4645 (1995)
Non Patent Literature 2: Journal of Medical Virology 81: 966-972 (2009)

SUMMARY OF INVENTION

Technical Problem

An object of the present invention is to provide a novel method for detecting target nucleic acids. More specifically, an object of the present invention is to provide a method for detecting target nucleic acids more conveniently and inexpensively than conventional techniques, and a kit or the like for use in the detection.

Solution to Problem

To attain the object, the present inventors have newly developed a method capable of easy nucleic acid amplification and detection in a closed system. Specifically, the present inventors have intended to enable fluorophore-labeled primers and quencher-labeled probes to be added before amplification reaction in methods for detecting target nucleic acids amplified by the LAMP method using the fluorophore-labeled primers and the quencher-labeled probe. For this purpose, the fluorophore-labeled primers and the quencher-labeled probes are designed to differ in melting temperature (hereinafter, referred to as Tm) therebetween. This facilitates the annealing of the fluorophore-labeled primers to the target nucleic acid under conditions at a reaction temperature even in the presence of the quencher-labeled probes. As the temperature is then decreased, fluorophore-labeled primers that have failed to bind to the target nucleic acid can be annealed to the quencher-labeled probes. As a result, it has been found that these fluorescent labels are quenched by the quenchers, whereas only the fluorescent labels in the fluorophore-labeled primers successfully bound with the target nucleic acid can be detected.

The present inventors have further found that this method can be combined not only with the LAMP amplification but with any other nucleic acid amplification method and can be carried out without involving a target nucleic acid amplification step, i.e., even by using fluorophore-labeled primers as mere probes. Thus, the objects of the present invention can be attained, and the present invention has been completed on the basis of these findings.

Specifically, the present invention is constituted as described below in [1] to [13].

[1]
A method for detecting one or more target nucleic acids present in a sample, comprising the following steps:
(1) adding, to the sample,
a fluorophore-labeled primer or probe, wherein the fluorophore-labeled primer or probe is a fluorophore-labeled oligonucleotide having complementarity to each target nucleic acid, and
a quencher-labeled probe, wherein the quencher-labeled probe is a quencher-labeled oligonucleotide having complementarity to the fluorophore-labeled primer or probe and having a melting temperature (Tm) lower than that of the fluorophore-labeled primer or probe;
(2) incubating the sample at a temperature equal to or lower than the melting temperature (Tm) of the fluorophore-labeled primer or probe and higher than the melting temperature (Tm) of the quencher-labeled probe;
(3) incubating the sample at a temperature equal to or lower than the melting temperature (Tm) of the quencher-labeled probe; and
(4) measuring fluorescence of the fluorophore-labeled primer or probe bound with the target nucleic acid.

[2]
The detection method according to [1], wherein the target nucleic acid is amplified during the incubation of the step (2).

[3]
The detection method according to [2], wherein the amplification of the target nucleic acid is performed under isothermal conditions.

[4]
The detection method according to any of [1] to [3], wherein the oligonucleotide of the quencher-labeled probe has a base length shorter than that of the oligonucleotide of the fluorophore-labeled primer or probe.

[5]
The detection method according to any of [1] to [3], wherein the oligonucleotide of the quencher-labeled probe comprises a modified base.

[6]
The detection method according to any of [1] to [5], wherein the fluorophore-labeled primer or probe is immobilized on a solid-phase surface for use.

[7]
The method according to any of [1] to [6], wherein a combination of two or more fluorophore-labeled primers or probes differing in emission wavelength and quencher-labeled probes respectively compatible therewith is used for detecting two or more target nucleic acids.

[8]
The method according to any of [1] to [7], wherein the measurement of the fluorescence in the step (4) is visual determination.

[9]
The method according to any of [1] to [7], wherein the measurement of the fluorescence in the step (4) is determination using a fluorescence detector.

[10]
A kit for use in a detection method according to any of [1] to [9], comprising one or more combinations each comprising:
a fluorophore-labeled primer or probe, wherein the fluorophore-labeled primer or probe is a fluorophore-labeled oligonucleotide having complementarity to each target nucleic acid, and
a quencher-labeled probe, wherein the quencher-labeled probe is a quencher-labeled oligonucleotide having complementarity to the fluorophore-labeled primer or probe and having a melting temperature (Tm) lower than that of the fluorophore-labeled primer or probe, wherein the quencher is compatible with the fluorophore.

[11]
The kit for target nucleic acid detection according to [10], wherein the oligonucleotide of the quencher-labeled probe has a base length shorter than that of the oligonucleotide of the fluorophore-labeled primer or probe.

[12]
The kit for target nucleic acid detection according to [10], wherein the oligonucleotide of the quencher-labeled probe comprises a modified base.

[13]
The kit according to any of [10] to [12], wherein the kit further comprises a reagent for nucleic acid amplification.

[14]
The kit for target nucleic acid detection according to any of [10] to [13], wherein the fluorophore-labeled primer or probe is immobilized on a solid-phase surface.

Advantageous Effects of Invention

According to the method of Non Patent Literature 2, amplification reaction does not take place normally, if fluorophore-labeled primers and quencher-labeled probes are added before amplification reaction. In this case, target nucleic acids are difficult to detect. In the present invention, however, fluorophore-labeled primers or probes (hereinafter, referred to as fluorophore-labeled primers/probes) and quencher-labeled probes are allowed to have distinct melting temperatures (Tm). The resulting fluorophore-labeled primers can be annealed preferentially to target nucleic acids even in the presence of the quencher-labeled probes.

Such an advantage of the present invention is effectively exerted not only on the method of Non Patent Literature 2 involving an amplification step but on other aspects free from the amplification step.

The method of the present invention eliminates the need of adding quencher-labeled probes after amplification reaction and is therefore in no danger of the contamination between samples or of experimental environments due to the release of amplification products. Furthermore, the method of the present invention does not involve a washing step or the like and makes temperature control relatively convenient and free from necessary precision and can therefore detect target nucleic acids more conveniently and inexpensively without the need of special skills or equipment, compared with conventional hybridization methods.

DESCRIPTION OF EMBODIMENTS

Figure 1:
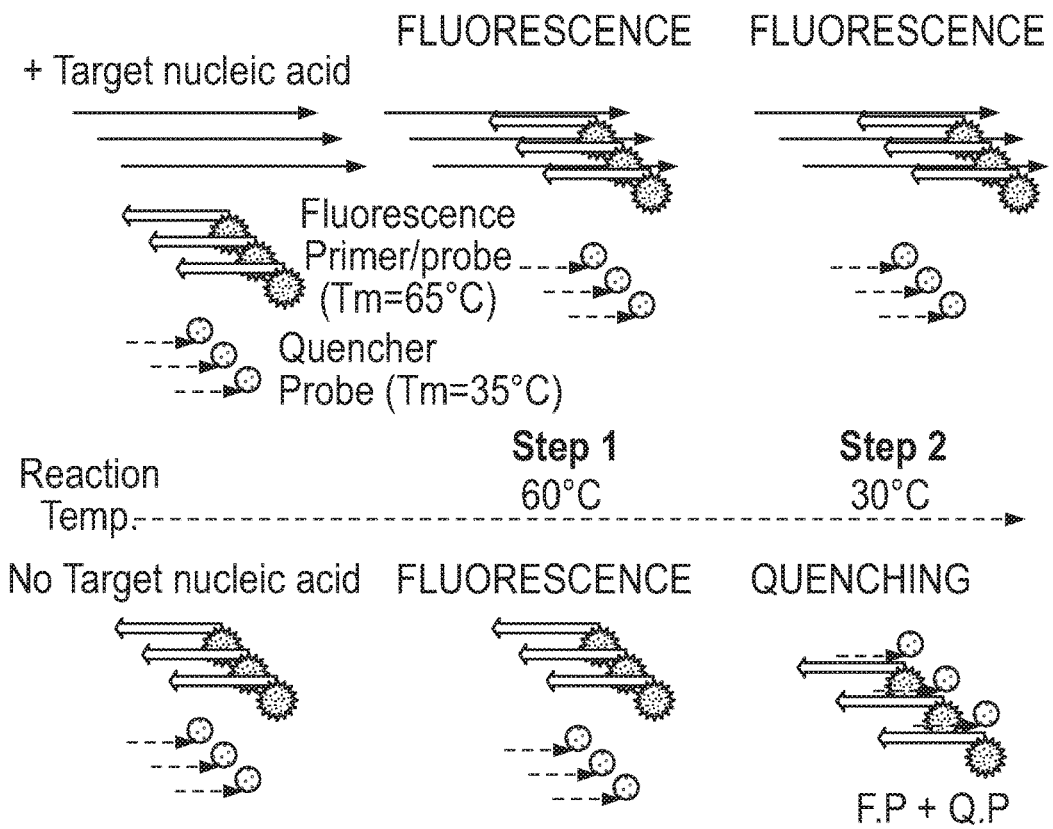
FIG. 1 is a schematic diagram showing a basic aspect of the method of the present invention.

Hereinafter, the present invention will be described in detail.

The "sample" refers to a mixture that may contain a "target nucleic acid" to be detected. The sample is derived from being (e.g., blood, saliva, body fluid, and body tissue) including a human, an environment (e.g., soil, seawater, and environmental water (hot spring water, bathtub water, cooling tower water, etc.)), or an artificial or natural material (e.g., processed food such as bread, fermented food such as yogurt, cultivated plants such as rice and wheat, microbes, and viruses) and is usually used through nucleic acid extraction. If necessary, nucleic acid purification may be further performed.

The "target nucleic acid" refers to a nucleic acid molecule to be detected according to the present invention. The type of the nucleic acid may be deoxyribonucleotide (DNA), ribonucleotide (RNA), or a mixture or a conjugate thereof. Bases constituting the nucleic acid may be naturally occurring nucleotides, for example, guanine (G), adenine (A), thymine (T), cytosine (C), and uracil (U) or may contain other natural and artificial modified bases. In this context, the "modified base" means a base in which any of these 5 nucleotides have undergone chemical modification. Examples of the modified base include, but not limited to, methylcytidine, pseudouridine, 4-thiouridine, dihydrouridine, queuosine, and hypoxanthine (inosine (I)). In the present invention, the target nucleic acid needs to be single-stranded when detected. Even a double-stranded nucleic acid or a nucleic acid having a conformation, however, may be used after being converted to single strands by thermal denaturation, alkali denaturation treatment, or the like. The target nucleic acid of the present invention also includes such denatured forms. Alternatively, the "target nucleic acid" also includes cDNA prepared through reverse transcription reaction from an RNA template.

The "oligonucleotide" means a linear oligomer composed of a linkage through phosphodiester bonds of nucleosides such as adenosine, thymidine, cytidine, guanosine, and uridine or nucleosides having a modified base and refers to DNA, RNA, or a conjugate thereof. In some cases, a peptide nucleic acid (PNA) may be used.

The "complementarity" not only means that a polynucleotide or oligonucleotide strand is annealed to another strand to form a double-stranded structure where the respective nucleotides of the strands form Watson-Crick base pairs, but means that the nucleotides form non-Watson-Crick base pairs such as pairs of modified nucleotides having a deoxyinosine (dI) or 2-aminopurine base.

The "fluorophore" means a molecule or a functional group that releases redundant energy as an electromagnetic wave (emitted light) when returning to the ground state from the excited state of electrons resulting from the absorption of the energy of irradiated excitation light with a given wavelength. Specific examples thereof include, but not limited to, fluorescein and its derivatives (fluorescein phosphoramidite (FAM), fluorescein isothiocyanate, etc.), rhodamine and its derivatives (Texas Red, etc.), and Cy dyes (Cy3, Cy5, etc.).

The "quencher" means a molecule or a functional group having an appropriate energy level so as to absorb the energy of the emitted light of the fluorophore. A fluorophore may be used as the quencher, and, for example, tetramethylrhodamine (TAMRA) can be used as the quencher for fluorescein phosphoramidite (FAM). However, a molecule or a functional group that absorbs and excites the emitted light of the fluorophore, but does not emit light in itself is more suitable as the quencher. Examples thereof include, but, not limited to, DABCYL, Black Hole Quencher (BHQ™ (Biosearch Technologies, Inc.)), and Eclipse™ Dark Quencher (Epoch Biosciences, Inc.).

The "incubation" means that the sample is left at a particular temperature. Examples of means for thermal conductivity include, but not limited to, water baths, air baths, and metal baths.

The melting temperature (Tm) means the temperature at which ½ of DNA molecules are dissociated into single strands during the heating of a double-stranded DNA solution. In the present invention, the melting temperature is calculated according to the following expression of the nearest neighbor method using 50 mM Na$^+$ concentration (Na$^+$=50×10$^{-3}$) and 0.5 mM oligonucleotide concentration (Ct=0.5×10$^{-6}$) (Nucl. Acids Res. (1990) 18 (21): 6409-6412).

$$Tm=\{(1000\Delta H)/(-10.8+\Delta S+Rln(Ct/4))\}-273.15\pm16.6 \log[Na^+]$$

In this context, ΔH represents a total [kcal/mol] of changes in nearest neighbor enthalpy in a hybrid; ΔS represents a total [cal/mol·K] of changes in nearest neighbor entropy in the hybrid; R represents a gas constant (1.987 cal/deg·mol); Ct represents the total molar concentration [mol/l] of the oligo; and Na$^+$ represents a molar concentration [mol/l].

The melting temperature (Tm) varies depending on the nucleotide sequence of the oligonucleotide and its length. An oligonucleotide having larger guanine and cytosine contents or having a larger length has a higher melting temperature (Tm). Thus, the melting temperature may be adjusted by allowing a melting temperature adjuster to be contained in the reaction solution, though the annealing temperature is determined depending on the nucleotide sequence and its length.

Examples of the melting temperature adjuster used in a nucleic acid amplification method include formamide, betaine (N,N,N,-trimethylglycine), proline, dimethyl sulfoxide, trimethylamine N-oxide, and tetraalkylammonium salt.

The "fluorophore-labeled primer or probe (hereinafter, referred to as a fluorophore-labeled primer/probe)" refers to an "oligonucleotide" bound with a "fluorophore" and has complementarity to each target nucleic acid. In an aspect where the target nucleic acid is not amplified, the fluorophore-labeled primer/probe is used only as a "probe". In an aspect where the target nucleic acid is amplified, the fluorophore-labeled primer/probe can be used as a "primer". The "fluorophore-labeled primer/probe" may be synthesized using a fluorophore-bound (mono)nucleotide, for example, Alexa Fluor™ nucleotide (Invitrogen Corp.). Alternatively, a synthesized oligonucleotide may be bound 5'-terminally or 3'-terminally with the fluorophore. However, the 3' end should not be bound to the fluorophore in the case of amplifying the target nucleic acid using the "fluorophore-labeled primer/probe", i.e., in the case of using the "fluorophore-labeled primer/probe" in a "primer" form. An "oligonucleotide" 5'-terminally bound with the fluorophore is more preferred. The nucleotide sequence of the "fluorophore-labeled primer/probe" is not particularly limited by its length and is preferably 15 bases or longer, more preferably 20 bases or longer, further preferably 25 bases or longer. Desirably, the length of the nucleotide sequence of the "fluorophore-labeled primer/probe" is designed in consideration of annealing to the target nucleic acid and temperature conditions of subsequent amplification reaction such that the "fluorophore-labeled primer/probe" has a melting temperature (Tm) of 30 to 70° C., preferably 50 to 65° C.

The "quencher-labeled probe" refers to an "oligonucleotide" bound with a "quencher". The "quencher-labeled probe" may be synthesized using a quencher-bound nucleotide. Alternatively, a synthesized oligonucleotide may be bound 5'-terminally or 3'-terminally with the quencher. Preferably, the quencher is bound to the position at which the quencher effectively quenches the emitted light (fluorescence) of the fluorophore in the "fluorophore-labeled primer/probe" when the "quencher-labeled probe" and the "fluorescently labeled primer/probe" are annealed to each other. In an aspect involving target nucleic acid amplification, the 3' end of the oligonucleotide of the "quencher-labeled probe" is preferably blocked so as not to cause extension reaction. More preferably, when the "fluorophore-labeled primer/probe" is an "oligonucleotide" 5'-terminally bound with the fluorophore, a desirable "quencher-labeled probe" has the quencher bound with the 3' end and is compatible with the "oligonucleotide".

Desirably, the nucleotide sequence of the oligonucleotide of the "quencher-labeled probe" has complementarity to the nucleotide sequence of the "fluorophore-labeled primer/probe" and has a length 2, 3, 4, 5, 6, 7, 8, 9, 10 or more bases shorter than the fluorophore-labeled primer/probe. More preferably, the nucleotide sequence is shorter because the 5'-terminal bases of the "quencher-labeled probe" are fewer than the 3'-terminal bases of the "fluorophore-labeled primer/probe". Alternatively, the "quencher-labeled probe" may be allowed to have a melting temperature (Tm) substantially lower than that of the "fluorophore-labeled primer/probe" by use of a nucleotide having a modified base effective for decreasing Tm, even if the "quencher-labeled probe" has the same nucleotide sequence length as the "fluorophore-labeled primer/probe". The nucleotide having a modified base effective for decreasing Tm is, for example, a nucleotide having inosine. More preferably, the nucleotide sequence of the oligonucleotide of the "quencher-labeled probe" is designed such that its melting temperature is equal to or higher than room temperature (e.g., 25° C., 26° C., 27° C., 28° C., 29° C., or 30° C.). The oligonucleotide length is preferably 7 bases or longer, more preferably 9 bases or longer, for satisfying these conditions.

In the present invention, it is required that the fluorophore-labeled primer/probe and the quencher-labeled probe should differ in melting temperature (Tm). The quencher-labeled probe has a melting temperature (Tm) lower than that of the fluorophore-labeled primer/probe. More specifically, the melting temperature (Tm) of the quencher-labeled probe is preferably 5° C. lower, more preferably 10° C. lower, even more preferably 15° C. lower, further preferably 20° C. lower, still further preferably 30° C. lower, still further preferably 35° C. lower, particularly preferably 40° C. or at least 45° C. lower than that of the 1 fluorophore-labeled primer/probe.

The "addition" to the sample includes an aspect where reagents such as the fluorophore-labeled primer/probe and the quencher-labeled probe are added to the sample as well as an aspect where the sample is added to the reagents.

The molar ratio of the "fluorophore-labeled primer/probe" to the "quencher-labeled probe" used for addition can be 1:1, 1:2, or 1:10 or more and is more preferably 1:2 or more.

The "immobilization on a solid-phase surface" means that the "fluorophore-labeled primers/probes" are unevenly distributed during reaction. Specifically, the immobilization on a solid-phase surface means that, but not limited to, the "fluorophore-labeled primers/probes" are immobilized on the surface of glass, a nylon membrane, a semiconductor wafer, microbeads, or the like. The immobilization method can be carried out using a technique known in the art. The oligonucleotide sites of the "fluorophore-labeled primers/probes" may be immobilized directly on the glass surface or the like or may be immobilized indirectly via biotin-avidin binding or the like or via a linker molecule.

The "amplification of a target nucleic acid using the fluorophore-labeled primer/probe" means that the target nucleic acid is amplified through polymerase-mediated extension using the fluorophore-labeled primer/probe as a primer. It is obvious to those skilled in the art that in an aspect comprising the step of amplifying target nucleic acids of the present invention, as a matter of course, the "fluorophore-labeled primer/probe" and the "quencher-labeled probe", and the sample are supplemented with other reagents necessary for the target nucleic acid amplification, for example, primers, polymerase, and dNTPs, according to the amplification method to be carried out.

The phrase "amplification is performed under isothermal conditions" means that each target nucleic acid is amplified with temperature kept constant. Examples of the isothermal amplification method include isothermal and chimeric primer-initiated amplification of nucleic acids (ICAN), SDA, NASBA, RCA, smart amplification process version 2 (SMAP2) (Nature Methods 4: 257-262 (2007)), and LAMP.

The "UV irradiation" refers to irradiation with an electromagnetic wave having a wavelength on the order of 10 nm to 400 nm. The wavelength of the electromagnetic wave may not be controlled strictly and needs only to correspond to the excitation light of the fluorophore.

The "visual determination" means that the presence or absence of the emitted light of the fluorophore is determined with the naked eyes in a short time, for example, within 5 seconds, 15 seconds, 30 seconds, or 1 minute from UV irradiation. In some cases, the visual determination may be performed by comparison to color samples.

For the "visual determination", excitation by "UV irradiation" is most suitable, and simultaneous multiple-item (up to approximately 3 to 4 items) detection is achieved. Measurement using a "fluorescence detector" may achieve more multiple-item simultaneous detection using a photodiode array detector or the like.

The "kit" means reagents for use in the detection method according to the present invention. The kit comprises the "fluorophore-labeled primer/probe" and the "quencher-labeled probe" and may optionally comprise reagents, tools, and instruments necessary for the detection. The kit may further comprise an instruction manual of the "kit" and color samples. In an aspect involving nucleic acid amplification, the kit may further comprise reagents necessary for the nucleic acid amplification.

In the detection method of the present invention, each target nucleic acid is annealed to the fluorophore-labeled primer/probe preferentially by incubation at a temperature equal to or lower than the melting temperature (Tm) of the fluorophore-labeled primer/probe and higher than the melting temperature (Tm) of the quencher-labeled probe. Subsequently, a fluorophore-labeled primer/probe unannealed to the target nucleic acid is annealed to the quencher-labeled probe by incubation at a temperature equal to or lower than the melting temperature (Tm) of the quencher-labeled probe. As a result, the fluorophore in the fluorophore-labeled primer/probe unannealed to the target nucleic acid is located adjacent to the quencher in the quencher-labeled probe. While the sample is kept at the temperature equal to or lower than the melting temperature (Tm) of the quencher-labeled probe, the fluorescence of the fluorophore-labeled primer/probe bound with the target nucleic acid is measured to detect the target nucleic acid.

A feature of the detection method of the present invention is that: the "fluorophore-labeled primer/probe" and the "quencher-labeled probe" have distinct melting temperatures (Tm); and for the detection of the "target nucleic acid", the annealing between the "fluorophore-labeled primer/probe" and the "target nucleic acid" prevails over the annealing between the "fluorophore-labeled primer/probe" and the "quencher-labeled probe" as a result of controlling the relationship of these melting temperatures with reaction temperatures. In addition, the method of the present invention eliminates the need of adding, after amplification reaction, the fluorophore-labeled primer/probe and the quencher-labeled probe necessary for the detection and can therefore be performed by more convenient operation and more prevent contamination attributed to the release of amplification products, compared with conventional techniques.

Hereinafter, each aspect of the present invention will be disclosed in detail. However, the present invention is not intended to be limited thereto.

The most basic aspect of the present invention is as shown in FIG. 1. Provided that the "fluorophore-labeled primer/probe" and the "quencher-labeled probe" are added first, each target nucleic acid can be detected in a closed system without subsequently adding any reagent. For example, the fluorophore-labeled primer/probe may have a Tm value of 65° C., while the quencher-labeled probe may have a Tm value of 35° C. In such a case, the fluorophore-labeled primer/probe binds to the target nucleic acid, but does not bind to the quencher-labeled probe at a reaction temperature set to 60° C. (Step 1). When the reaction temperature is then decreased to a temperature (30° C.) equal to or lower than the Tm value of the quencher-labeled probe (Step 2), the "fluorophore-labeled primer/probe" unbound with the target nucleic acid is annealed to the "quencher-labeled probe". Only the fluorophore in the "fluorophore-labeled primer/probe" bound with the "target nucleic acid" emits light (fluorescence) upon UV irradiation, whereas the fluorescence of the fluorophore in the "fluorophore-labeled primer/probe" bound with the "quencher-labeled probe" cannot be detected. Thus, the fluorescence intensity of the sample depends on the amount of the "target nucleic acid" in the sample.

Figure 2:
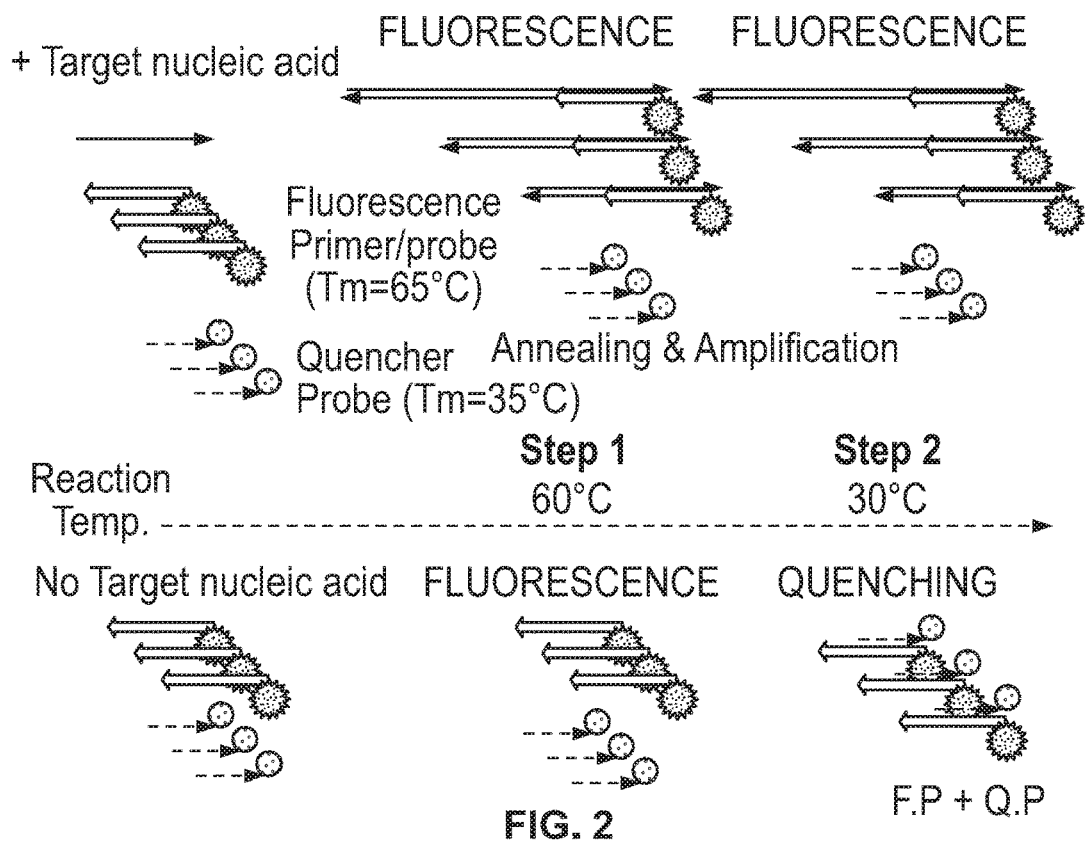
FIG. 2 is a schematic diagram showing the method of the present invention further comprising the step of amplifying target nucleic acids.

FIG. 2 shows an aspect of the present invention comprising the step of amplifying target nucleic acids. In nucleic acid amplification and detection methods as described in the conventional techniques of Japanese Patent Nos. 3016759 and 3999653, a fluorophore-labeled probe annealed to a target nucleic acid coexists with a fluorophore-labeled probe annealed to a quenchingly labeled probe at the stage of annealing in PCR. Accordingly, the fluorescence intensity is proportional to the amount of the amplified target nucleic acid, but does not directly indicate the amount of the amplified target nucleic acid. In addition, the fluorophore-labeled probe and the quenchingly labeled probe may inhibit subsequent extension reaction. The conventional techniques are therefore poorly accurate. On the other hand, according to the aspect of the present invention shown in FIG. 2, the fluorophore-labeled primer/probe is incorporated into the amplified double-stranded product. Hence, only the amount of the amplified target nucleic acid can be detected more accurately.

FIG. 3 shows an aspect where the method of the present invention is applied to a so-called DNA chip or microarray.

Figure 3A:
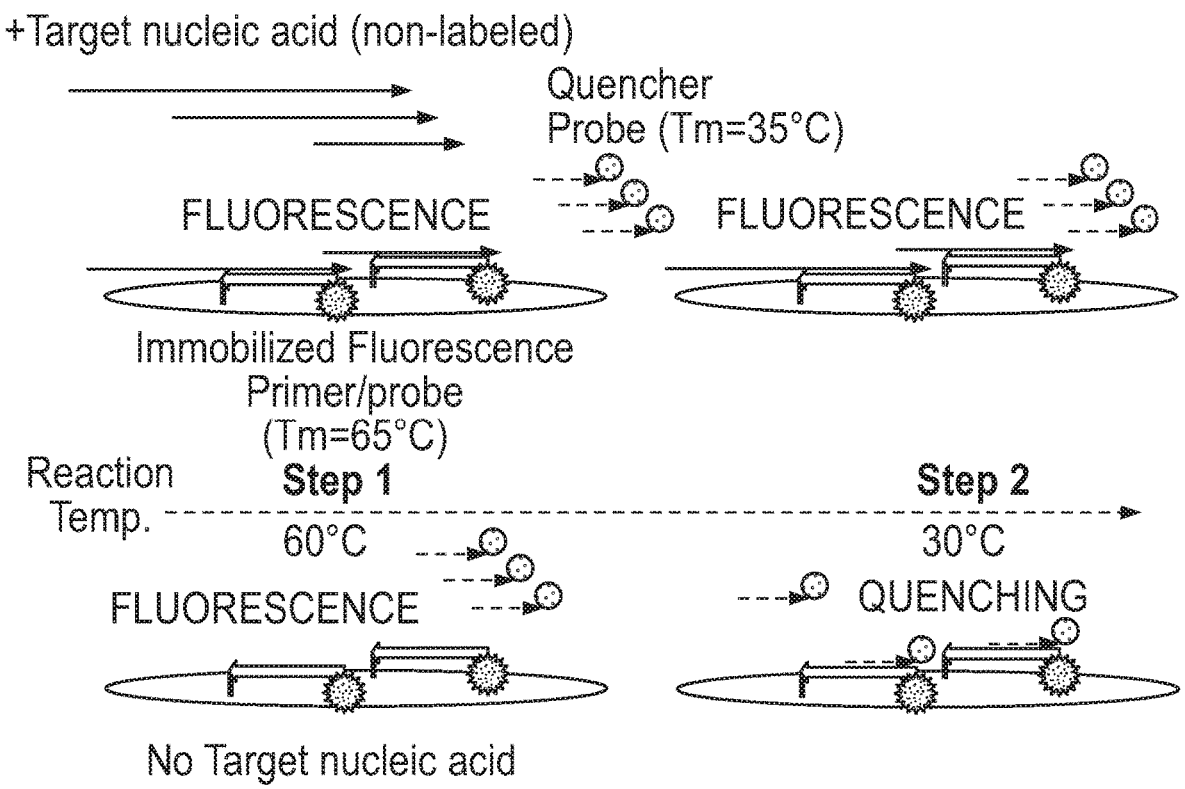
FIG. 3A is a schematic diagram showing the method of the present invention applied to a microarray (aspect without amplifying target nucleic acids).

FIG. 3A is a schematic diagram showing the method of the present invention using the fluorophore-labeled primer/probe in a probe form (aspect without the step of amplifying target nucleic acids). In this case, the fluorophore-labeled primer/probe may be immobilized at the 3' end of its oligonucleotide on the solid-phase surface.

Figure 3B:
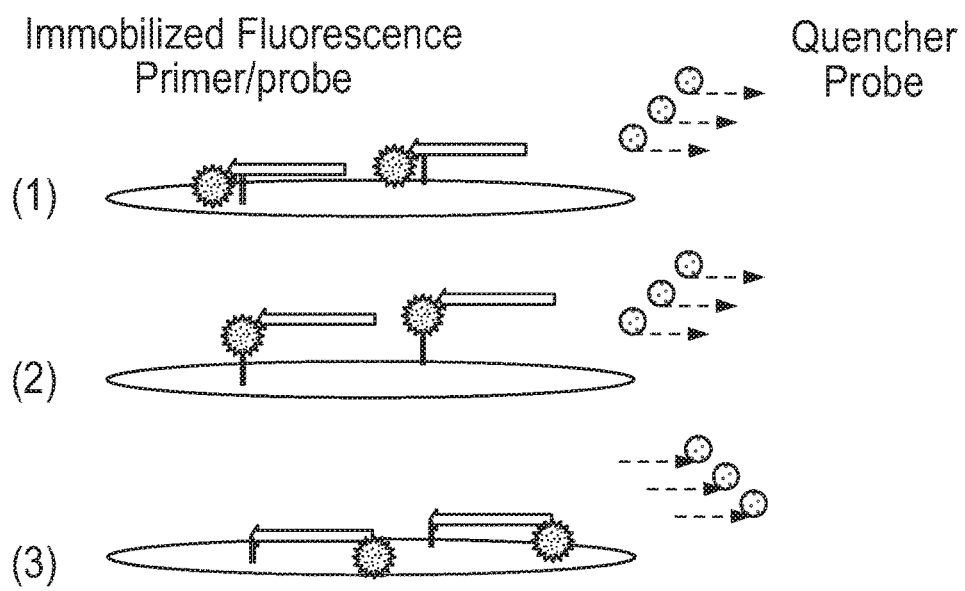
FIG. 3B is a schematic diagram showing an example of immobilization of fluorophore-labeled primers/probes in the method of the present invention applied to a microarray.

Examples of immobilized forms are shown in FIG. 3B.
(1) The fluorophore-labeled primer/probe is immobilized at the 3' end of its oligonucleotide on the surface. In this case, the compatible quencher-labeled probe desirably has the quencher bound with the 5' end.
(2) The fluorophore-labeled primer/probe is immobilized thereon via the fluorophore bound with the 3' end of the oligonucleotide. In this case, the compatible quencher-labeled probe desirably has the quencher bound with the 5' end.
(3) The fluorophore-labeled primer/probe has the fluorophore bound with the 5' end of the oligonucleotide and is immobilized thereon at the 3' end of the oligonucleotide. In this case, the compatible quencher-labeled probe desirably has the quencher bound with the 3' end.

Figure 3C:
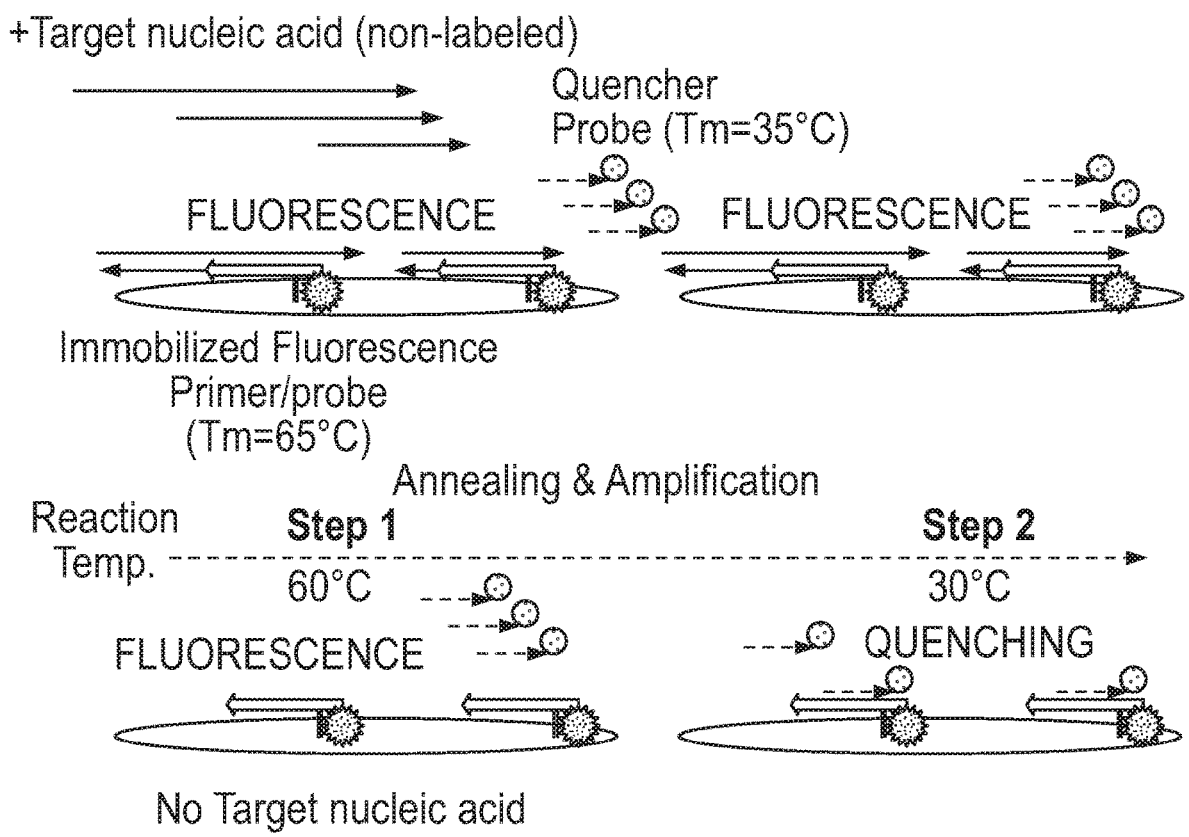
FIG. 3C is a schematic diagram showing the method of the present invention applied to a microarray (aspect involving the step of amplifying target nucleic acids).

FIG. 3C shows an aspect comprising the step of amplifying target nucleic acids. In this case, it is preferred that the fluorophore-labeled primer/probe should not be immobilized at the 3' region of its oligonucleotide on the surface. In the aspect comprising the nucleic acid amplification step, the target nucleic acid is bound more stably with the fluorophore-labeled primer/probe.

Nucleic acids to be bound with a microarray are labeled with a radioisotope, a fluorophore, or the like and annealed to, for example, unlabeled immobilized oligonucleotides. Then, unbound labeled nucleic acids are washed off. Then, the labels of the nucleic acids bound with the microarray through annealing can be detected to thereby detect the nucleic acids. As is evident from the aspect of FIG. 3, however, use of the fluorescently labeled primer/probe bound with the solid-phase surface eliminates the need of fluorescently labeling the whole sample and also eliminates the need of the washing step. Thus, target nucleic acids can be detected more conveniently.

According to the present invention, plural target nucleic acids can be detected simultaneously by using plural fluorophore-labeled primers/probes, i.e., plural fluorophore-labeled primers/probes respectively having fluorophore labels emitting distinct lights, and quencher-labeled probes respectively compatible therewith. The fluorophores in the fluorophore-labeled primers/probes each release redundant energy as an electromagnetic wave (emitted light) when returning to the ground state from the excited state of electrons resulting from the absorption of external energy.

The difference in energy level between the excited state and the ground state is specific for each fluorophore. Different fluorophores emit lights (electromagnetic waves) with their respective fluorophore-specific wavelengths, i.e., emit "lights with different colors", even if absorbing external energy at the same time. These emitted lights are absorbed and quenched only by the quenchers in the compatible quencher-labeled probes and are not influenced by other quencher-labeled probes. Thus, plural target nucleic acids can be detected simultaneously by looking at the "wavelengths", i.e., "colors", of the emitted lights of the fluorophores. These emitted lights can each be detected using a spectrophotometer or the like and may be detected as mixed color of or color between the fluorescence colors with the naked eyes.

The detection method of the present invention can be applied to the detection of various pathogens including bacteria, fungi, and viruses. Examples of the bacteria include *Mycoplasma pneumoniae*, bacteria of the genus *Legionella*, bacteria of the genus *Salmonella*, enterohemorrhagic *E. coli*, *Mycobacterium tuberculosis*, *Campylobacter jejuni* and *Campylobacter coli*, and *Bordetella pertussis*. Examples of the fungi include fungi of the genus *Candida*, fungi of the genus *Aspergillus*, and fungi of the genus *Cryptococcus*. Examples of the viruses include influenza A (H1N1) pdm virus, influenza A (H1N1) virus, H5 subtype influenza virus, SARS coronavirus, herpes simplex virus type 1/2 (HSV-1/2), and noroviruses genogroup I (GI) and genogroup II (GII). Examples of parasites include malaria parasites, *Cryptosporidium* spp., and *Giardia* spp. The detection method of the present invention not only can detect the pathogen itself but may detect a gene involved in pathogenicity, for example, a toxin gene (e.g., verotoxin (hereinafter, referred to as VT) gene 1 (VT1) and 2 (VT2)), a drug resistance gene, or a gene associated with host infection (invasion, colonization, or proliferation). The detection method of the present invention can be further applied to, for example, the detection of single nucleotide polymorphisms (SNPs) in cytochrome gene or the like, or the detection of a male-specific gene sequence for sex discrimination of bovine embryos. For such detection, a fluorophore-labeled primer/probe having an oligonucleotide sequence complementary to a nucleic acid sequence specific for a detection subject is first designed, and a quencher-labeled probe compatible therewith is then designed. The detection method of the present invention can be carried out using the designed fluorophore-labeled primer/probe and quencher-labeled probe.

Particularly, the aspect of the present invention for detecting plural target nucleic acids is effective for simultaneously detecting and discriminating viruses of related species such as human influenza viruses (types A (including H1N1, H3N2, H1N2, H2N2, H9N1, and H5N1), B, and C) or hepatitis viruses (hepatitis A virus, hepatitis B virus, and hepatitis C virus). Also, this aspect is effective for simultaneously detecting and discriminating (the presence or absence of) pathogens leading to various kinds of sexually transmitted diseases, such like *Neisseria gonorrhoeae*, *Treponema pallidum*, and *Chlamydia trachomatis*. This aspect is further effective for simultaneously detecting and discriminating (the presence or absence of) noroviruses, rotaviruses, and the like responsible for infectious gastroenteritis. Alternatively, the aspect is effective for simultaneously detecting and discriminating (the presence or absence of) AIDS virus (HIV), hepatitis B virus (HBV), and hepatitis C virus (HCV) as a screening test for blood supply.

The kit of the present invention is a kit for target nucleic acid detection that is used for detecting one or more target nucleic acids present in a sample with or without the use of amplification. The kit for target nucleic acid detection comprises one or more combinations each comprising: a fluorophore-labeled primer/probe which is a fluorophore-labeled oligonucleotide having complementarity to a target nucleic acid; and a quencher-labeled probe which is a quencher-labeled oligonucleotide having complementarity to the fluorophore-labeled primer/probe and having a melting temperature (Tm) lower than that of the fluorophore-labeled primer/probe.

The oligonucleotide of the quencher-labeled probe has a base length shorter than that of the oligonucleotide of the fluorophore-labeled primer/probe. Alternatively, the oligonucleotide of the quencher-labeled probe comprises a modified base.

The fluorophore-labeled primer/probe may be immobilized on a solid-phase surface. The kit of the present invention may comprise other reagents for target nucleic acid amplification and may optionally comprise other reagents necessary for use in usual nucleic acid detection.

Hereinafter, the present invention will be described specifically with reference to Examples. However, the present invention is not intended to be limited by these Examples.

EXAMPLES

Example 1

Confirmation of Influence of Tm Value (1) Assay Template

A portion (SEQ ID NO: 21) of a *Chlamydia trachomatis* cryptic plasmid region was subcloned as a template for assay to prepare plasmid DNAs (hereinafter, referred to as CT plasmids).

(2) Synthesis of Primer, Fluorescently Labeled Primer/Probe, and Quencher-Labeled Probe Primers for LAMP reaction were designed to target the *Chlamydia trachomatis* cryptic plasmid region and have no cross-reactivity with related bacteria. Of the designed primers, LB 5'-terminally fluorescently labeled with FAM was used as a fluorescently labeled primer/probe, while its complementary strand 3'-terminally labeled with BHQ1 was used as a quencher-labeled probe. Also, quencher-labeled probes having a lower Tm value were designed, in which 5'-terminal 3 to 10 bases of each quencher-labeled probe were deleted. Primer synthesis was outsourced to Operon Biotechnologies Inc. The synthesis of the fluorophore-labeled primer/probe and the quencher-labeled probes was outsourced to Japan Bio Services Co., Ltd. The Tm values of the quencher-labeled probes are indicated in values calculated by the nearest neighbor method.

```
<Chlamydia trachomatis primer>
CT-FIP:
                                        (SEQ ID NO: 1)
5'-CAAGCAGGACTACAAGCTGCAGCGTTTGTACTCCGTCAC-3'

CT-BIP:
                                        (SEQ ID NO: 2)
5'-GCGGGCGATTTGCCTTAACTCGGTCAACGAAGAGGTT-3'

CT-F3:
                                        (SEQ ID NO: 3)
5'-AIGTCGGAGTCTGAGCAC-3'

CT-B3:
                                        (SEQ ID NO: 4)
5'-CCTCAGAAGTTTATGCACTTTC-3'

CT-LF:
                                        (SEQ ID NO: 5)
5'-AAGATAACCCCGCACGT-3'

CT-LB:
                                        (SEQ ID NO: 6)
5'-GGAGCGAGTTACGAAGACA-3'

<Chlamydia trachomatis fluorophore-labeled
primer/probe>
FAM-CT-LB:
                                        (SEQ ID NO: 7)
5'-(FAM)-GGAGCGAGTTACGAAGACA-3'

<Chlamydia trachomatis quencher-labeled probe>
CT-LBc-Q1-0:
                                        (SEQ ID NO: 8)
5'-TGTCTTCGTAACTCGCTCC-(BHQ1)-3'
Tm = 60.6° C.

CT-LBc-Q1-3:
                                        (SEQ ID NO: 9)
5'-CTTCGTAACTCGCTCC-(BHQ1)-3'
Tm = 53.9° C.

CT-LBc-Q1-5:
                                        (SEQ ID NO: 10)
5'-TCGTAACTCGCTCC-(BHQ1)-3'
Tm = 49.7° C.

CT-LBc-Q1-6:
                                        (SEQ ID NO: 11)
5'-CGTAACTCGCTCC-(BHQ1)-3'
Tm = 46.5° C.

CT-LBc-Q1-7:
                                        (SEQ ID NO: 12)
5'-GTAACTCGCTCC-(BHQ1)-3'
Tm = 37.5° C.

CT-LBc-Q1-9:
                                        (SEQ ID NO: 13)
5'-AACTCGCTCC-(BHQ1)-3'
Tm = 32.6° C.

CT-LBc-Q1-10:
                                        (SEQ ID NO: 14)
5'-ACTCGCTCC-(BHQ1)-3'
Tm = 26.7° C.
```

(3) Composition and Concentration of LAMP Reaction Reagent

LAMP final reaction solutions were prepared such that each reagent had a concentration shown below in 30 μL each of the reaction solutions. These reaction solutions were not supplemented with any quencher-labeled probe (control) or supplemented with any of CT-LBc-Q1-0 (SEQ ID NO: 8), CT-LBc-Q1-3 (SEQ ID NO: 9), CT-LBc-Q1-5 (SEQ ID NO: 10), CT-LBc-Q1-6 (SEQ ID NO: 11), CT-LBc-Q1-7 (SEQ ID NO: 12), CT-LBc-Q1-9 (SEQ ID NO: 13), and CT-LBc-Q1-10 (SEQ ID NO: 14).

30 mM Tris-HCl (pH 8.8)
15 mM KCl
15 mM $(NH_4)_2SO_4$
12 mM $MgSO_4$
0.15% Tween 20
2.1 mM dATP (GeneACT, Inc.)
2.1 mM dCTP (GeneACT, Inc.)
2.1 mM dGTP (GeneACT, Inc.)
2.1 mM dTTP (GeneACT, Inc.)
38.4 U Bst DNA polymerase (New England Biolabs Inc.)

Primer, Fluorophore-Labeled Primer/Probe and Quencher-Labeled Probe:

0.8 μM CT-FIP (SEQ ID NO: 1)
0.8 μM CT-BIP (SEQ ID NO: 2)
0.1 μM CT-F3 (SEQ ID NO: 3)
0.1 μM CT-B3 (SEQ ID NO: 4)
0.4 μM CT-LF (SEQ ID NO: 5)
0.4 μM FAM-CT-LB (SEQ ID NO: 7)
0.8 μM CT-LBc-Q1-0 (SEQ ID NO: 8), CT-LBc-Q1-3 (SEQ ID NO: 9), CT-LBc-Q1-5 (SEQ ID NO: 10), CT-LBc-Q1-6 (SEQ ID NO: 11), CT-LBc-Q1-7 (SEQ ID NO: 12), CT-LBc-Q1-9 (SEQ ID NO: 13) or CT-LBc-Q1-10 (SEQ ID NO: 14)

(4) Amplification

Distilled water (DW) or $10^4$ copies of CT plasmids were added per reaction. Amplification reaction was performed at 65° C. for 120 minutes using a real-time turbidimetric apparatus LA-320C (Teramecs Co., Ltd.).

(5) Determination

The amplification reaction was confirmed using LA-320C (LA-320C monitors nucleic acid amplification reaction on the basis of change in absorbance caused by the formation of its by-product magnesium pyrophosphate, i.e., change in turbidity; Tt value: time required for the arithmetic value of turbidmetric data to reach a determination value from the start of the reaction; turbidity curve: plot of the real-time assay data of turbidity), while reaction tubes after amplification were irradiated with UV and found positive when emitting green fluorescence (FAM) or negative when emitting no detectable fluorescence.

When no quencher-labeled probe was used, the amplification of $10^4$ copies of CT plasmids was confirmed at 20.7 minutes. By contrast, the amplification times of the CT plasmids supplemented with the quencher-labeled probes differed depending on the quencher-labeled probes and were 92.4 minutes (+71.7 minutes) for CT-LBc-Q1-0 (SEQ ID NO: 8), 41.5 minutes (+20.8 minutes) for CT-LBc-Q1-3 (SEQ ID NO: 9), 27.8 minutes (+7.1 minutes) for CT-LBc-Q1-5 (SEQ ID NO: 10), 25.5 minutes (+4.8 minutes) for CT-LBc-Q1-6 (SEQ ID NO: 11), 22.8 minutes (+2.1 minutes) for CT-LBc-Q1-7 (SEQ ID NO: 12), 20.7 minutes (+0.0 minutes) for CT-LBc-Q1-9 (SEQ ID NO: 13), and 20.6 minutes (−0.1 minutes) for CT-LBc-Q1-10 (SEQ ID NO: 14). In any of the cases where the quencher-labeled probes were used, FAM-derived green fluorescence was confirmed in the tubes supplemented with the CT plasmids, but was not confirmed in the tubes supplemented with DW (Table 1).

TABLE 1

Tm value of quencher-labeled probe and amplification time

| CT-LBc- | — | Q 1-0 | Q 1-3 | Q 1-5 | Q 1-6 | Q 1-7 | Q 1-9 | Q 1-10 |
|---|---|---|---|---|---|---|---|---|
| Tm | — | 60.6 | 53.9 | 49.7 | 46.5 | 37.5 | 32.6 | 26.7 |
| Tt (DW) | N.D.* | N.D.* | N.D.* | N.D.* | N.D.* | N.D.* | N.D.* | N.D.* |
| Tt (CT) | 20.7 | 92.4 | 41.5 | 27.8 | 25.5 | 22.8 | 20.7 | 20.6 |
| ⊿t | | 71.7 | 20.8 | 7.1 | 4.8 | 2.1 | 0.0 | −0.1 |

N.D.*: Not Detect (Not Detect)

"Tt(DW)" represents a Tt value derived from the addition of DW. "Tt(CT)" represents a Tt value derived from the reaction of $10^4$ copies of CT plasmids added per reaction.

In the absence of CT-LBc-Q1, fluorescence was confirmed even in the tubes supplemented with DW, because the fluorescent label was not quenched. In the presence of CT-LBc-Q1 (Q1-0), fluorescence was quenched in any of the tubes supplemented with DW and confirmed in the tubes supplemented with the CT plasmids without being influenced by the Tm value of CT-LBc-Q1.

As shown in [Table 1], larger Tm values of the quencher-labeled probes more delay amplification times, whereas this influence is not found at Tm values of 32.6° C. or lower. This suggested that Tm of the quencher-labeled probe is desirably 32.6° C. or lower.

Example 2

The Case of Quencher-Labeled Probe is Added After LAMP Amplification (1) Assay Template A portion (SEQ ID NO: 21) of a *Chlamydia trachomatis* cryptic plasmid region was subcloned as a template for assay to prepare plasmid DNAs (hereinafter, referred to as CT plasmids).

(2) Synthesis of Primer, Fluorophore-Labeled Primer/Probe, and Quencher-Labeled Probe Primers were designed to target the *Chlamydia trachomatis* cryptic plasmid region and have no cross-reactivity with related bacteria. Of the designed primers, LB 5'-terminally fluorescently labeled with FAM was used as a fluorophore-labeled primer/probe, while its complementary strand 3'-terminally labeled with BHQ1 was used as a quencher-labeled probe. Primer synthesis was outsourced to Operon Biotechnologies Inc. The synthesis of the fluorophore-labeled primer and the quencher-labeled probes was outsourced to Japan Bio Services Co., Ltd.

<*Chlamydia trachomatis* primer>
CT-FIP:
(SEQ ID NO: 1)
5'-CAAGCAGGACTACAAGCTGCAGCGTTTGTACTCCGTCAC-3'

CT-BIP:
(SEQ ID NO: 2)
5'-GCGGGCGATTTGCCTTAACTCGGTCAACGAAGAGGTT-3'

CT-F3:
(SEQ ID NO: 3)
5'-ATGTCGGAGTCTGAGCAC-3'

CT-B3:
(SEQ ID NO: 4)
5'-CCTCAGAAGTTTATGCACTTTC-3'

CT-LF:
(SEQ ID NO: 5)
5'-AAGATAACCCCGCACGT-3'

CT-LB:
(SEQ ID NO: 6)
5'-GGAGCGAGTTACGAAGACA-3'

<*Chlamydia trachomatis* fluorophore-labeled primer>
FAM-CT-LB:
(SEQ ID NO: 7)
5'-(FAM)-GGAGCGAGTTACGAAGACA-31

<*Chlamydia trachomatis* quencher-labeled probe>
CT-LBc-Q1-0:
(SEQ ID NO: 8)
5'-TGTCTTCGTAACTCGCTCC-(BHQ1)-3'

(3) Composition and Concentration of LAMP Reaction Reagent

LAMP final reaction solutions were prepared such that each reagent had a concentration shown below in 30 μL each of the reaction solutions.

30 mM Tris-HCl (pH 8.8)
15 mM KCl 15 mM $(NH_4)_2SO_4$
12 mM $MgSO_4$
0.15% Tween 20
2.1 mM dATP (GeneACT, Inc.)
2.1 mM dCTP (GeneACT, Inc.)
2.1 mM dGTP (GeneACT, Inc.)
2.1 mM dTTP (GeneACT, Inc.)
38.4 U Bst DNA polymerase (New England Biolabs Inc.)
Primer and Fluorophore-Labeled Primer/Probe:
0.8 µM CT-FP (SEQ ID NO: 1)
0.8 µM CT-BP (SEQ ID NO: 2)
0.1 µM CT-F3 (SEQ ID NO: 3)
0.1 µM CT-B3 (SEQ ID NO: 4)
0.4 µM CT-LF (SEQ ID NO: 5)
0.4 µM FAM-CT-LB (SEQ ID NO: 7)

The following reagent was also added after amplification reaction.

Quencher-Labeled Probe:
0.8 µM CT-LBc-Q1-0 (SEQ ID NO: 8)

(4) Amplification

DW or $10^4$ copies of CT plasmids were added per reaction. Amplification reaction was performed at 65° C. for 120 minutes using LA-320C.

(5) Determination

Figure 4:
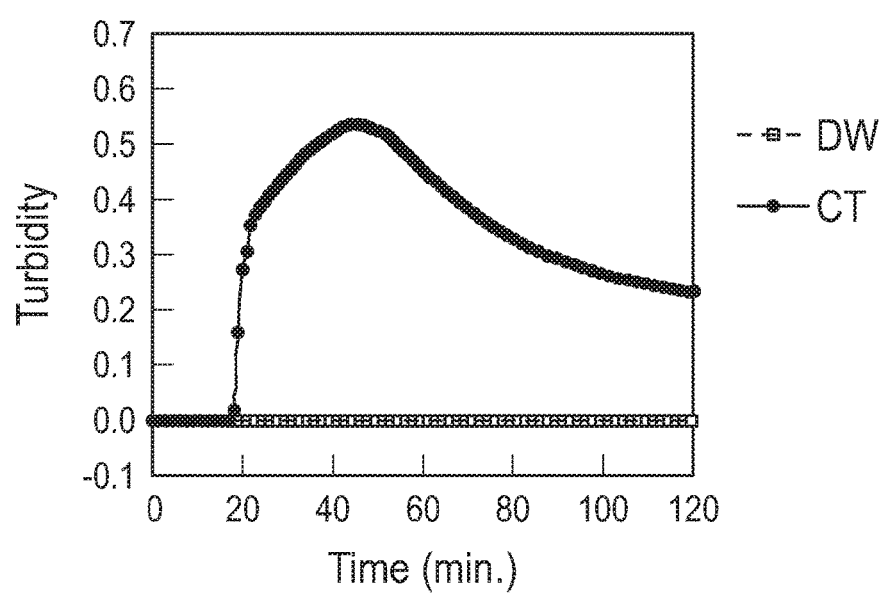
FIG. 4 shows the real-time turbidity curve of a target nucleic acid using fluorophore-labeled primers/probes in Example 2.

The amplification reaction was confirmed using LA-320C in the same way as in Example 1 (Table 2 and FIG. 4).

No Tt value was detected and no rise in turbidity was seen in the reaction tube supplemented with DW. By contrast, a Tt value of 18.7 minutes and a rise in turbidity were confirmed in the reaction tube supplemented with the CT plasmids. These results demonstrated that amplification reaction occurred only in the reaction tubes containing the CT plasmids, i.e., the target nucleic acid.

Figure 5:
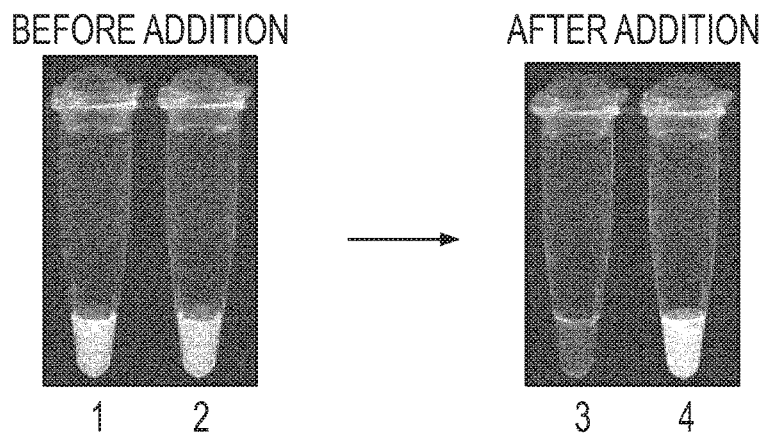
FIG. 5 shows fluorescence detection before and after addition of CT-LBc-Q1-0 (SEQ ID NO: 8) in Example 2.

As for fluorescence from each reaction tube, the fluorescence was detected both in the reaction tube supplemented with DW (Tube No. 1) and in the reaction tube supplemented with the CT plasmids (Tube No. 2) (FIG. 5). Next, CT-LBc-Q1-0 (SEQ ID NO: 8) was added to each reaction tube at room temperature. As a result, the fluorescence was quenched in the reaction tube supplemented with DW (Tube No. 3). By contrast, the fluorescence was retained in the reaction tube supplemented with the CT plasmids (Tube No. 4).

TABLE 2

| Sample | Amplification time | |
|---|---|---|
| | DW | CT |
| Tt | N.D.* | 18.7 |

N.D.*: Not Detect

Example 3

Simultaneous Amplification and Detection Method of *Chlamydia trachomatis* and *Neisseria gonorrhoeae* Using LAMP (1) Assay Template A portion (SEQ ID NO: 21) of a *Chlamydia trachomatis* cryptic plasmid region was subcloned as an internal standard template to prepare plasmid DNAs (hereinafter, referred to as CT plasmids). Also, a portion (SEQ ID NO: 32) of a *Neisseria gonorrhoeae* mtrA region was subcloned as a target nucleic acid template to prepare plasmid DNAs (hereinafter, referred to as NG plasmids).

(2) Synthesis of *Chlamydia trachomatis* Primer, TAMRA-Labeled Loop Primer (Fluorophore-Labeled Primer/Probe), and BHQ2-Labeled Quenching Probe (Quencher-Labeled Probe)

Primers were designed to target the *Chlamydia trachomatis* cryptic plasmid region and have no cross-reactivity with related bacteria. Primer synthesis was outsourced to Operon Biotechnologies Inc. The synthesis of the TAMRA-labeled loop primer and the BHQ2-labeled quenching probe was outsourced to Japan Bio Services Co., Ltd.

<*Chlamydia trachomatis* primer>
CT-FIP:
(SEQ ID NO: 1)
5'-CAAGCAGGACTACAAGCTGCAGCGTTTGTACTCCGTCAC-3'

CT-BIP:
(SEQ ID NO: 2)
5'-GCGGGCGATTTGCCTTAACTCGGTCAACGAAGAGGTT-3'

CT-F3:
(SEQ ID NO: 3)
5'-ATGTCGGAGTCTGAGCAC-3'

CT-B3:
(SEQ ID NO: 4)
5'-CCTCAGAAGTTTATGCACTTTC-3'

CT-LB:
(SEQ ID NO: 6)
5'-GGAGCGAGTTACGAAGACA-3'

<*Chlamydia trachomatis* TAMRA-labeled loop primer>
TAM-CT-LF:
(SEQ ID NO: 15)
5'-(TAMRA)-AAGATAACCCCGCACGT-3'

<*Chlamydia trachomatis* BHQ2-labeled quenching probe>
CT-LFc-Q2:
(SEQ ID NO: 16)
5'-GGGGTTATCTT-(BHQ2)-3'

(3) Synthesis of *Neisseria gonorrhoeae* Primer. FAM-Labeled Loop Primer (Fluorophore-Labeled Primer/Probe), and BHQ1-Labeled Quenching Probe (Quencher-Labeled Probe)

Primers were designed to target the *Neisseria gonorrhoeae* mtrA region and have no cross-reactivity with related bacteria. Primer synthesis was outsourced to Operon Biotechnologies Inc. The synthesis of the FAM-labeled loop primer and the BHQ1-labeled quenching probe was outsourced to Japan Bio Services Co., Ltd.

<*Neisseria gonorrhoeae* primer>
NG-FIP:
(SEQ ID NO: 17)
5'-CGTGGCTCAACACATGACCCAAGCGTCCGGTCGGCA-3'

NG-BIP:
(SEQ ID NO: 18)
5'-ACGGAGAAAGTTTACAACCGGACACAAAACAGGCTCATATCCAGC-3'

NG-F3:
(SEQ ID NO: 19)
5'-GCGGTTATCTCTGCATCG-3'

NG-B3:
(SEQ ID NO: 20)
5'-GGTGTCGTAGCGGAAAC-3'

NG-LF:
(SEQ ID NO: 22)
5'-CGGGAAAAATACAATATCGCCC-3'

-continued

<Neisseria gonorrhoeae FAM-labeled loop primer>
FAM-NG-LB:

(SEQ ID NO: 23)

5'-(FAM)-CGACAAAACGGCACATTTATGG-3'

<Neisseria gonorrhoeae BHQ1-labeled
quenching probe>
NG-LBc-Q1:

(SEQ ID NO: 24)

5'-CGTTTTGTCG-(BHQ1)-3'

(4) Composition and Concentration of LAMP Reaction Reagent

LAMP final reaction solutions were prepared such that each reagent had a concentration shown below in 30 μL each of the reaction solutions.

30 mM Tris-HCl (pH 8.8)

15 mM KCl 15 mM $(NH_4)_2SO_4$ 12 mM $MgSO_4$ 0.15% Tween 20

2.1 mM ATP 2.1 mM CTP 2.1 mM GTP 2.1 mM TTP 38.4 U Bst DNA polymerase (New England Biolabs Inc.)

*Chlamydia trachomatis* primer, TAMRA-labeled loop primer, and BHQ2-labeled quenching probe:

0.8 μM CT-FIP (SEQ ID NO: 1) and CT-BIP (SEQ ID NO: 2)

0.1 μM CT-F3 (SEQ ID NO: 3) and CT-B3 (SEQ ID NO: 4)

0.4 μM CT-LB (SEQ ID NO: 6) and TAM-CT-LF (SEQ ID NO: 15)

0.8 μM CT-LFc-Q2 (SEQ ED NO: 16)

*Neisseria gonorrhoeae* primer, FAM-labeled loop primer, and BHQ1-labeled quenching probe:

0.8 μM NG-FIP (SEQ ID NO: 17) and NG-BIP (SEQ ID NO: 18)

0.1 μM NG-F3 (SEQ ID NO: 19) and NG-B3 (SEQ ID NO: 20)

0.4 μM NG-LF (SEQ ID NO: 22) and FAM-NG-LB (SEQ ID NO: 23)

0.8 μM NG-LBc-Q1 (SEQ ID NO: 24)

(5) Amplification

DW, $10^4$ copies of CT plasmids, or $10^4$ copies of NG plasmids, or $10^4$ copies of CT plasmids and $10^4$ copies of NG plasmids were added per reaction. Amplification reaction was performed at 65° C. for 60 minutes using LA-320C.

(6) Determination

Figure 6:
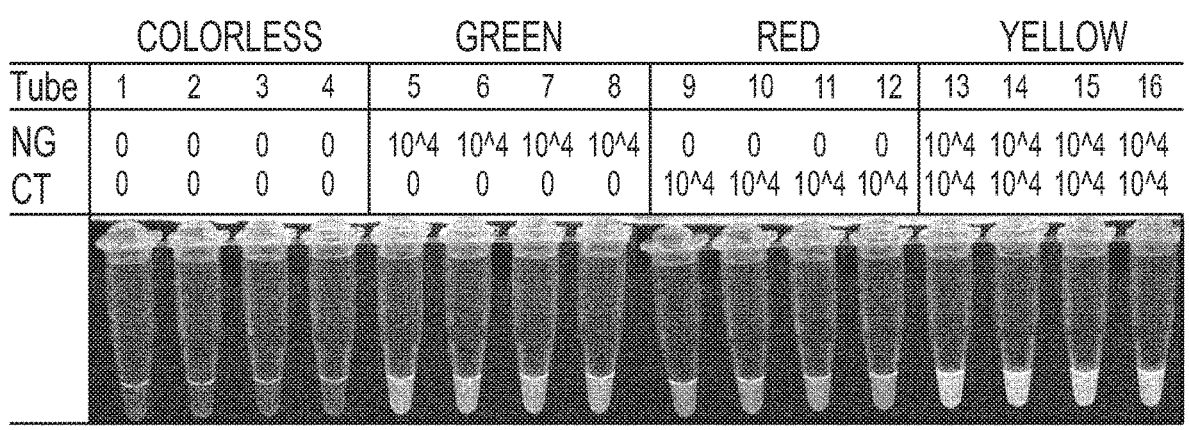
FIG. 6 shows results of discriminating standard reaction, *Chlamydia trachomatis*, and *Neisseria gonorrhoeae* in Example 3.

The amplification of the *Chlamydia trachomatis*-derived nucleic acid (CT) results in visually detectable red color (TAMRA) under UV irradiation, while the amplification of the *Neisseria gonorrhoeae*-derived nucleic acid (NG) results in visually detectable green color (FAM) under UV irradiation. After the amplification reaction, fluorescence was confirmed by UV irradiation. As a result (FIG. 6), DW (negative specimens) was colorless (Tube Nos. 1 to 4); green color was visually detected in the *Neisseria gonorrhoeae*-positive specimens (Tube Nos. 5 to 8); red color was visually detected in the *Chlamydia trachomatis*-positive specimens (Tube Nos. 9 to 12); and yellow (red+green) color was visually detected in the specimens positive for both bacteria (Tube Nos. 13 to 16).

Example 4

Multiple-Item Simultaneous Amplification and Detection of *Chlamydia trachomatis, Neisseria gonorrhoeae,* and Artificial Nucleic Acid (1) Assay Template A portion (SEQ ID NO: 21) of a *Chlamydia trachomatis* cryptic plasmid region was subcloned as a template for assay to prepare plasmid DNAs (hereinafter, referred to as CT plasmids). Also, a portion (SEQ ID NO: 32) of a *Neisseria gonorrhoeae* mtrA region was subcloned as a template for assay to prepare plasmid DNAs (hereinafter, referred to as NG plasmids). Further, an artificial nucleic acid sequence (SEQ ID NO: 33) was subcloned as a template for assay to prepare plasmid DNAs (hereinafter, referred to as ARITA2 plasmids).

(2) Synthesis of Primer, Fluorophore-Labeled Primer/Probe, and Quencher-Labeled Probe Primers for LAMP reaction were designed to target the *Chlamydia trachomatis* cryptic plasmid region, the *Neisseria gonorrhoeae* mtrA region, or the artificial nucleic acid sequence and have no cross-reactivity with related bacteria. Of the designed primers, *Chlamydia trachomatis* LF 5'-terminally fluorescently labeled with TAMRA, *Neisseria gonorrhoeae* LB 5'-terminally fluorescently labeled with FAM, and artificial nucleic acid sequence LB 5'-terminally fluorescently labeled with Alexa Fluor™ 350 (hereinafter, referred to as Alexa350) were used as fluorophore-labeled primers/probes, while a *Chlamydia trachomatis* LF-complementary strand 3'-terminally labeled with BHQ2, a *Neisseria gonorrhoeae* LB-complementary strand 3'-terminally labeled with BHQ1, and an artificial nucleic acid sequence LB-complementary strand 3'-terminally labeled with BHQ0 were used as quencher-labeled probes. Primer synthesis was outsourced to Operon Biotechnologies Inc. The synthesis of the fluorophore-labeled primers/probes and the quencher-labeled probes was outsourced to Japan Bio Services Co., Ltd.

<*Chlamydia trachomatis* primer>
CT-FIP:

(SEQ ID NO: 1)

5'-CAAGCAGGACTACAAGCTGCAGCGTTTGTACTCCGTCAC-3'

CT-BIP:

(SEQ ID NO: 2)

5'-GCGGGCGATTTGCCTTAACTCGGTCAACGAAGAGGTT-3'

CT-F3:

(SEQ ID NO: 3)

5'-ATGTCGGAGTCTGAGCAC-3'

CT-B3:

(SEQ ID NO: 4)

5'-CCTCAGAAGTTTATGCACTTTC-3'

CT-LB:

(SEQ ID NO: 6)

5'-GGAGCGAGTTACGAAGACA-3'

<*Chlamydia trachomatis* fluorophore-labeled primer/probe>
TAM-CT-LF:

(SEQ ID NO: 15)

5'-(TAMRA)-AAGATAACCCCGCACGT-3'

-continued

<Chlamydia trachomatis quencher-labeled probe>
CT-LFc-Q2:
(SEQ ID NO: 16)
5'-ACGTGCGGGGTTATCTT-(BHQ2)-3'

<Neisseria gonorrhoeae primer>
NG-FIP:
(SEQ ID NO: 17)
5'-CGTGGCTCAACACATGACCCAAGCGTCCGGTCGGCA-3'

NG-BIP:
(SEQ ID NO: 18)
5'-ACGGAGAAAGTTTACAACCGGACACAAAACAGGCTCATATCCAGC-3'

NG-F3:
(SEQ ID NO: 19)
5'-GCGGTTATCTCTGCATCG-3'

NG-B3:
(SEQ ID NO: 20)
5'-GGTGTCGTAGCGGAAAC-3'

NG-LF:
(SEQ ID NO: 22)
5'-CGGGAAAAATACAATATCGCCC-3'

<Neisseria gonorrhoeae fluorophore-labeled
primer/probe>
FAM-NG-LB:
(SEQ ID NO: 23)
5'-(FAM)-CGACAAAACGGCACATTTATGG-3'

<Neisseria gonorrhoeae quencher-labeled probe>
NG-LBc-Q1:
(SEQ ID NO: 24)
5'-CGTTTTGTCG-(BHQ1)-3'

<Artificial nucleic acid primer>
ARITA2-FIP:
(SEQ ID NO: 25)
5'-CGCTTGGATAGTCGGATGCAAGGGTCAATGGTAC-3'

ARITA2-BIP:
(SEQ ID NO: 26)
5'-ACGGTGTATGCTTCGGTGTGCGAACCTATCAGC-3'

ARITA2-F3:
(SEQ ID NO: 27)
5'-GGACAATCGAAGCCAGAA-3'

ARITA2-B3:
(SEQ ID NO: 28)
5'-ATCACGGATCGTATGTGG-3'

ARITA2-LF:
(SEQ ID NO: 29)
5'-GCTAGCTAAGTGCCATCC-3'

<Artificial nucleic acid fluorophore-labeled
primer/probe>
Ale-ARITA2-LB:
(SEQ ID NO: 30)
5'-(Alexa350)-AACGATCGCACTAAGCAT-3'

<Artificial nucleic acid quencher-labeled probe>
ARITA2-LBc-Q0:
(SEQ ID NO: 31)
5'-ATGCTTAGTGCGATCGTT-(BHQ0)-3'

(3) Composition and Concentration of LAMP Reaction Reagent

LAMP final reaction solutions were prepared such that each reagent had a concentration shown below in 30 μL each of the reaction solutions.

30 mM Tris-HCl (pH 8.8)
15 mM KCl
15 mM $(NH_4)_2SO_4$
12 mM $MgSO_4$
0.15% Tween 20
2.1 mM dATP (GeneACT, Inc.)
2.1 mM dCTP (GeneACT, Inc.)
2.1 mM dGTP (GeneACT, Inc.)
2.1 mM dTTP (GeneACT, Inc.)
38.4 U Bst DNA polymerase (New England Biolabs Inc.)
Primer and fluorophore-labeled primer/probe:
  0.6 μM CT-FIP (SEQ ID NO: 1), NG-FIP (SEQ ID NO: 17)
  0.6 μM CT-BIP (SEQ ID NO: 2), NG-BIP (SEQ ID NO: 18)
  0.1 μM CT-F3 (SEQ ID NO: 3), NG-F3 (SEQ ID NO: 19)
  0.1 μM CT-B3 (SEQ ID NO: 4), NG-B3 (SEQ ID NO: 20)
  0.3 μM CT-LB (SEQ ID NO: 6), NG-LF (SEQ ID NO: 22)
  0.1 μM ARITA2-FIP (SEQ ID NO: 25), ARITA2-BIP (SEQ ID NO: 26)
  0.02 μM ARITA2-F3 (SEQ ID NO: 27), ARITA2-B3 (SEQ ID NO: 28)
  0.1 μM ARITA2-LF (SEQ ID NO: 29)
  0.4 μM TAM-CT-LF (SEQ ID NO: 15), FAM-NG-LB (SEQ ID NO: 23), Ale-ARITA2-LB (SEQ ID NO: 30)

The following reagent was also added after amplification reaction.

Quencher-Labeled Probe:
  0.8 μM CT-LFc-Q2 (SEQ ID NO: 16), NG-LBc-Q1 (SEQ BD NO: 24), and ARITA2-LBc-Q0 (SEQ ID NO: 31)

(4) Amplification

DW or one or more of $10^4$ copies of CT plasmids, $10^4$ copies of NG plasmids, and $10^2$ copies of ARITA2 plasmids were added per reaction. Amplification reaction was performed at 65° C. for 120 minutes using LA-320C.

TABLE 3

Added template and amplification time

| Added template | | | | | | | | | |
|---|---|---|---|---|---|---|---|---|---|
| | CT | — | $10^4$ | — | — | $10^4$ | $10^4$ | — | $10^4$ |
| | NG | — | — | $10^4$ | — | $10^4$ | — | $10^4$ | $10^4$ |
| | ARITA2 | — | — | — | $10^2$ | — | $10^2$ | $10^2$ | $10^2$ |
| Tt | | N.D.* | 25.1 | 30.2 | 72.0 | 23.1 | 24.4 | 25.3 | 21.1 |

N.D.*: Not Detect (5) Determination

The amplification reaction was confirmed using LA-320C in the same way as in

Example 1

Figure 7:
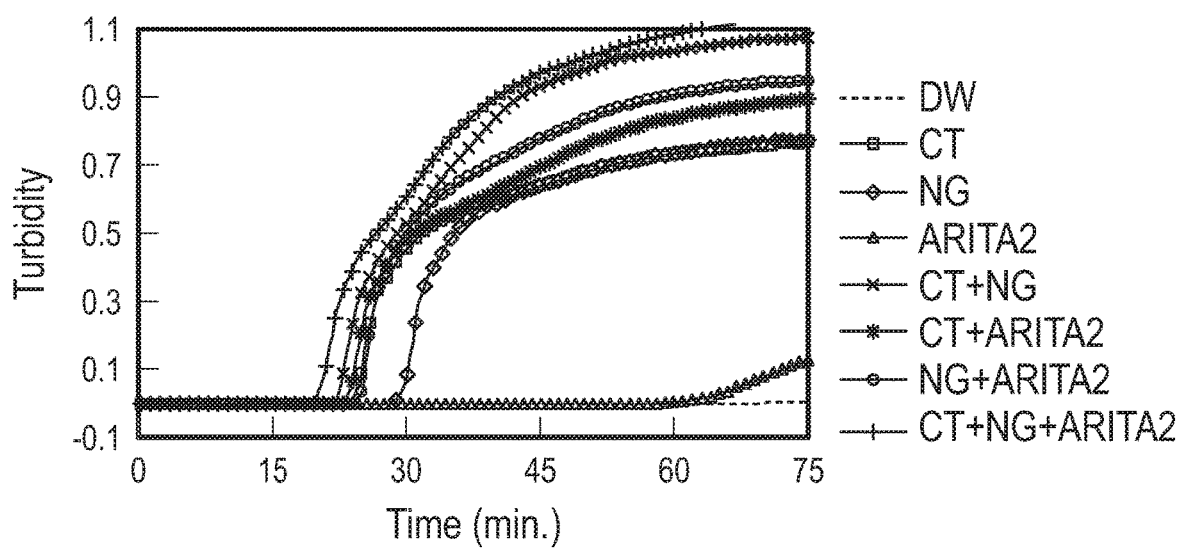
FIG. 7 shows the real-time turbidity curve of each target nucleic acid added in Example 4.

Table 3 and FIG. 7

Figure 8:
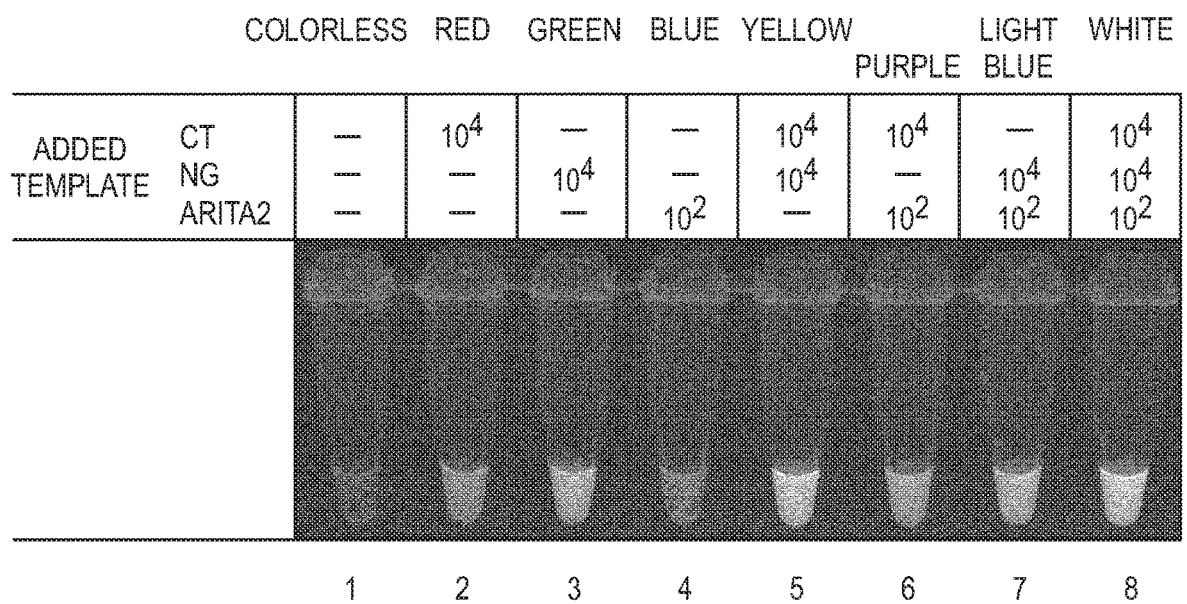
FIG. 8 shows reaction tubes irradiated with UV after amplification reaction and subsequent addition of quencher-labeled probes followed by heating at 95° C. for 5 minutes and then cooling to room temperature in Example 4.

No Tt value was detected and no rise in turbidity was seen in the reaction tube supplemented with DW (negative (−) for all CT, NG and ARITA2 plasmids). On the other hand, each Tt value was obtained and a rise in turbidity was confirmed in the reaction tubes supplemented with one, two in combination, or all three of the CT plasmids, the NG plasmids, and the ARITA2 plasmids. These results demonstrated that amplification reaction occurred only in the reaction tubes containing one or more of the CT plasmids, the NG plasmids, and the ARITA2 plasmids. 0.8 μM each of CT-LFc-Q2 (SEQ ID NO: 16), NG-LBc-Q1 (SEQ ID NO: 24), and ARITA2-LBc-Q0 (SEQ ID NO: 31) was added to each reaction tube after the completion of amplification. The reaction tubes were heated at 95° C. for 5 minutes, then cooled to room temperature, and then irradiated with UV to confirm fluorescence (FIG. 8).

No fluorescence was confirmed in the reaction tubes supplemented with DW, because of the absence of amplification products (Tube No. 1). Red fluorescence was confirmed in the reaction tube supplemented with the CT plasmids (Tube No. 2). Likewise, green fluorescence was confirmed in the reaction tube supplemented with the NG plasmids (Tube No. 3), while blue fluorescence was confirmed in the reaction tube supplemented with the ARITA2 plasmids (Tube No. 4). The reaction tubes supplemented with two of the plasmids exhibited color between their respective fluorescence colors. Yellow fluorescence was confirmed in the reaction tube supplemented with the CT plasmids and the NG plasmids (Tube No. 5). Purple fluorescence was confirmed in the reaction tube supplemented with the CT plasmids and the ARITA2 plasmids (Tube No. 6). Light blue fluorescence was confirmed in the reaction tube supplemented with the NG plasmids and the ARITA2 plasmids (Tube No. 7). White fluorescence was confirmed in the reaction tube supplemented with three of the plasmids (Tube No. 8).

Example 5

Detection of Target Nucleic Acid (*Chlamydia trachomatis*) Using Probe (1) Preparation of Sample LAMP reaction solutions after the amplification reaction were used as samples. As for LAMP reaction conditions, the composition and final concentration of each reagent were as shown below, and $10^4$ copies of CT plasmids were added as a template per reaction or DW was added instead of the template to prepare 30 µL each of LAMP final reaction solutions. Amplification reaction was performed at 65° C. for 40 minutes using LA-320C. The obtained reaction solutions were heat-treated at 80° C. for 5 minutes for inactivation of Bst DNA polymerase to prevent amplification reaction from occurring during subsequent detection using a fluorophore-labeled primer/probe. The LAMP reaction solutions, i.e., samples, thus obtained were defined as a positive specimen when prepared with the CT plasmids as a template or as a negative specimen when prepared by the addition of DW.

<Composition and Final Concentration of LAMP Reaction Reagent>

LAMP final reaction solutions were prepared such that each reagent had a concentration shown below in 30 µL each of the reaction solutions.

30 mM Tris-HCl (pH 8.8)
15 mM KCl
15 mM $(NH_4)_2SO_4$
12 mM $MgSO_4$
0.15% Tween 20
2.1 mM dATP (GeneACT, Inc.)
2.1 mM dCTP (GeneACT, Inc.)
2.1 mM dGTP (GeneACT, Inc.)
2.1 mM dTTP (GeneACT, Inc.)
38.4 U Bst DNA polymerase (New England Biolabs Inc.)

```
<Chlamydia trachomatis primer>
0.8 µM CT-FIP:
                                  (SEQ ID NO: 1)
5'-CAAGCAGGACTACAAGCTGCAGCGTTTGTACTCCGTCAC-3'

0.8 µM CT-BIP:
                                  (SEQ ID NO: 2)
5'-GCGGGCGATTTGCCTTAACTCGGTCAACGAAGAGGTT-3'

0.1 µM CT-F3:
                                  (SEQ ID NO: 3)
5'-ATGTCGGAGTCTGAGCAC-3'
```

```
0.1 µM CT-B3:
                                  (SEQ ID NO: 4)
5'-CCTCAGAAGTTTATGCACTTTC-3'

0.4 µM CT-FL:
                                  (SEQ ID NO: 5)
5'-AAGATAACCCCGCACGT-3'

0.4 µM CT-BL:
                                  (SEQ ID NO: 6)
5'-GGAGCGAGTTACGAAGACA-3'
```

(2) Synthesis of Fluorophore-Labeled Primer/Probe and Quencher-Labeled Probe

Of the designed primers, BL 5'-terminally fluorescently labeled with FAM was used as a fluorophore-labeled primer/probe, while its complementary strand 3'-terminally labeled with BHQ1 was used as a quencher-labeled probe. The synthesis of the fluorophore-labeled primer/probe and the quencher-labeled probe was outsourced to Japan Bio Services Co., Ltd.

```
<Chlamydia trachomatis fluorophore-labeled
primer/probe>
FAM-CT-BL:
                                  (SEQ ID NO: 7)
5'-(FAM)-GGAGCGAGTTACGAAGACA-3'

<Chlamydia trachomatis quencher-labeled probe>
CT-BLc-Q1-0:
                                  (SEQ ID NO: 8)
5'-TGTCTTCGTAACTCGCTCC-(BHQ1)-3'
```

(3) Addition of Fluorophore-Labeled Primer/Probe and Quencher-Labeled Probe to Sample 0.4 µM fluorophore-labeled primer/probe (SEQ ID NO: 7) was added to each of the positive specimen and the negative specimen prepared in the paragraph (1). The specimens were heat-treated at 95° C. for 5 minutes for denaturation of the template. Subsequently, the specimens were cooled to room temperature to anneal the fluorophore-labeled primer to the template.

Figure 9:
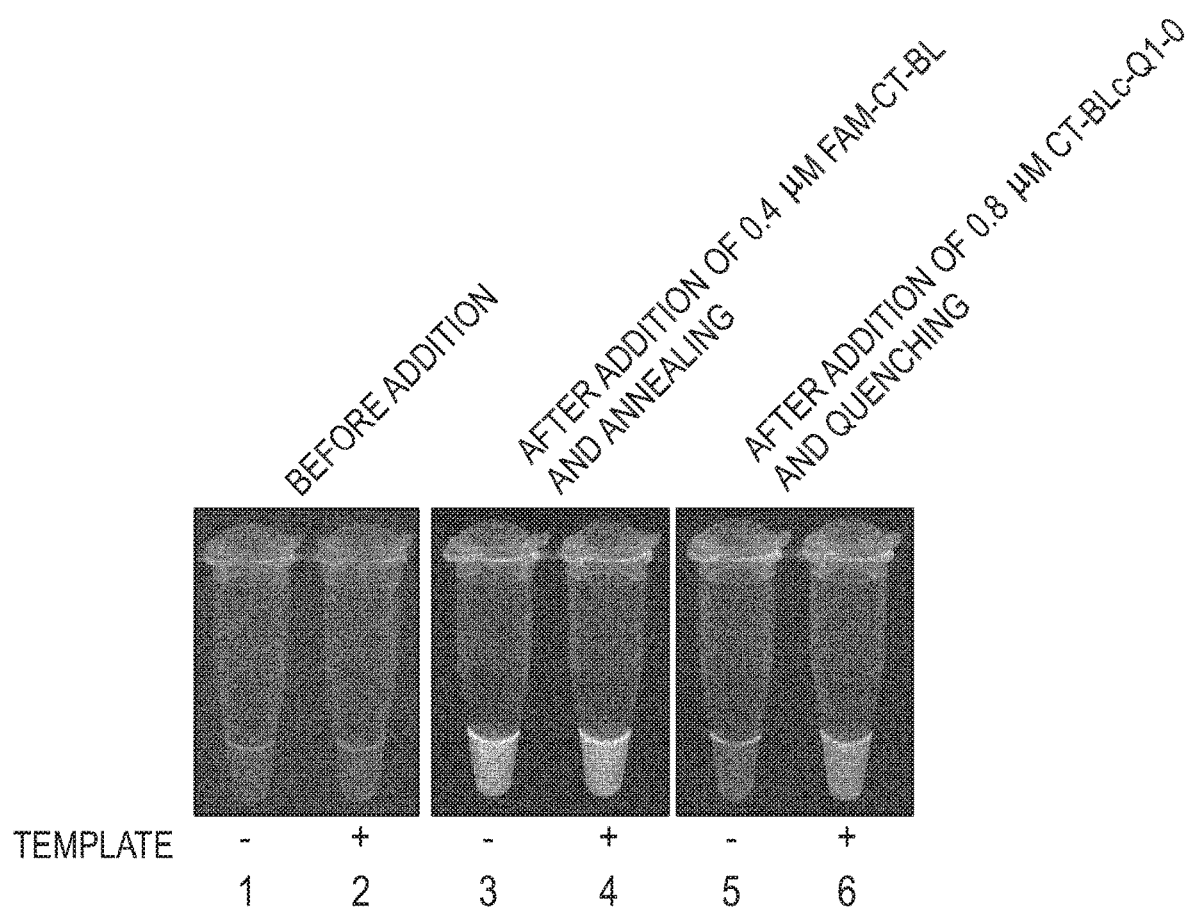
FIG. 9 shows reaction tubes irradiated with UV in Example 5.

After the cooling to room temperature, 0.8 µM quencher-labeled probe (SEQ ID NO: 8) was added thereto and stirred. Then, fluorescence from the specimens was confirmed under UV irradiation (FIG. 9).

(4) Determination

Fluorescence was detected neither in the positive specimen nor in the negative specimen before addition of the fluorophore-labeled primer/probe (Tube Nos. 1 and 2), and was detected after addition of the fluorophore-labeled primer/probe FAM-CT-BL (SEQ ID NO: 7) (Tube Nos. 3 and 4). These reaction tubes were heated at 95° C. for 5 minutes, then cooled to room temperature, and supplemented with the quencher-labeled probe CT-BLc-Q1-0 (SEQ ID NO: 8). Fluorescence was quenched in the negative specimen, because FAM-CT-BL (SEQ ID NO: 7) bound to CT-BLc-Q1-0 (SEQ ID NO: 8) in the absence of LAMP products (Tube No. 5). By contrast, fluorescence was retained in the positive specimen, because FAM-CT-BL (SEQ ID NO: 7) bound to LAMP products amplified with the CT plasmids as a template, without binding to CT-BLc-Q1-0 (SEQ ID NO: 8) (Tube No. 6).

Thus, Example 5 shows that the most basic aspect of the present invention shown in FIG. 1 can be carried out.

Example 6

Amplification and Detection of *Chlamydia trachomatis* Using Smart Amplification Process Version 2 (Hereinafter, Referred to as SMAP2) (Nucleic Acid Amplification and Detection of Amplification Product in Presence of Quencher-Labeled Probe in Isothermal Amplification Method SMAP2 Other than LAMP)

(1) Assay Template

A portion (SEQ ID NO: 21) of a *Chlamydia trachomatis* cryptic plasmid region was subcloned as a template for assay to prepare plasmid DNAs (hereinafter, referred to as CT plasmids).

(2) Synthesis of Primer, Fluorophore-Labeled Primer, and Quencher-Labeled Probe

Primers for SMAP2 reaction (a total of five primers: FP, TP, OP1, OP2, and BP) were designed to target a portion of the *Chlamydia trachomatis* cryptic plasmid region and have no cross-reactivity with related bacteria. Of the designed primers, a BP primer capable of being annealed to a loop moiety formed in amplification products by a TP primer was 5'-terminally fluorescently labeled with Alexa350 and used as a fluorophore-labeled primer/probe. A BP primer-complementary strand 3'-terminally labeled with BHQ0 was used as a quencher-labeled probe. Primer synthesis was outsourced to Operon Biotechnologies Inc. The synthesis of the fluorophore-labeled primer/probe and the quencher-labeled probe was outsourced to Japan Bio Services Co., Ltd.

```
<Chlamydia trachomatis SMAP2 primer>
CT-FP:
                                (SEQ ID NO: 34)
5'-TTTATATATATATAAAGCGTTTGTACTCCGTCAC-3'

CT-TP:
                                (SEQ ID NO: 35)
5'-GCGGGCGATTTGCCTTAACTCGGTCAACGAAGAGGTT-3'

CT-OP1:
                                (SEQ ID NO: 36)
5'-CCTCAGAAGTTTATGCACTTTC-3'

CT-OP2:
                                (SEQ ID NO: 37)
5'-ATGTCGGAGTCTGAGCAC-3'

<Chlamydia trachomatis fluorophore-labeled
primer/probe>
Ale-CT-BP:
                                (SEQ ID NO: 38)
5'-(Alexa350)-GGAGCGAGTTACGAAGACA-3'

<Chlamydia trachomatis quencher-labeled probe>
CT-BPc-Q0:
                                (SEQ ID NO: 39)
5'-AACTCGCTCC-(BHQ0)-3'
```

(3) Composition and Concentration of SMAP2 Reaction Reagent

SMAP2 final reaction solutions were prepared such that each reagent had a concentration shown below in 30 μL each of the reaction solutions.

30 mM Tris-HCl (pH 8.8)
15 mM KCl
15 mM $(NH_4)_2SO_4$
12 mM $MgSO_4$
0.15% Tween 20
2.1 mM dATP (GeneACT, Inc.)
2.1 mM dCTP (GeneACT, Inc.)
2.1 mM dGTP (GeneACT, Inc.)
2.1 mM dTTP (GeneACT, Inc.)
38.4 U Bst DNA polymerase (New England Biolabs Inc.)
Primer, Fluorophore-Labeled Primer/Probe, and Quencher-Labeled Probe:
  1.33 μM CT-FP (SEQ ID NO: 34)
  1.33 μM CT-TP (SEQ ID NO: 35)
  0.17 μM CT-OP1 (SEQ ID NO: 36)
  0.17 μM CT-OP2 (SEQ ID NO: 37)
  0.67 μM Ale-CT-BP (SEQ ID NO: 38)
  1.33 μM CT-BPc-Q0 (SEQ ID NO: 39)

(4) Amplification

DW or $10^6$ copies of CT plasmids were added per reaction. Amplification reaction was performed at 65° C. for 45 minutes using a real-time turbidimetric apparatus Loopamp EXIA™ (Teramecs Co., Ltd.).

(5) Determination

Figure 10:
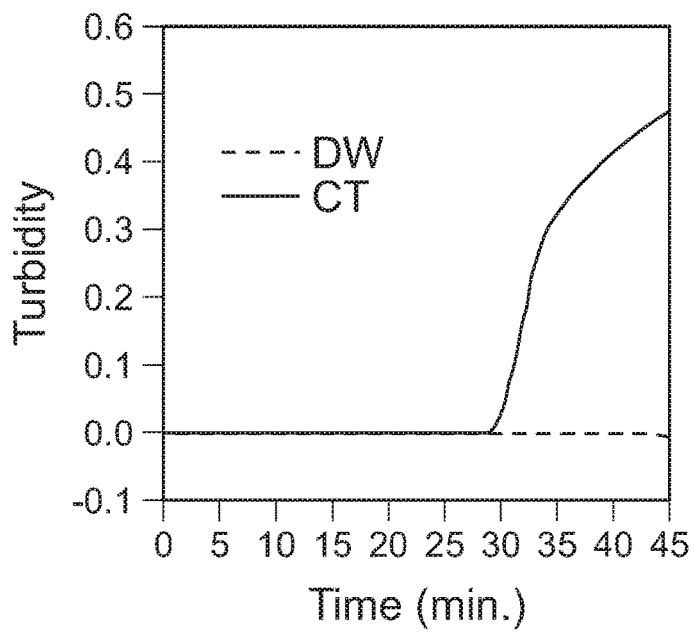
FIG. 10 shows the real-time turbidity curve of a target nucleic acid using fluorophore-labeled primers/probes and quencher-labeled probes in Example 6.

The amplification reaction was confirmed using Loopamp EXIA™ (Loopamp EXIA™ monitors nucleic acid amplification reaction on the basis of change in absorbance caused by the formation of its by-product magnesium pyrophosphate, i.e., change in turbidity; Tt value: time required for the arithmetic value of turbidimetry data to reach a determination value from the start of the reaction; turbidity curve: plot of the real-time assay data of turbidity) (Table 4 and FIG. 10).

No Tt value was detected and no rise in turbidity was seen in the reaction tube supplemented with DW. On the other hand, a Tt value of 23.2 minutes and a rise in turbidity were confirmed in the reaction tube supplemented with the CT plasmids. These results demonstrated that amplification reaction occurred only in the reaction tubes containing the CT plasmids, i.e., the target nucleic acid.

Figure 11:
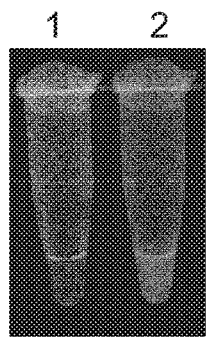
FIG. 11 shows reaction tubes irradiated with UV after amplification reaction in Example 6.

Each reaction tube was irradiated with UV after the completion of amplification reaction to observe fluorescence. As a result (FIG. 11), fluorescence was not observed in the reaction tube supplemented with DW (Tube No. 1), and was observed in the reaction tube supplemented with the CT plasmids (Tube No. 2).

Example 6 shows that the present invention can be carried out not only for the LAMP method but for various isothermal amplification reactions of nucleic acids.

TABLE 4

| Sample | Amplification time Tt |
|---|---|
| DW | N.D.* |
| CT | 23.2 |

*N.D.: Not Detect

Example 7

Detection of Fluorescence Wavelength in Single-Item Amplification or Two-Item or Three-Item Simultaneous Amplification Reaction System (1) Assay Template A portion (SEQ ID NO: 21) of a *Chlamydia trachomatis* cryptic plasmid region was subcloned as a template for assay to prepare plasmid DNAs (hereinafter, referred to as CT plasmids). Also, a portion (SEQ ID NO: 32) of a *Neisseria gonorrhoeae* mtrA region was subcloned as a template for assay to prepare plasmid DNAs (hereinafter, referred to as NG plasmids). Further, an artificial nucleic acid sequence (SEQ ID NO: 33) was subcloned as a template for assay to prepare plasmid DNAs (hereinafter, referred to as ARITA2 plasmids).

(2) Synthesis of Primer, Fluorophore-Labeled Primer/Probe, and Quencher-Labeled Probe Primers for LAMP reaction were designed to target the *Chlamydia trachomatis* cryptic plasmid region, the *Neisseria gonorrhoeae* mtrA region, or the artificial nucleic acid sequence and have no cross-reactivity with related bacteria. Of the designed primers, *Chlamydia trachomatis* BL 5'-terminally fluorescently labeled with Alexa350, *Neisseria gonorrhoeae* BL 5'-terminally fluorescently labeled with TAMRA, and artificial nucleic acid sequence BL 5'-terminally fluorescently labeled with FAM were used as fluorophore-labeled primers/probes, while a *Chlamydia trachomatis* BL-complementary strand 3'-terminally labeled with BHQ0, a *Neisseria gonorrhoeae* BL-complementary strand 3'-terminally labeled with BHQ2, and an artificial nucleic acid sequence BL-complementary strand 3'-terminally labeled with BHQ1 were used as quencher-labeled probes. Primer synthesis was outsourced to Operon Biotechnologies Inc. The synthesis of the fluorophore-labeled primers/probes and the quencher-labeled probes was outsourced to Japan Bio Services Co., Ltd.

```
<Chlamydia trachomatis primer>
CT-FLP:
                                              (SEQ ID NO: 1)
5'-CAAGCAGGACTACAAGCTGCAGCGTTTGTACTCCGTCAC-3'

CT-BIP:
                                              (SEQ ID NO: 2)
5'-GCGGGCGATTTGCCTTAACTCGGTCAACGAAGAGGTT-3'

CT-F3:
                                              (SEQ ID NO: 3)
5'-ATGTCGGAGTCTGAGCAC-3'

CT-B3:
                                              (SEQ ID NO: 4)
5'-CCTCAGAAGTTTATGCACTTTC-3'

CT-LF:
                                              (SEQ ID NO: 5)
5'-AAGATAACCCCGCACGT-3'

<Chlamydia trachomatis fluorophore-labeled
primer/probe>
Ale-CT-LB:
                                              (SEQ ID NO: 40)
5'-(Alexa350)-GGAGCGAGTTACGAAGACA-3'

<Chlamydia trachomatis quencher-labeled probe>
CT-LBc-Q0:
                                              (SEQ ID NO: 41)
5'-AACTCGCTCC-(BHQ0)-3'

<Neisseria gonorrhoeae primer>
NG-FIP:
                                              (SEQ ID NO: 17)
5'-CGTGGCTCAACACATGACCCAAGCGTCCGGTCGGCA-3'

NG-BIP:
                                              (SEQ ID NO: 18)
5'-ACGGAGAAAGTTTACAACCGGACACAAAACAGGCTCATATCCAGC-3'

NG-F3:
                                              (SEQ ID NO: 19)
5'-GCGGTTATCTCTGCATCG-3'

NG-B3:
                                              (SEQ ID NO: 20)
5'-GGTGTCGTAGCGGAAAC-3'

NG-LF:
                                              (SEQ ID NO: 22)
5'-CGGGAAAAATACAATATCGCCC-3'

<Neisseria gonorrhoeae fluorophore-labeled
primer/probe>
TAM-NG-LB:
                                              (SEQ ID NO: 42)
5'-(TAMRA)-CGACAAAACGGCACATTTATGG-3'

<Neisseria gonorrhoeae quencher-labeled probe>
NG-LBc-Q2:
                                              (SEQ ID NO: 43)
5'-CGTTTTGTCG-(BHQ2)-3'

<Artificial nucleic acid primer>
ARITA2-FIP:
                                              (SEQ ID NO: 25)
5'-CGCTTGGATAGTCGGATGCAAGGGTCAATGGTAC-3'

ARITA2-BIP:
                                              (SEQ ID NO: 26)
5'-ACGGTGTATGCTTCGGTGTGCGAACCTATCAGC-3'

ARITA2-F3:
                                              (SEQ ID NO: 27)
5'-GGACAATCGAAGCCAGAA-3'

ARITA2-B3:
                                              (SEQ ID NO: 28)
5'-ATCACGGATCGTATGTGG-3'

ARITA2-LF:
                                              (SEQ ID NO: 29)
5'-GCTAGCTAAGTGCCATCC-3'

<Artificial nucleic acid fluorophore-labeled
primer/probe>
FAM-ARITA2-LB:
                                              (SEQ ID NO: 44)
5'-(FAM)-AACGATCGCACTAAGCAT-3'

<Artificial nucleic acid quencher-labeled probe>
ARITA2-LBc-Q1:
                                              (SEQ ID NO: 45)
5'-ATGCTTAGTGCGATCGTT-(BHQ1)-3'
```

(3) Composition and Concentration of LAMP Reaction Reagent

LAMP final reaction solutions were prepared such that each reagent had a concentration shown below in 30 μL each of the reaction solutions.

30 mM Tris-HCl (pH 8.8)
15 mM KCl
15 mM $(NH_4)_2SO_4$
12 mM $MgSO_4$
0.15% Tween 20
2.1 mM ATP
2.1 mM CTP
2.1 mM GTP
2.1 mM TTP
38.4 U Bst DNA polymerase (New England Biolabs Inc.)

As for the primers, one or more form 3 sets each containing primers, fluorophore-labeled primers/probes, and quencher-labeled probes described below were added per reaction.

These sets each containing the primer, the fluorophore-labeled primer/probe, and the quencher-labeled probe were: 3 kinds for single-item amplification of *Chlamydia trachomatis, Neisseria gonorrhoeae*, and the artificial nucleic acid, respectively; 3 kinds for two-item simultaneous amplification of *Chlamydia trachomatis* and *Neisseria gonorrhoeae, Chlamydia trachomatis* and artificial nucleic acid, and *Neisseria gonorrhoeae* and artificial nucleic acid, respectively; and one kind for 3-item simultaneous amplification of *Chlamydia trachomatis*, *Neisseria gonorrhoeae*, and the artificial nucleic acid.

<*Chlamydia trachomatis* Primer, Fluorophore-Labeled Primer/Probe, and Quencher-Labeled Probe>
    0.67 μM CT-FIP (SEQ ID NO: 1)
    0.67 μM CT-BIP (SEQ ID NO: 2)
    0.17 μM CT-F3 (SEQ ID NO: 3)
    0.17 μM CT-B3 (SEQ ID NO: 4)
    0.33 μM CT-LF (SEQ ID NO: 5)
    0.67 μM Ale-CT-LB (SEQ ID NO: 40)
    1.33 μM CT-LBc-Q0 (SEQ ID NO: 41)

<*Neisseria gonorrhoeae* Primer, Fluorophore-Labeled Primer/Probe, and Quencher-Labeled Probe>
    1.20 μM NG-FIP (SEQ ID NO: 17)
    1.20 μM NG-BIP (SEQ ID NO: 18)
    0.17 μM NG-F3 (SEQ ID NO: 19)
    0.17 μM NG-B3 (SEQ ID NO: 20)
    0.67 μM NG-LF (SEQ ID NO: 22)
    0.67 μM TAM-NG-LB (SEQ ID NO: 42)
    1.33 μM NG-LBc-Q2 (SEQ ID NO: 43)

<Artificial Nucleic Acid Primer, Fluorophore-Labeled Primer/Probe, and Quencher-Labeled Probe>
    0.20 μM ARITA2-FIP (SEQ ID NO: 25)
    0.20 μM ARITA2-BIP (SEQ ID NO: 26)
    0.03 μM ARITA2-F3 (SEQ ID NO: 27)
    0.03 μM ARITA2-B3 (SEQ ID NO: 28)
    0.13 μM ARITA2-LF (SEQ ID NO: 29)
    0.67 μM FAM-ARITA2-LB (SEQ ID NO: 44)
    1.33 μM ARITA2-LBc-Q1 (SEQ ID NO: 45)

(4) Amplification

DW or one or more of $10^3$ copies of CT plasmids, $10^3$ copies of NG plasmids, and $10^3$ copies of ARITA2 plasmids were added per reaction. Amplification reaction was performed at 65° C. for 45 minutes using Loopamp EXIA™.

(5) Determination

Amplification reaction was confirmed using Loopamp EXIA™.

Each reaction tube was irradiated with UV after the completion of amplification reaction to observe fluorescence.

Also, each reaction solution after the amplification reaction was diluted 100-fold with a diluent and irradiated with excitation light corresponding to each fluorescent label using a spectrofluorophotometer RF-5300PC (manufactured by Shimadzu Corp.) to scan a fluorescence wavelength.

Figure 12:
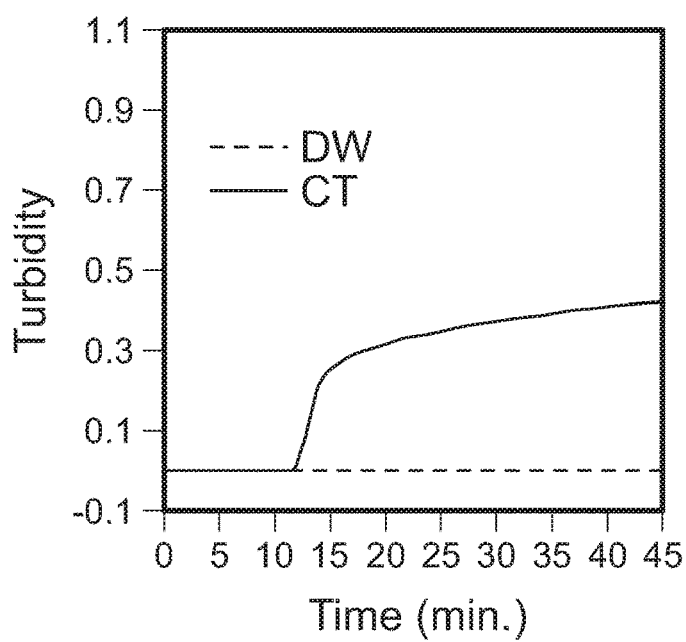
FIG. 12 shows a real-time turbidity curve from the single-item target nucleic acid amplification reaction of *Chlamydia trachomatis* using primers, fluorophore-labeled primers/probes, and quencher-labeled probes in Example 7.
Figure 13:
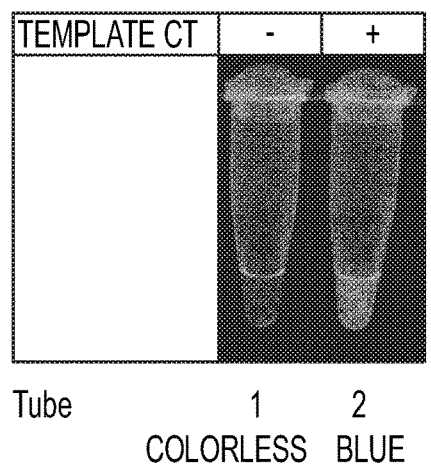
FIG. 13 shows reaction tubes irradiated with UV after the single-item target nucleic acid amplification reaction of *Chlamydia trachomatis* using primers, fluorophore-labeled primers/probes, and quencher-labeled probes in Example 7.
Figure 14A:
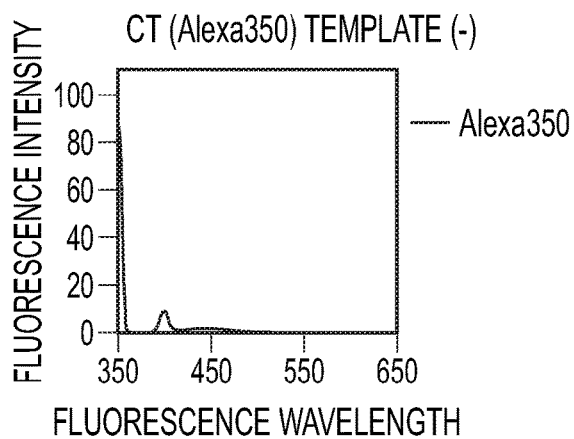
FIG. 14 shows a fluorescence wavelength after the single-item target nucleic acid amplification reaction of *Chlamydia trachomatis* using primers, fluorophore-labeled primers/probes, and quencher-labeled probes in Example 7.
Figure 14B:
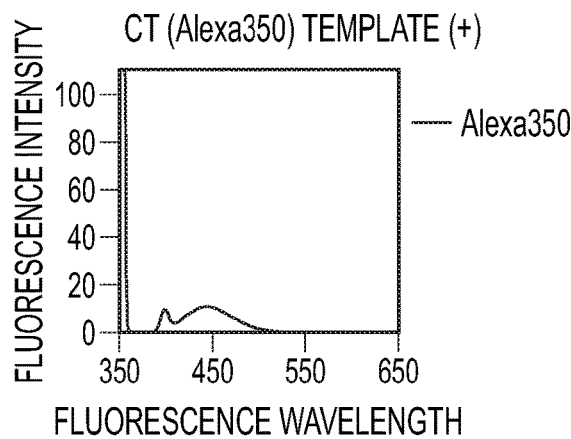

<Composition of Diluent>
    30 mM Tris-HCl, pH 8.8
    15 mM KCl
    15 mM $(NH_4)_2SO_4$
    12 mM $MgSO_4$ The following wavelength was used as the excitation light corresponding to each fluorescent label.
    Alexa350: 350 nm
    TAMRA: 555 nm
    FAM: 495 nm 1) Results of Measuring Fluorescence Wavelength after Amplification Reaction in Single-Item *Chlamydia trachomatis* Amplification Reaction System In the reaction tube supplemented with DW, no nucleic acid amplification was seen (Template CT "−" in Table 5 shows that no Tt value was detected; and the amplification curve of DW in FIG. 12 shows no rise in turbidity), and no fluorescence was confirmed under UV irradiation (Tube No. 1 in FIG. 13). In the reaction tube supplemented with the CT plasmids, nucleic acid amplification was seen (Template CT "+" in Table 5 shows a Tt value of 13.3 minutes; and the amplification curve of CT in FIG. 12 shows a rise in turbidity), and blue fluorescence presumably derived from Ale-CT-LB (SEQ ID NO: 40) was confirmed under UV irradiation (Tube No. 2 in FIG. 13). As for the fluorescence wavelength, likewise, only excitation light around 350 nm and a Raman spectral peak of water around 398 nm were confirmed in the template(−) (DW-supplemented) reaction solution irradiated with excitation light corresponding to Alexa350 (FIG. 14A). On the other hand, a fluorescence peak presumably derived from Ale-CT-LB was confirmed around 443 nm, in addition to excitation light around 350 nm and a Raman spectral peak of water around 398 nm, in the template(+) (CT plasmid-supplemented) reaction solution (FIG. 14B).

TABLE 5

| | Added template and amplification time | |
|---|---|---|
| Template CT | − | + |
| Tt | N.D.* | 13.3 |

*N.D.: Not Detect

Figure 15:
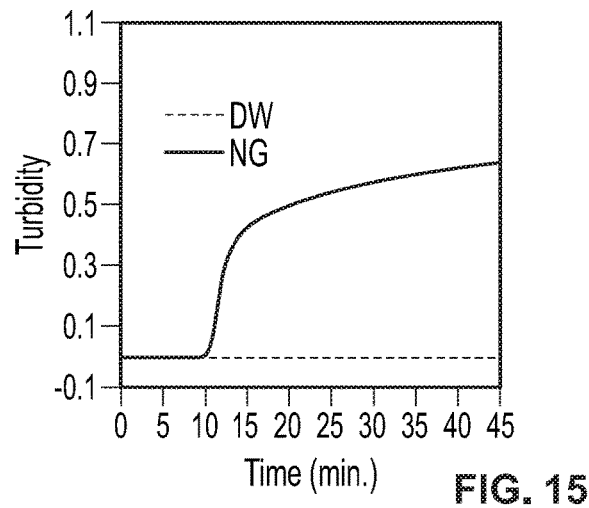
FIG. 15 shows a real-time turbidity curve from the single-item target nucleic acid amplification reaction of *Neisseria gonorrhoeae* using primers, fluorophore-labeled primers/probes, and quencher-labeled probes in Example 7.
Figure 16:
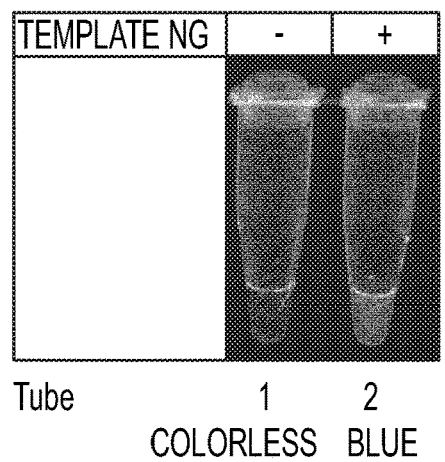
FIG. 16 shows reaction tubes irradiated with UV after the single-item target nucleic acid amplification reaction of *Neisseria gonorrhoeae* using primers, fluorophore-labeled primers/probes, and quencher-labeled probes in Example 7.
Figure 17A:
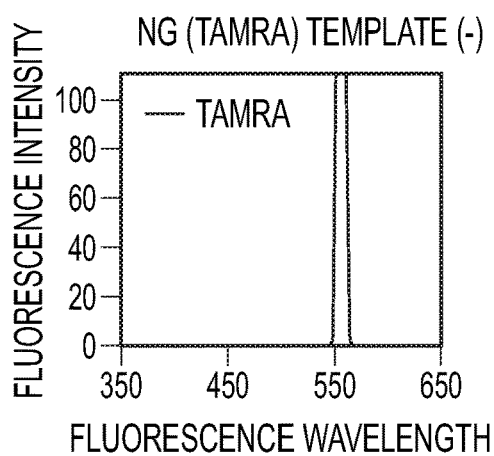
FIG. 17 shows a fluorescence wavelength after the single-item target nucleic acid amplification reaction of *Neisseria gonorrhoeae* using primers, fluorophore-labeled primers/probes, and quencher-labeled probes in Example 7.
Figure 17B:
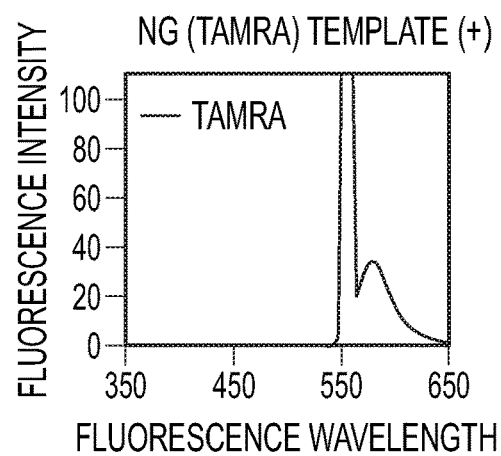

2) Results of Measuring Fluorescence Wavelength After Amplification Reaction in Single-Item *Neisseria gonorrhoeae* Amplification Reaction System In the reaction tube supplemented with DW, no nucleic acid amplification was seen (Template NG "−" in Table 6 shows that no Tt value was detected; and the amplification curve of DW in FIG. 15 shows no rise in turbidity), and no fluorescence was confirmed under UV irradiation (Tube No. 1 in FIG. 16). In the reaction tube supplemented with the NG plasmids, nucleic acid amplification was seen (Template NG "+" in Table 6 shows a Tt value of 11.6 minutes; and the amplification curve of NG in FIG. 15 shows a rise in turbidity), and red fluorescence presumably derived from TAM-NG-LB (SEQ ID NO: 42) was confirmed under UV irradiation (Tube No. 2 in FIG. 16). As for the fluorescence wavelength, likewise, only excitation light around 555 nm was confirmed in the template(−) (DW-supplemented) reaction solution irradiated with excitation light corresponding to TAMRA (FIG. 17A). On the other hand, excitation light around 555 nm and a fluorescence peak presumably derived from TAM-NG-LB around 580 nm were confirmed in the template(+) (NG plasmid-supplemented) reaction solution (FIG. 17B).

TABLE 6

| | Added template and amplification time | |
|---|---|---|
| Template NG | − | + |
| Tt | N.D.* | 11.6 |

*N.D.: Not Detect

Figure 18:
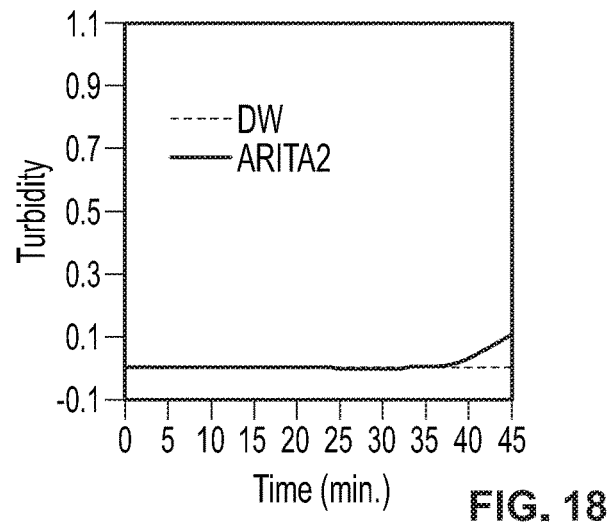
FIG. 18 shows a real-time turbidity curve from the single-item target nucleic acid amplification reaction of an artificial nucleic acid using primers, fluorophore-labeled primers/probes, and quencher-labeled probes in Example 7.
Figure 19:
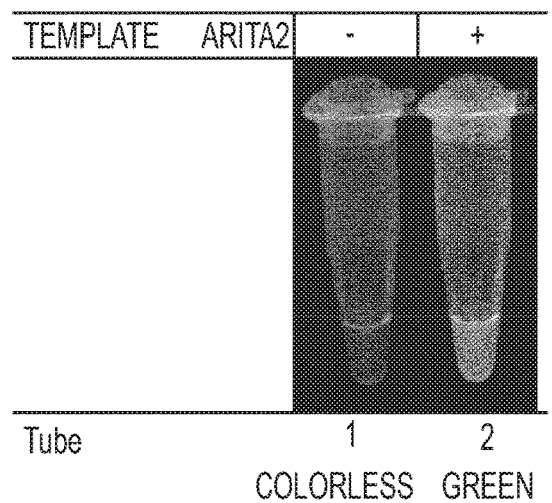
FIG. 19 shows reaction tubes irradiated with UV after the single-item target nucleic acid amplification reaction of *Neisseria gonorrhoeae* using primers, fluorophore-labeled primers/probes, and quencher-labeled probes in Example 7.

3) Results of Measuring Fluorescence Wavelength after Amplification Reaction in Single-Item Artificial Nucleic Acid Amplification Reaction System In the reaction tube supplemented with DW, no nucleic acid amplification was seen (Template ARITA2 "−" in Table 7 shows that no Tt value was detected; and the amplification curve of DW in FIG. 18 shows no rise in turbidity), and no fluorescence was confirmed under UV irradiation (Tube No. 1 in FIG. 19). In the reaction tube supplemented with the ARITA2 plasmids, nucleic acid amplification was seen (Template ARITA2 "+" in Table 7 shows that a Tt value was not detected within the reaction time, but the amplification curve of ARITA2 in FIG. 18 shows a rise in turbidity; thus, it was concluded that the nucleic acid was amplified), and green fluorescence presumably derived from FAM-ARITA2-LB (SEQ ID NO: 44) was confirmed under UV irradiation (Tube No. 2 in FIG. 19).

Figure 20A:
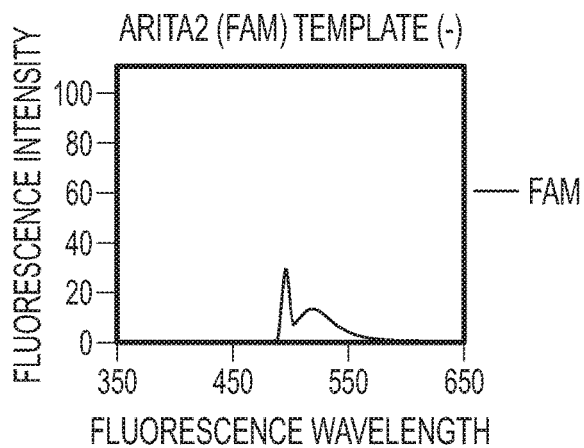
FIG. 20 shows a fluorescence wavelength after the single-item target nucleic acid amplification reaction of an artificial nucleic acid using primers, fluorophore-labeled primers/probes, and quencher-labeled probes in Example 7.
Figure 20B:
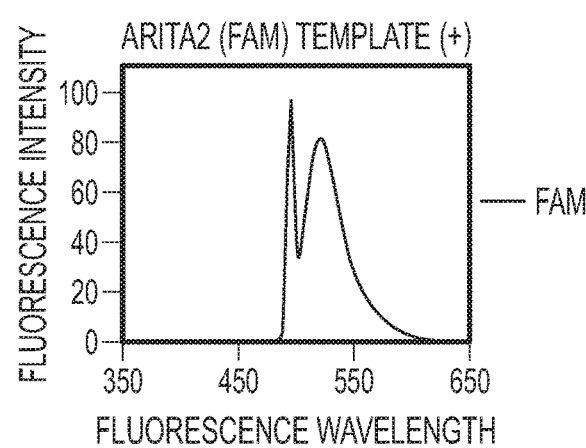

As for the fluorescence wavelength, excitation light around 495 nm and a fluorescence peak presumably derived from FAM-ARITA2-LB around 522 nm were seen both in the template(−) (DW-supplemented) reaction solution (FIG. 20A) and in the template(+) (ARITA2 plasmid-supplemented) reaction solution (FIG. 20B) irradiated with excitation light corresponding to FAM. However, a smaller (fluorescence intensity: less than 20) peak (background) was confirmed in the template(−) reaction solution, whereas a larger (fluorescence intensity: more than 80) peak was confirmed in the template(+) reaction solution.

TABLE 7

| Added template and amplification time | | |
|---|---|---|
| Template ARITA2 | − | + |
| Tt | N.D.* | N.D.* |

*N.D.: Not Detect

4) Results of Measuring Fluorescence Wavelength after Amplification Reaction in Two-Item Simultaneous Amplification Reaction System of *Chlamydia trachomatis* and *Neisseria gonorrhoeae*

Figure 21:
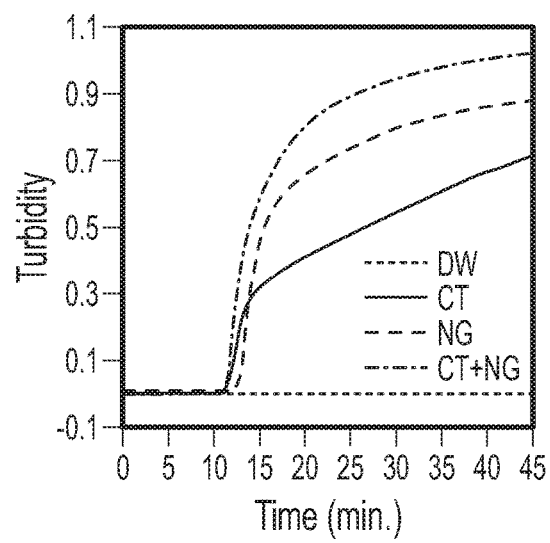
FIG. 21 shows a real-time turbidity curve from the two-item target nucleic acid amplification reaction of *Chlamydia trachomatis* and *Neisseria gonorrhoeae* using primers, fluorophore-labeled primers/probes, and quencher-labeled probes in Example 7.
Figure 22:
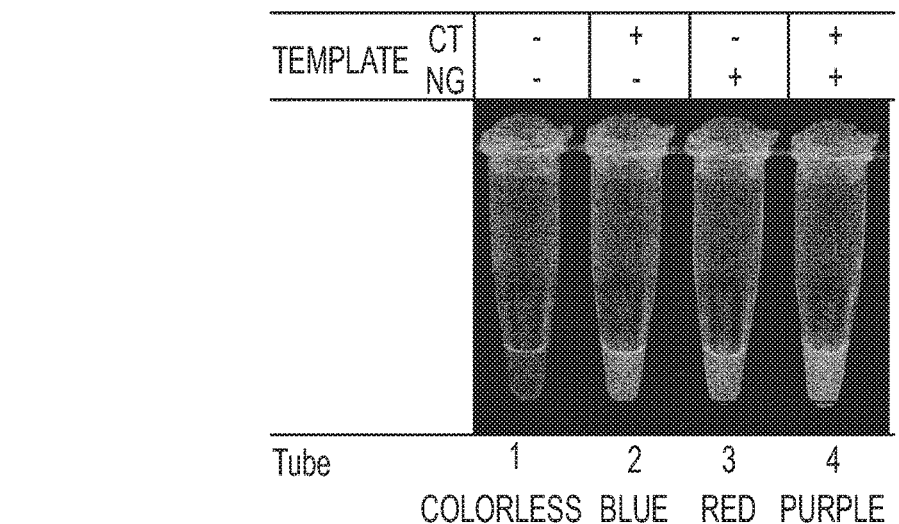
FIG. 22 shows reaction tubes irradiated with UV after the two-item target nucleic acid amplification reaction of *Chlamydia trachomatis* and *Neisseria gonorrhoeae* using primers, fluorophore-labeled primers/probes, and quencher-labeled probes in Example 7.

In the reaction tube supplemented with DW, no nucleic acid amplification was seen (Template CT "−" and NG "−" in Table 8 show that no Tt value was detected; and the amplification curve of DW in FIG. 21 shows no rise in turbidity), and no fluorescence was confirmed under UV irradiation (Tube No. 1 in FIG. 22). In the reaction tube supplemented with only the CT plasmids, only the NG plasmids, or the CT plasmids and the NG plasmids, nucleic acid amplification was seen (Template CT "+" and NG "−", Template NG "+" and CT "−", and Template CT "+" and NG "+" in Table 8 show Tt values of 12.8 minutes, 13.6 minutes, and 12.2 minutes, respectively; and the amplification curves of CT, NG, and CT+NG in FIG. 21 show a rise in turbidity), and blue fluorescence (Tube No. 2 in FIG. 22) presumably derived from Ale-CT-LB (SEQ ID NO: 40), red fluorescence (Tube No. 3 in FIG. 22) presumably derived from TAM-NG-LB (SEQ ID NO: 42), and purple fluorescence (Tube No. 4 in FIG. 22) presumably derived from Ale-CT-LB and TAM-NG-LB were respectively confirmed under UV irradiation.

Figure 23A:
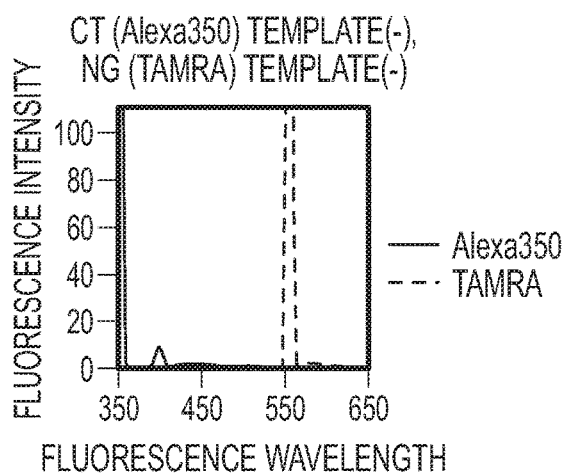
FIG. 23 shows a fluorescence wavelength after the two-item target nucleic acid amplification reaction of *Chlamydia trachomatis* and *Neisseria gonorrhoeae* using primers, fluorophore-labeled primers/probes, and quencher-labeled probes in Example 7.

As for the fluorescence wavelength, excitation light around 350 nm and a Raman spectral peak of water around 398 nm were confirmed in the CT and NG template(−) (DW-supplemented) reaction solution (FIG. 23A) irradiated with excitation light corresponding to Alexa350, while only excitation light around 555 nm was confirmed in this reaction solution irradiated with excitation light corresponding to TAMRA.

Figure 23B:
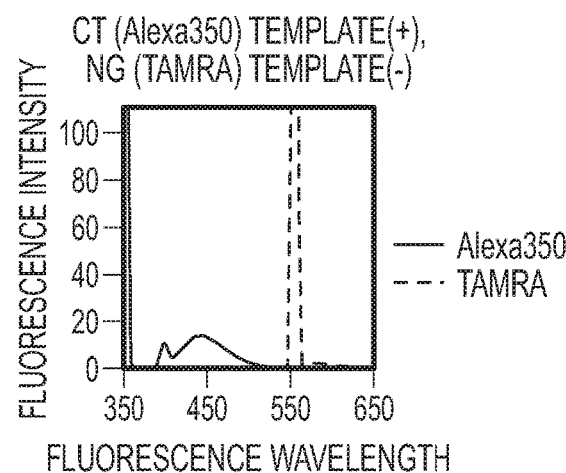

A fluorescence peak presumably derived from Ale-CT-LB was confirmed around 443 nm, in addition to excitation light around 350 nm and a Raman spectral peak of water around 398 nm, in the CT template(+) and NG template(−) (CT plasmid-supplemented and NG plasmid-unsupplemented) reaction solution (FIG. 23B) irradiated with excitation light corresponding to Alexa350, while only excitation light around 555 nm was confirmed in this reaction solution irradiated with excitation light corresponding to TAMRA.

Figure 23C:
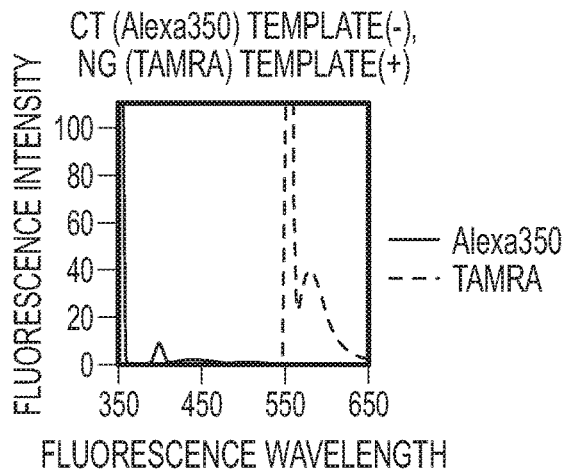

Only excitation light around 350 nm and a Raman spectral peak of water around 398 nm were confirmed in the NG template(+) and CT template(−) (NG plasmid-supplemented and CT plasmid-unsupplemented) reaction solution (FIG. 23C) irradiated with excitation light corresponding to Alexa350, while excitation light around 555 nm and a fluorescence peak presumably derived from TAM-NG-LB around 580 nm were confirmed in this reaction solution irradiated with excitation light corresponding to TAMRA.

Figure 23D:
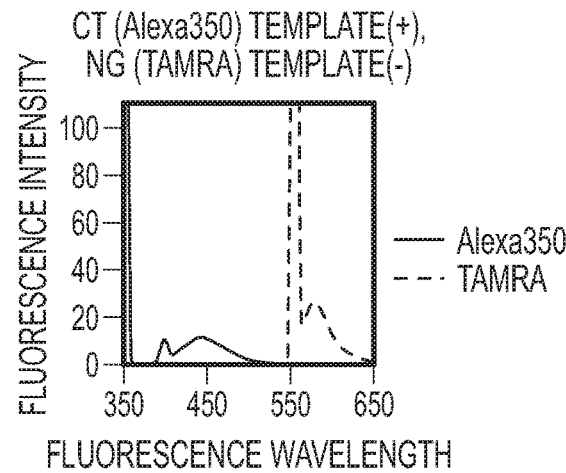

A fluorescence peak presumably derived from Ale-CT-LB was confirmed around 443 nm, in addition to excitation light for Alexa350 around 350 nm and a Raman spectral peak of water around 398 nm, in the CT and NG template(+) (CT plasmid-supplemented and NG plasmid-supplemented) reaction solution (FIG. 23D) irradiated with excitation light corresponding to Alexa350, while excitation light around 555 nm and a fluorescence peak presumably derived from TAM-NG-LB around 580 nm were confirmed in this reaction solution irradiated with excitation light corresponding to TAMRA.

TABLE 8

| | | Added template and amplification time | | | |
|---|---|---|---|---|---|
| Template | CT | − | + | − | + |
| | NG | − | − | + | + |
| | Tt | N.D.* | 12.8 | 13.6 | 12.2 |

*N.D.: Not Detect

Figure 24:
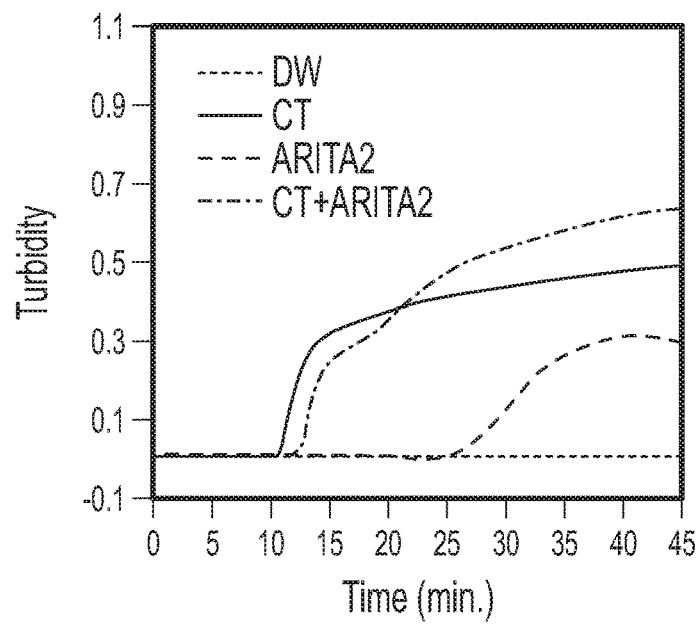
FIG. 24 shows a real-time turbidity curve from the two-item target nucleic acid amplification reaction of *Chlamydia trachomatis* and an artificial nucleic acid using primers, fluorophore-labeled primers/probes, and quencher-labeled probes in Example 7.
Figure 25:
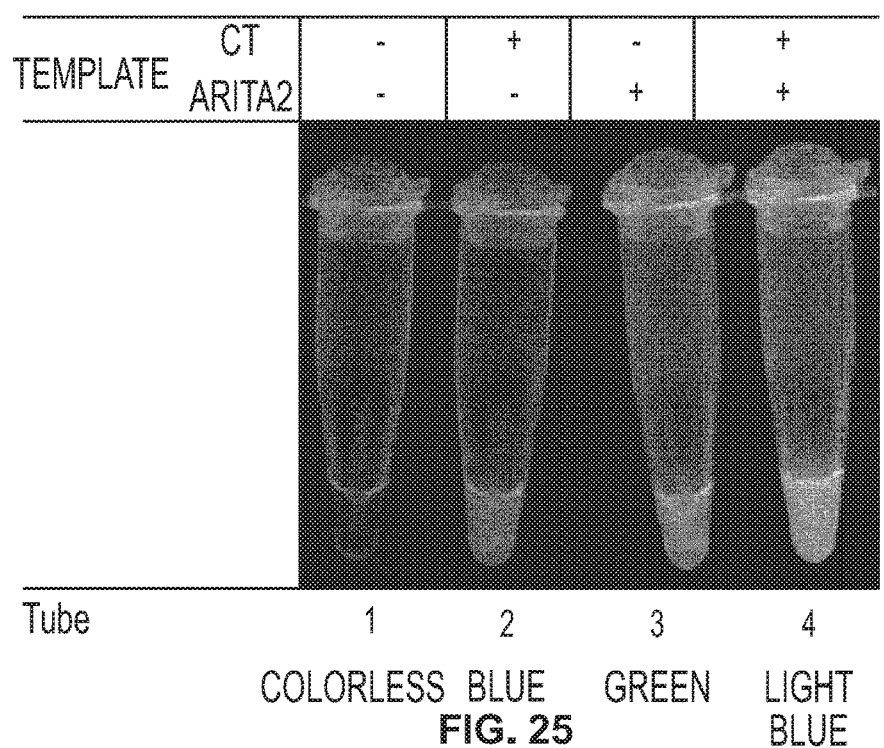
FIG. 25 shows reaction tubes irradiated with UV after the two-item target nucleic acid amplification reaction of *Chlamydia trachomatis* and an artificial nucleic acid using primers, fluorophore-labeled primers/probes, and quencher-labeled probes in Example 7.

5) Results of Measuring Fluorescence Wavelength after Amplification Reaction in Two-Item Simultaneous Amplification Reaction System of *Chlamydia trachomatis* and Artificial Nucleic Acid In the reaction tube supplemented with DW, no nucleic acid amplification was seen (Template CT "−" and ARITA2 "−" in Table 9 show that no Tt value was detected; and the turbidity curve of DW in FIG. 24 shows no rise in turbidity), and no fluorescence was confirmed under UV irradiation (Tube No. 1 in FIG. 25). In the reaction tube supplemented with only the CT plasmids, only the ARITA2 plasmids, or the CT plasmids and the ARITA2 plasmids, nucleic acid amplification was seen (Template CT "+" and ARITA2 "−", Template ARITA2 "+" and CT "−", and Template CT "+" and ARITA2 "+" in Table 9 show Tt values of 12.0 minutes, 28.2 minutes, and 13.6 minutes, respectively; and the turbidity curves of CT, ARITA2, and CT+ARITA2 in FIG. 24 show a rise in turbidity), and blue fluorescence (Tube No. 2 in FIG. 25) presumably derived from Ale-CT-LB (SEQ ID NO: 40), green fluorescence (Tube No. 3 in FIG. 25) presumably derived from FAM-ARITA2-LB (SEQ ID NO: 44), and light blue fluorescence (Tube No. 4 in FIG. 25) presumably derived from Ale-CT-LB and FAM-ARITA2-LB were respectively confirmed under UV irradiation.

Figure 26A:
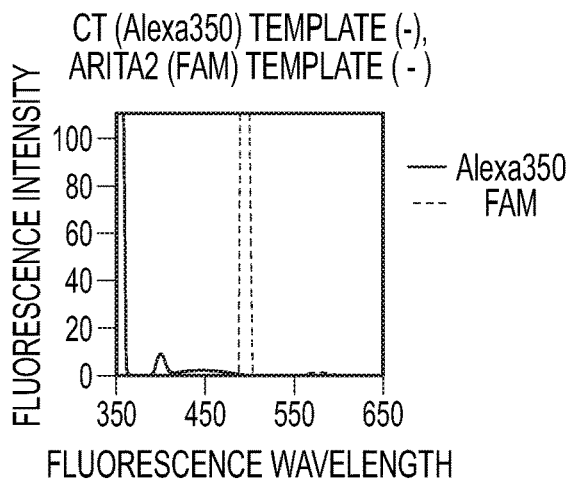
FIG. 26 shows a fluorescence wavelength after the two-item target nucleic acid amplification reaction of *Chlamydia trachomatis* and an artificial nucleic acid using primers, fluorophore-labeled primers/probes, and quencher-labeled probes in Example 7.

As for the fluorescence wavelength, excitation light around 350 nm and a Raman spectral peak of water around 398 nm were confirmed in the CT and ARITA2 template(−) (DW-supplemented) reaction solution (FIG. 26A) irradiated with excitation light corresponding to Alexa350, while only excitation light around 495 nm was confirmed in this reaction solution irradiated with excitation light corresponding to FAM.

Figure 26B:
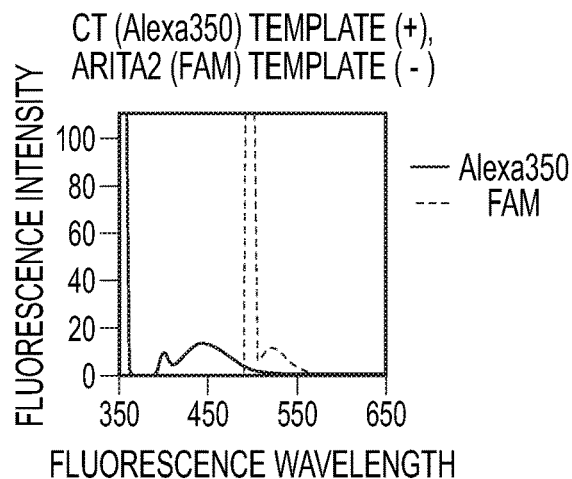

A fluorescence peak presumably derived from Ale-CT-LB was confirmed around 443 nm, in addition to excitation light around 350 nm and a Raman spectral peak of water around 398 nm, in the CT template(+) and ARITA2 template(−) (CT plasmid-supplemented and ARITA2 plasmid-unsupplemented) reaction solution (FIG. 26B) irradiated with excitation light corresponding to Alexa350, while excitation light around 495 nm and a small (fluorescence intensity: less than 20) peak (background) of fluorescence presumably derived from FAM-ARITA2-LB around 522 nm were confirmed in this reaction solution irradiated with excitation light corresponding to FAM.

Figure 26C:
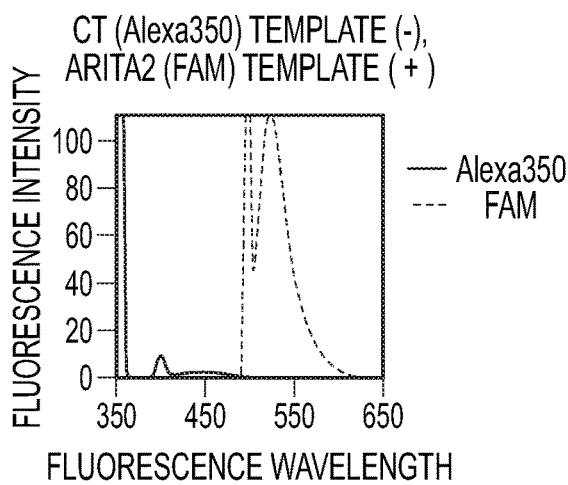

Only excitation light around 350 nm and a Raman spectral peak of water around 398 nm were confirmed in the ARITA2 template(+) and CT template(−) (ARITA2 plasmid-supplemented and CT plasmid-unsupplemented) reaction solution (FIG. 26C) irradiated with excitation light corresponding to Alexa350, while excitation light around 495 nm and a sufficiently large (fluorescence intensity: more than 80) peak of fluorescence presumably derived from FAM-ARITA2-LB around 522 nm were confirmed in this reaction solution irradiated with excitation light corresponding to FAM.

Figure 26D:
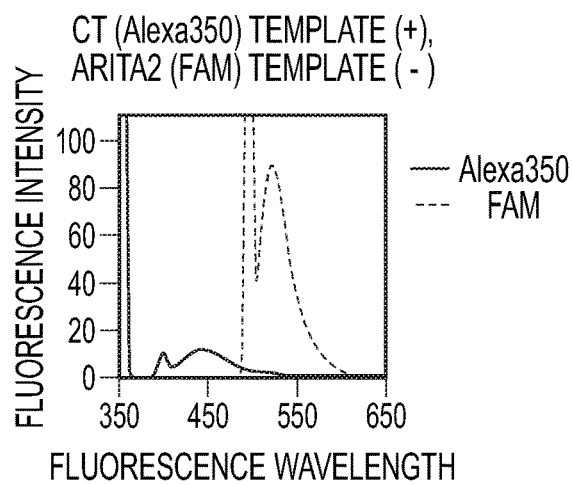

A fluorescence peak presumably derived from Ale-CT-LB was confirmed around 443 nm, in addition to excitation light around 350 nm and a Raman spectral peak of water around 398 nm, in the CT and ARITA template(+) (CT plasmid-supplemented and ARITA2 plasmid-supplemented) reaction solution (FIG. 26D) irradiated with excitation light corresponding to Alexa350, while excitation light around 495 nm and a sufficiently large (fluorescence intensity: more than 80) peak of fluorescence presumably derived from FAM-ARITA2-LB around 522 nm were confirmed in this reaction solution irradiated with excitation light corresponding to FAM.

TABLE 9

| Added template and amplification time | | | | | |
|---|---|---|---|---|---|
| Template | CT | − | + | − | + |
| | ARITA2 | − | − | + | + |
| | Tt | N.D.* | 12.0 | 28.2 | 13.6 |

*N.D.: Not Detect

Figure 27:
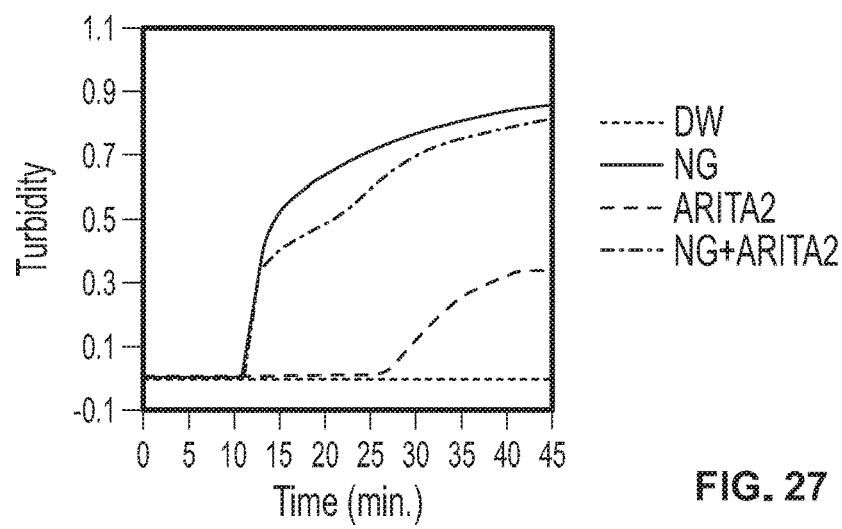
FIG. 27 shows a real-time turbidity curve from the two-item target nucleic acid amplification reaction of *Neisseria gonorrhoeae* and an artificial nucleic acid using primers, fluorophore-labeled primers/probes, and quencher-labeled probes in Example 7.
Figure 28:
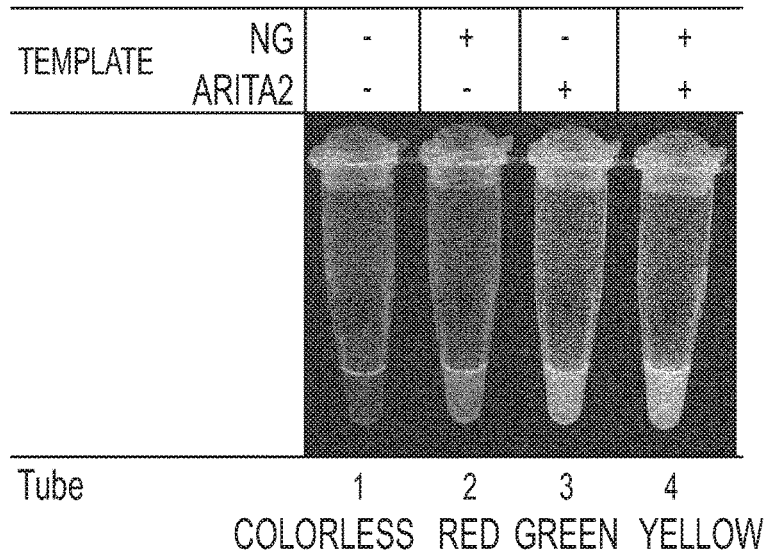
FIG. 28 shows reaction tubes irradiated with UV after the two-item target nucleic acid amplification reaction of *Neisseria gonorrhoeae* and an artificial nucleic acid using primers, fluorophore-labeled primers/probes, and quencher-labeled probes in Example 7.

6) Results of Measuring Fluorescence Wavelength after Amplification Reaction in Two-Item Simultaneous Amplification Reaction System of *Neisseria gonorrhoeae* and Artificial Nucleic Acid In the reaction tube supplemented with DW, no nucleic acid amplification was seen (Template NG "−" and ARITA2 "−" in Table 10 show that no Tt value was detected; and the turbidity curve of DW in FIG. 27 shows no rise in turbidity), and no fluorescence was confirmed under UV irradiation (Tube No. 1 in FIG. 28). In the reaction tube supplemented with only the NG plasmids, only the ARITA2 plasmids, or the NG plasmids and the ARITA2 plasmids, nucleic acid amplification was seen (Template NG "+" and ARITA2 "−", Template ARITA2 "+" and NG "−", and Template NG "+" and ARITA2 "+" in Table 10 show Tt values of 12.0 minutes, 29.0 minutes, and 11.9 minutes, respectively; and the turbidity curves of NG, ARITA2, and NG+ARITA2 in FIG. 27 show a rise in turbidity), and red fluorescence (Tube No. 2 in FIG. 28) presumably derived from TAM-NG-LB (SEQ ID NO: 42), green fluorescence (Tube No. 3 in FIG. 28) presumably derived from FAM-ARITA2-LB (SEQ ID NO: 44), and yellow fluorescence (Tube No. 4 in FIG. 28) presumably derived from TAM-NG-LB and FAM-ARITA2-LB were respectively confirmed under UV irradiation.

Figure 29A:
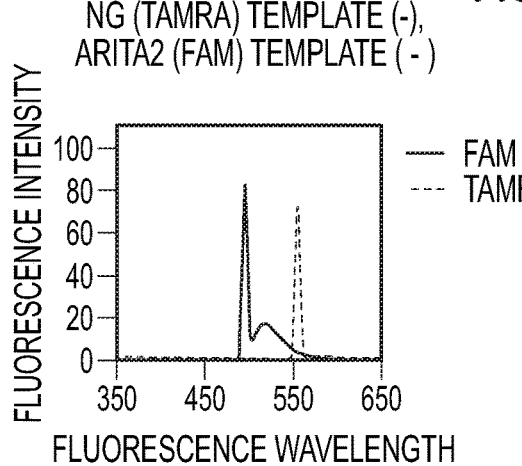
FIG. 29 shows a fluorescence wavelength after the two-item target nucleic acid amplification reaction of *Neisseria gonorrhoeae* and an artificial nucleic acid using primers, fluorophore-labeled primers/probes, and quencher-labeled probes in Example 7.

As for the fluorescence wavelength, excitation light around 555 nm was confirmed in the NG and ARITA2 template(−) (DW-supplemented) reaction solution (FIG. 29A) irradiated with excitation light corresponding to TAMRA, while excitation light around 495 nm and a small (fluorescence intensity: less than 20) peak (background) of fluorescence presumably derived from FAM-ARITA2-LB around 522 nm were confirmed in this reaction solution irradiated with excitation light corresponding to FAM.

Figure 29B:
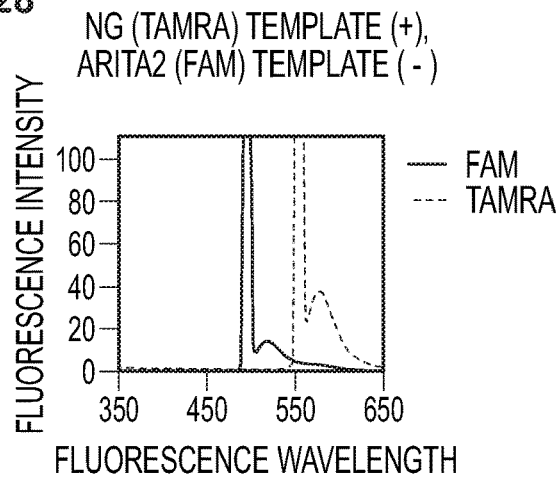

Excitation light around 555 nm and a fluorescence peak presumably derived from TAM-NG-LB around 580 nm were confirmed in the NG template(+) and ARITA2 template (−) (NG plasmid-supplemented and ARITA2 plasmid-unsupplemented) reaction solution (FIG. 29B) irradiated with excitation light corresponding to TAMRA, while excitation light around 495 nm and a small (fluorescence intensity: less than 20) peak (background) of fluorescence presumably derived from FAM-ARITA2-LB around 522 nm were confirmed in this reaction solution irradiated with excitation light corresponding to FAM.

Figure 29C:
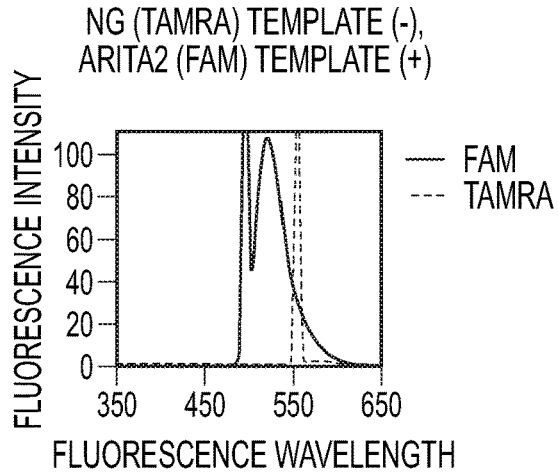

Only excitation light around 555 nm was confirmed in the ARITA2 template(+) and NG template(−) (ARITA2 plasmid-supplemented and NG plasmid-unsupplemented) reaction solution (FIG. 29C) irradiated with excitation light corresponding to TAMRA, while excitation light around 495 nm and a sufficiently large (fluorescence intensity: more than 80) peak of fluorescence presumably derived from FAM-ARITA2-LB around 522 nm were confirmed in this reaction solution irradiated with excitation light corresponding to FAM.

Figure 29D:
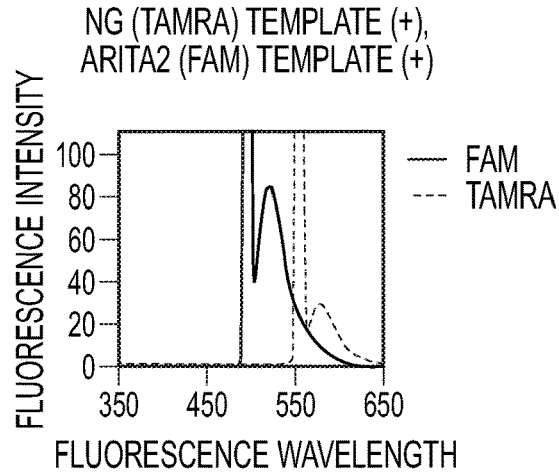

Excitation light around 555 nm and a fluorescence peak presumably derived from TAM-NG-LB around 580 nm were confirmed in the NG and ARITA template(+) (NG plasmid-supplemented and ARITA2 plasmid-supplemented) reaction solution (FIG. 29D) irradiated with excitation light corresponding to TAMRA, while excitation light around 495 nm and a sufficiently large (fluorescence intensity: more than 80) peak of fluorescence presumably derived from FAM-ARITA2-LB around 522 nm were confirmed in this reaction solution irradiated with excitation light corresponding to FAM.

TABLE 10

| Added template and amplification time | | | | | |
|---|---|---|---|---|---|
| Template | CT | − | + | − | + |
| | ARITA2 | − | − | + | + |
| | Tt | N.D.* | 12.0 | 29.0 | 11.9 |

*N.D.: Not Detect

Figure 30:
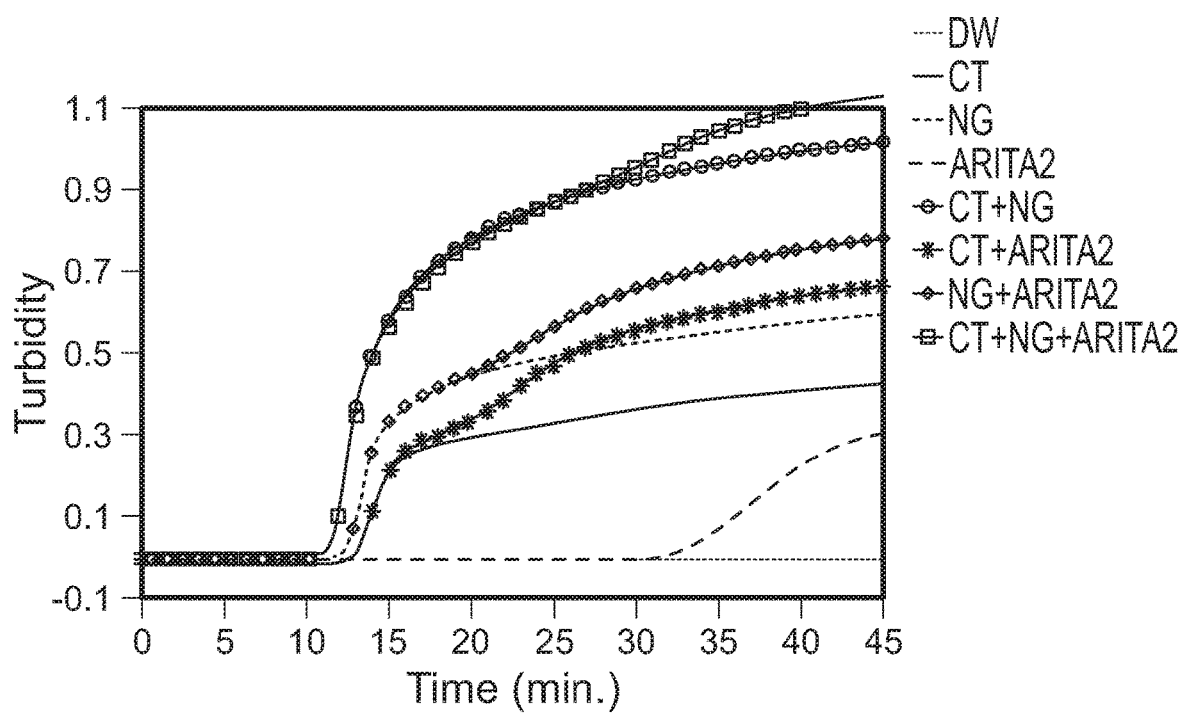
FIG. 30 shows a real-time turbidity curve from the three-item target nucleic acid amplification reaction of *Chlamydia trachomatis, Neisseria gonorrhoeae*, and an artificial nucleic acid using primers, fluorophore-labeled primers/probes, and quencher-labeled probes in Example 7.
Figure 31:
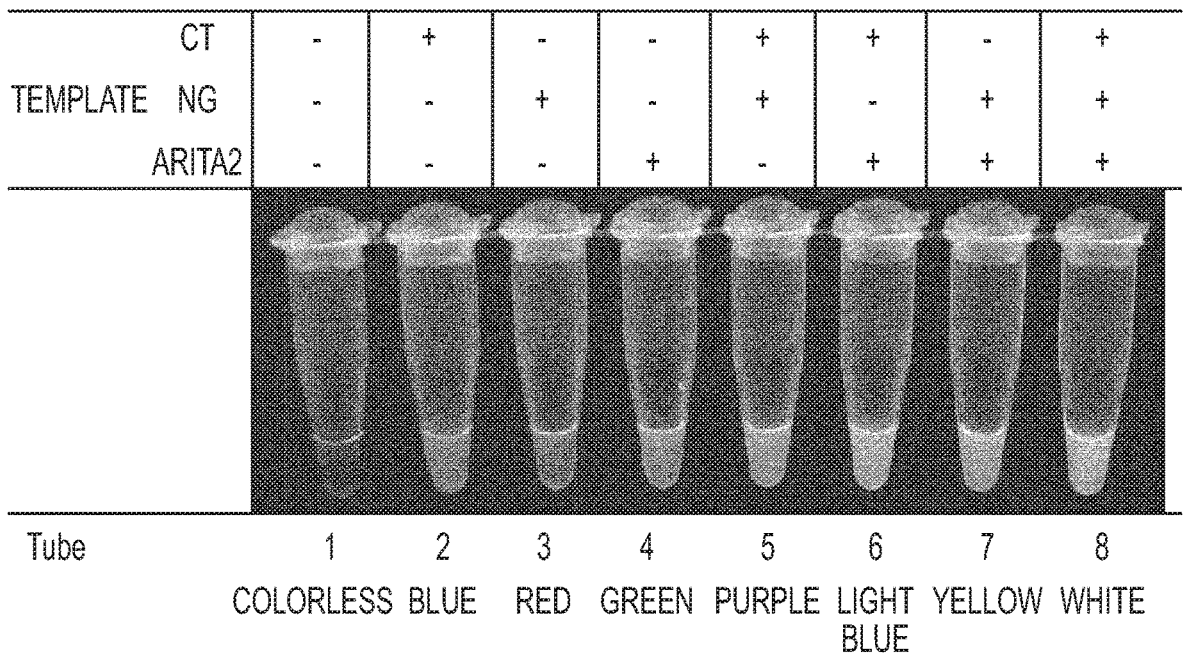
FIG. 31 shows reaction tubes irradiated with UV after the three-item target nucleic acid amplification reaction of *Chlamydia trachomatis, Neisseria gonorrhoeae*, and an artificial nucleic acid using primers, fluorophore-labeled primers/probes, and quencher-labeled probes in Example 7.

7) Results of Measuring Fluorescence Wavelength After Amplification Reaction System in Three-Item Amplification Reaction System of *Chlamydia trachomatis, Neisseria gonorrhoeae*, and Artificial Nucleic Acid In the reaction tube supplemented with DW, no nucleic acid amplification was seen (Template CT "−", NG "−", and ARITA2 "−" in Table 11 show that no Tt value was detected; and the turbidity curve of DW in FIG. 30 shows no rise in turbidity), and no fluorescence was confirmed under UV irradiation (Tube No. 1 in FIG. 31). In the reaction tube supplemented with one, two in combination, or all three of the CT plasmids, the NG plasmids, and the ARITA2 plasmids, nucleic acid amplification was seen (Template CT "+" and the other "−", Template NG "+" and the other "−", Template ARITA2 "+" and the other "−", Template CT"+" and NG"+", Template CT"+" and ARITA2"+", Template NG"+" and ARITA2"+", and Template CT"+", NG"+", and ARITA2 "+" in Table 11 show Tt values of 14.3 minutes, 13.5 minutes, 35.6 minutes, 12.3 minutes, 14.2 minutes, 13.5 minutes, and 12.4 minutes, respectively; and the turbidity curves of CT, NG, ARITA2, CT+NG CT+ARITA2, NG+ARITA2, and CT+NG+ARITA2 in FIG. 30 show a rise in turbidity), and blue fluorescence (Tube No. 2 in FIG. 31) presumably derived from Ale-CT-LB (SEQ ID NO: 40), red fluorescence (Tube No. 3 in FIG. 31) presumably derived from TAM-NG-LB (SEQ ID NO: 42), green fluorescence (Tube No. 4 in FIG. 31) presumably derived from FAM-ARITA2-LB (SEQ ID NO: 44), purple fluorescence (Tube No. 5 in FIG. 31) presumably derived from Ale-CT-LB and TAM-NG-LB, light blue fluorescence (Tube No. 6 in FIG. 31) presumably derived from Ale-CT-LB and FAM-ARITA2-LB, yellow fluorescence (Tube No. 7 in FIG. 31) presumably derived from TAM-NG-LB and FAM-ARITA2-LB, and white fluorescence (Tube No. 8 in FIG. 31) presumably derived from Ale-CT-LB, TAM-NG-LB, and FAM-ARITA2-LB were respectively confirmed under UV irradiation.

Figure 32A:
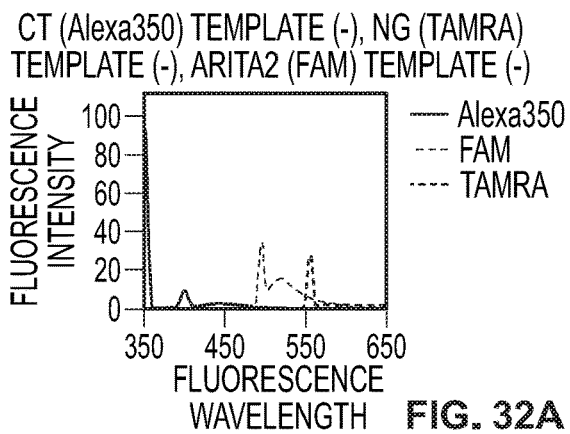
FIG. 32 shows a fluorescence wavelength after the three-item target nucleic acid amplification reaction of *Chlamydia trachomatis, Neisseria gonorrhoeae*, and an artificial nucleic acid using primers, fluorophore-labeled primers/probes, and quencher-labeled probes in Example 7.

As for the fluorescence wavelength, only excitation light around 350 nm and a Raman spectral peak of water around 398 nm were confirmed in the CT, NG, and ARITA2 template(−) (DW-supplemented) reaction solution (FIG. 32A) irradiated with excitation light corresponding to Alexa350. Only excitation light around 555 nm was confirmed in this reaction solution irradiated with excitation light corresponding to TAMRA. Excitation light around 495 nm and a small (fluorescence intensity: less than 20) peak (background) of fluorescence presumably derived from FAM-ARITA2-LB around 522 nm were confirmed in this reaction solution irradiated with excitation light corresponding to FAM.

Figure 32B:
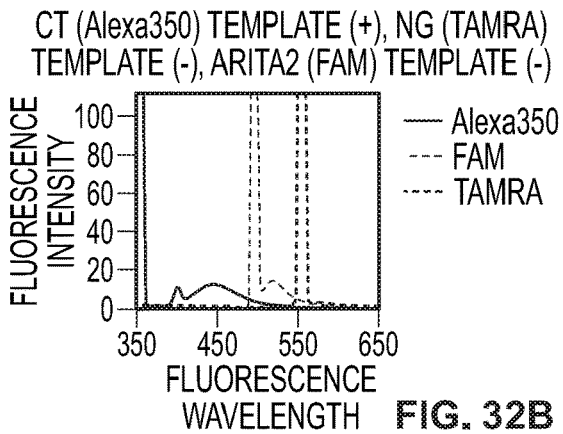

A fluorescence peak presumably derived from Ale-CT-LB was confirmed around 443 nm, in addition to excitation light around 350 nm and a Raman spectral peak of water around 398 nm, in the CT template(+) (CT plasmid-supplemented) reaction solution (FIG. 32B) irradiated with excitation light corresponding to Alexa350. Only excitation light around 555 nm was confirmed in this reaction solution irradiated with excitation light corresponding to TAMRA. Excitation light around 495 nm and a small (fluorescence intensity: less than 20) peak (background) of fluorescence presumably derived from FAM-ARITA2-LB around 522 nm were confirmed in this reaction solution irradiated with excitation light corresponding to FAM.

Figure 32C:
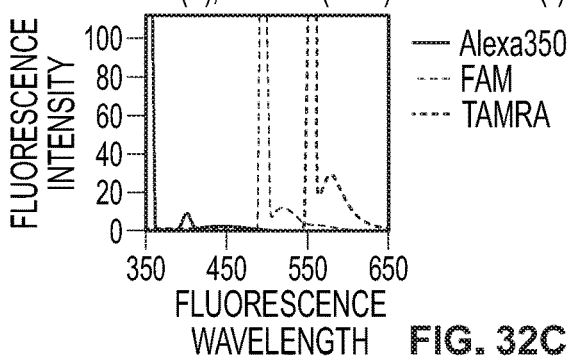

Only excitation light around 350 nm and a Raman spectral peak of water around 398 nm were confirmed in the NG template(+) (NG plasmid-supplemented) reaction solution (FIG. 32C) irradiated with excitation light corresponding to Alexa350. A fluorescence peak presumably derived from TAM-NG-LB was confirmed around 580 nm, in addition to excitation light around 555 nm, in this reaction solution irradiated with excitation light corresponding to TAMRA. Excitation light around 495 nm and a small (fluorescence intensity: less than 20) peak (background) of fluorescence presumably derived from FAM-ARITA2-LB around 522 nm were confirmed in this reaction solution irradiated with excitation light corresponding to FAM.

Figure 32D:
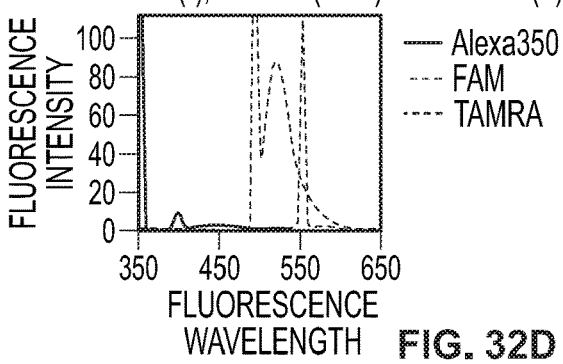

Only excitation light around 350 nm and a Raman spectral peak of water around 398 nm were confirmed in the ARITA2 template(+) (ARITA2 plasmid-supplemented) reaction solution (FIG. 32D) irradiated with excitation light corresponding to Alexa350. Only excitation light around 555 nm was confirmed in this reaction solution irradiated with excitation light corresponding to TAMRA. Excitation light around 495 nm and a sufficiently large (fluorescence intensity: more than 80) peak (background) of fluorescence presumably derived from FAM-ARITA2-LB around 522 nm were confirmed in this reaction solution irradiated with excitation light corresponding to FAM.

Figure 32E:
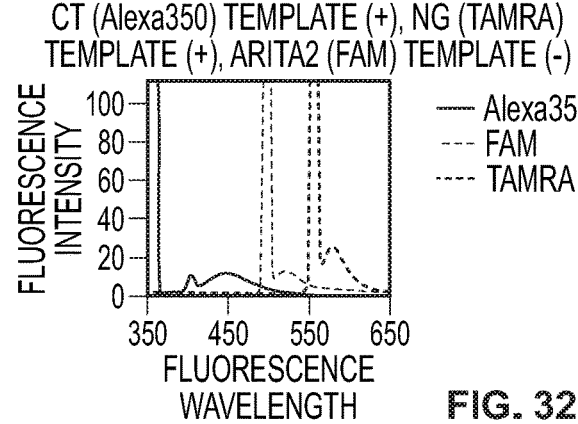

A fluorescence peak presumably derived from Ale-CT-LB was confirmed around 443 nm, in addition to excitation light for Alexa350 around 350 nm and a Raman spectral peak of water around 398 nm, in the CT and NG template(+) (CT plasmid-supplemented and NG plasmid-supplemented) reaction solution (FIG. 32E) irradiated with excitation light corresponding to Alexa350. Excitation light around 555 nm and a fluorescence peak presumably derived from TAM-NG-LB around 580 nm were confirmed in this reaction solution irradiated with excitation light corresponding to TAMRA. By contrast, only excitation light around 495 nm and a small (fluorescence intensity: less than 20) peak (background) of fluorescence presumably derived from FAM-ARITA2-LB around 522 nm were confirmed in this reaction solution irradiated with excitation light corresponding to FAM.

Figure 32F:
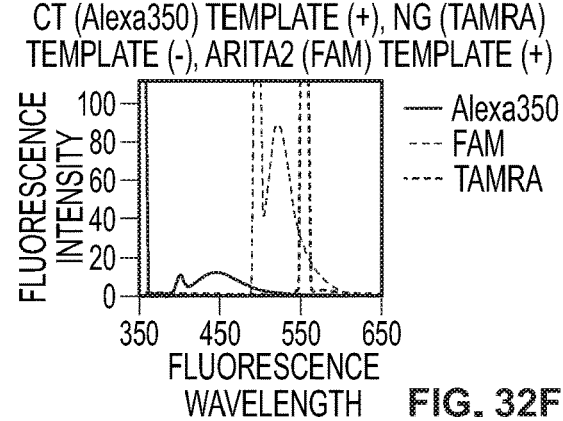

A fluorescence peak presumably derived from Ale-CT-LB was confirmed around 443 nm, in addition to excitation light around 350 nm and a Raman spectral peak of water around 398 nm, in the CT and ARITA2 template(+) (CT plasmid-supplemented and ARITA2 plasmid-supplemented) reaction solution (FIG. 32F) irradiated with excitation light corresponding to Alexa350. Only excitation light around 555 nm was confirmed in this reaction solution irradiated with, excitation light corresponding to TAMRA. Excitation light around 495 nm and a sufficiently large (fluorescence intensity: more than 80) peak of fluorescence presumably derived from FAM-ARITA2-LB around 522 nm were confirmed in this reaction solution irradiated with excitation light corresponding to FAM.

Figure 32G:
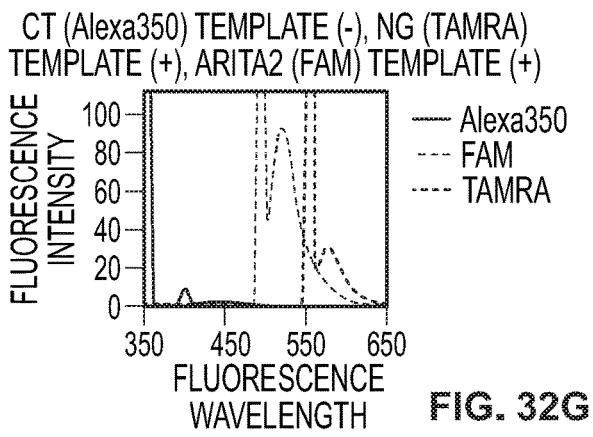

Only excitation light around 350 nm and a Raman spectral peak of water around 398 nm were confirmed in the NG and ARITA2 template(+) (NG plasmid-supplemented and ARITA2 plasmid-supplemented) reaction solution (FIG. 32G) irradiated with excitation light corresponding to Alexa350. Excitation light around 555 nm and a fluorescence peak presumably derived from TAM-NG-LB around 580 nm were confirmed in this reaction solution irradiated with excitation light corresponding to TAMRA. Excitation light around 495 nm and a sufficiently large (fluorescence intensity: more than 80) peak of fluorescence presumably derived from FAM-ARITA2-LB around 522 nm were confirmed in this reaction solution irradiated with excitation light corresponding to FAM.

Figure 32H:
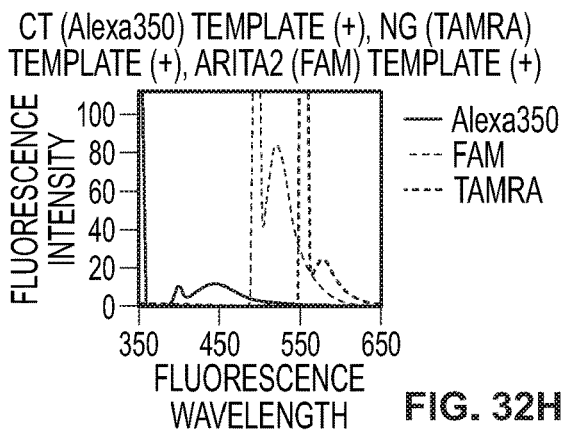

A fluorescence peak presumably derived from Ale-CT-LB was confirmed around 443 nm, in addition to excitation light for Alexa350 around 350 nm and a Raman spectral peak of water around 398 nm, in the CT, NG and ARITA2 template (+) (CT plasmid-, NG plasmid-, and ARITA2 plasmid-supplemented) reaction solution (FIG. 32H) irradiated with excitation light corresponding to Alexa350. Excitation light around 555 nm and a fluorescence peak presumably derived from TAM-NG-LB around 580 nm were confirmed in this reaction solution irradiated with excitation light corresponding to TAMRA. Excitation light around 495 nm and a sufficiently large (fluorescence intensity: more than 80) peak of fluorescence presumably derived from FAM-ARITA2-LB around 522 nm were confirmed in this reaction solution irradiated with excitation light corresponding to FAM.

TABLE 11

| | | | | | | | | | |
|---|---|---|---|---|---|---|---|---|---|
| | Added template and amplification time | | | | | | | | |
| Template | CT | — | + | — | — | + | + | — | + |
| | NG | — | — | + | — | + | — | + | + |
| | ARITA2 | — | — | — | + | — | + | + | + |
| | Tt | N.D.* | 14.3 | 13.5 | 35.6 | 12.3 | 14.2 | 13.5 | 12.4 |

*N.D.: Not Detect

The present invention is directed to the detection of fluorescence derived from one fluorescent label for use in detection on an item basis for nucleic acid amplification from one template in a single-item or multiple-item amplification reaction system and to the detection of fluorescence derived from plural fluorescent labels for use in detection of respective items for nucleic acid amplification from plural templates in a multiple-item amplification reaction system. Visual detection requires fluorescence to have a color within a range recognizable by trichromatism in humans. For example, blue, red, and green fluorescent labels as shown in Examples are used as primary colors, and color tones expressed by using additive mixing are 7 colors: purple, yellow, light blue, and white in addition to the above 3 primary colors. Thus, the upper limit is a total of 8 colors further including the absence of fluorescence (colorless, i.e., no fluorescence). On the other hand, detection using a fluorometer can detect more items simultaneously and can also quantify the items on the basis of emission intensity, because fluorescent labels of types recognizable by the apparatus can be used.

Example 7 shows that according to the present invention, fluorescence can be measured using a fluorescence detector in order to detect nucleic acid amplification through isothermal amplification reaction, regardless of single or multiple items.

INDUSTRIAL APPLICABILITY

The present invention can provide a method for detecting a target nucleic acid more conveniently and inexpensively than conventional techniques. Also, the method of the present invention applied to a microarray can detect gene expression without labeling target nucleic acids. Furthermore, the method of the present invention combined with a conventional nucleic acid amplification technique can also detect multiple target nucleic acids at once merely by one-step addition of reagents. In addition, the method of the present invention enables such detection to be visually achieved without the use of special equipment. Thus, the present invention can serve as a very effective tool not only in specific laboratories but in the identification of infecting bacteria or viruses in hospitals, the confirmation of drug sensitivity, the prediction of therapeutic effects by the detection of single nucleotide polymorphisms, safety check in the production and distribution of foods, etc.

The invention claimed is:

1. A method for detecting one or more target nucleic acids present in a sample, comprising the following steps:
   (1) adding, to the sample,
      (A) a fluorophore-labeled primer or probe, wherein the fluorophore-labeled primer or probe is a fluorophore-labeled oligonucleotide having complementarity to a target nucleic acid, and
      a quencher-labeled probe, wherein the quencher-labeled probe is a quencher-labeled oligonucleotide having complementarity to the fluorophore-labeled primer or probe and having a melting temperature (Tm) lower than that of the fluorophore-labeled primer or probe; or
      (B) fluorophore-labeled primers or probes that are oligonucleotides labeled with fluorophores differing in emission wavelength, respectively, and that have complementarity to different target nucleic acids, respectively, and
      quencher-labeled probes that are oligonucleotides that have complementarity to the fluorophore-labeled primers or probes, respectively, that are labeled with quenchers that correspond to the fluorophores of said complementary primers or probes, respectively, and that have a melting temperature (Tm) lower than that of the complementary fluorophore-labeled primers or probes, respectively;
   (2) incubating the sample at a temperature equal to or lower than the melting temperature (Tm) of the fluorophore-labeled primer(s) or probe(s) and higher than the melting temperature (Tm) of the quencher-labeled probe(s), wherein the target nucleic acid(s) are amplified during the incubation step by smart amplification process version 2 (SMAP2) or loop-mediated isothermal amplification (LAMP) at a constant temperature, wherein the fluorophore-labeled primer(s) or probe(s) hybridize to a loop region;
   (3) incubating the sample at room temperature; and
   (4) measuring fluorescence of the fluorophore-labeled primer(s) or probe(s) bound with the target nucleic acid at room temperature.

2. The detection method according to claim 1, wherein the oligonucleotide(s) of the quencher-labeled probe(s) have a base length shorter than that of the oligonucleotide(s) of the complementary fluorophore-labeled primer(s) or probe(s).

3. The detection method according to claim 1, wherein the oligonucleotide of the quencher-labeled probe(s) comprise a modified base.

4. The detection method according to claim 1, wherein the fluorophore-labeled primer(s) or probe(s) are immobilized on a solid-phase surface for use.

5. The method according to claim 1, wherein the measurement of the fluorescence in the step (4) is visual determination.

6. The method according to claim 1, wherein the measurement of the fluorescence in the step (4) is determination using a fluorescence detector.

7. The detection method according to claim 2, wherein the fluorophore-labeled primer(s) or probe(s) are immobilized on a solid-phase surface for use.

8. The detection method according to claim 3, wherein the fluorophore-labeled primer(s) or probe(s) are immobilized on a solid-phase surface for use.

9. The detection method according to claim 2, wherein the measurement of the fluorescence in the step (4) is visual determination.

10. The detection method according to claim 3, wherein the measurement of the fluorescence in the step (4) is visual determination.

11. The detection method according to claim 2, wherein the measurement of the fluorescence in the step (4) is determination using a fluorescence detector.

12. The detection method according to claim 3, wherein the measurement of the fluorescence in the step (4) is determination using a fluorescence detector.

* * * * *

SEQUENCE LISTING

```
<160> NUMBER OF SEQ ID NOS: 45

<210> SEQ ID NO 1
<211> LENGTH: 39
<212> TYPE: DNA
<213> ORGANISM: Artificial Sequence
<220> FEATURE:
<223> OTHER INFORMATION: CT-FIP: Synthesized Primer/Probe

<400> SEQUENCE: 1
caagcaggac tacaagctgc agcgtttgta ctccgtcac                              39

<210> SEQ ID NO 2
<211> LENGTH: 37
<212> TYPE: DNA
<213> ORGANISM: Artificial Sequence
<220> FEATURE:
<223> OTHER INFORMATION: CT-BIP: Synthesized Primer/Probe

<400> SEQUENCE: 2
gcgggcgatt tgccttaact cggtcaacga agaggtt                                37

<210> SEQ ID NO 3
<211> LENGTH: 18
<212> TYPE: DNA
<213> ORGANISM: Artificial Sequence
<220> FEATURE:
<223> OTHER INFORMATION: CT-F3: Synthesized Primer/Probe

<400> SEQUENCE: 3
atgtcggagt ctgagcac                                                     18

<210> SEQ ID NO 4
<211> LENGTH: 22
<212> TYPE: DNA
<213> ORGANISM: Artificial Sequence
```

```
<220> FEATURE:
<223> OTHER INFORMATION: CT-B3: Synthesized Primer/Probe

<400> SEQUENCE: 4
cctcagaagt ttatgcactt tc                                        22

<210> SEQ ID NO 5
<211> LENGTH: 17
<212> TYPE: DNA
<213> ORGANISM: Artificial Sequence
<220> FEATURE:
<223> OTHER INFORMATION: CT-LF: Synthesized Primer/Probe

<400> SEQUENCE: 5
aagataaccc cgcacgt                                              17

<210> SEQ ID NO 6
<211> LENGTH: 19
<212> TYPE: DNA
<213> ORGANISM: Artificial Sequence
<220> FEATURE:
<223> OTHER INFORMATION: CT-LB: Synthesized Primer/Probe

<400> SEQUENCE: 6
ggagcgagtt acgaagaca                                            19

<210> SEQ ID NO 7
<211> LENGTH: 19
<212> TYPE: DNA
<213> ORGANISM: Artificial Sequence
<220> FEATURE:
<223> OTHER INFORMATION: FAM-CT-LB: Synthesized Primer/Probe

<400> SEQUENCE: 7
ggagcgagtt acgaagaca                                            19

<210> SEQ ID NO 8
<211> LENGTH: 19
<212> TYPE: DNA
<213> ORGANISM: Artificial Sequence
<220> FEATURE:
<223> OTHER INFORMATION: CT-LBc-Q1-0: Synthesized Primer/Probe

<400> SEQUENCE: 8
tgtcttcgta actcgctcc                                            19

<210> SEQ ID NO 9
<211> LENGTH: 16
<212> TYPE: DNA
<213> ORGANISM: Artificial Sequence
<220> FEATURE:
<223> OTHER INFORMATION: CT-LBc-Q1-3: Synthesized Primer/Probe

<400> SEQUENCE: 9
cttcgtaact cgctcc                                               16

<210> SEQ ID NO 10
<211> LENGTH: 14
<212> TYPE: DNA
<213> ORGANISM: Artificial Sequence
<220> FEATURE:
<223> OTHER INFORMATION: CT-LBc-Q1-5: Synthesized Primer/Probe

<400> SEQUENCE: 10
tcgtaactcg ctcc                                                 14
```

```
<210> SEQ ID NO 11
<211> LENGTH: 13
<212> TYPE: DNA
<213> ORGANISM: Artificial Sequence
<220> FEATURE:
<223> OTHER INFORMATION: CT-LBc-Q1-6: Synthesized Primer/Probe

<400> SEQUENCE: 11
cgtaactcgc tcc                                                          13

<210> SEQ ID NO 12
<211> LENGTH: 12
<212> TYPE: DNA
<213> ORGANISM: Artificial Sequence
<220> FEATURE:
<223> OTHER INFORMATION: CT-LBc-Q1-7: Synthesized Primer/Probe

<400> SEQUENCE: 12
gtaactcgct cc                                                           12

<210> SEQ ID NO 13
<211> LENGTH: 10
<212> TYPE: DNA
<213> ORGANISM: Artificial Sequence
<220> FEATURE:
<223> OTHER INFORMATION: CT-LBc-Q1-9: Synthesized Primer/Probe

<400> SEQUENCE: 13
aactcgctcc                                                              10

<210> SEQ ID NO 14
<211> LENGTH: 9
<212> TYPE: DNA
<213> ORGANISM: Artificial Sequence
<220> FEATURE:
<223> OTHER INFORMATION: CT-LBc-Q1-10: Synthesized Primer/Probe

<400> SEQUENCE: 14 actcgctcc                                                                9

<210> SEQ ID NO 15
<211> LENGTH: 17
<212> TYPE: DNA
<213> ORGANISM: Artificial Sequence
<220> FEATURE:
<223> OTHER INFORMATION: TAM-CT-LF: Synthesized Primer/Probe

<400> SEQUENCE: 15
aagataaccc cgcacgt                                                      17

<210> SEQ ID NO 16
<211> LENGTH: 17
<212> TYPE: DNA
<213> ORGANISM: Artificial Sequence
<220> FEATURE:
<223> OTHER INFORMATION: CT-LFc-Q2: Synthesized Primer/Probe

<400> SEQUENCE: 16
acgtgcgggg ttatctt                                                      17

<210> SEQ ID NO 17
<211> LENGTH: 36
<212> TYPE: DNA
<213> ORGANISM: Artificial Sequence
<220> FEATURE:
<223> OTHER INFORMATION: NG-FIP: Synthesized Primer/Probe
```

<400> SEQUENCE: 17
cgtggctcaa cacatgaccc aagcgtccgg tcggca                                    36

<210> SEQ ID NO 18
<211> LENGTH: 45
<212> TYPE: DNA
<213> ORGANISM: Artificial Sequence
<220> FEATURE:
<223> OTHER INFORMATION: NG-BIP: Synthesized Primer/Probe

<400> SEQUENCE: 18
acggagaaag tttacaaccg gacacaaaac aggctcatat ccagc                          45

<210> SEQ ID NO 19
<211> LENGTH: 18
<212> TYPE: DNA
<213> ORGANISM: Artificial Sequence
<220> FEATURE:
<223> OTHER INFORMATION: NG-F3: Synthesized Primer/Probe

<400> SEQUENCE: 19
gcggttatct ctgcatcg                                                        18

<210> SEQ ID NO 20
<211> LENGTH: 17
<212> TYPE: DNA
<213> ORGANISM: Artificial Sequence
<220> FEATURE:
<223> OTHER INFORMATION: NG-B3: Synthesized Primer/Probe

<400> SEQUENCE: 20
ggtgtcgtag cggaaac                                                         17

<210> SEQ ID NO 21
<211> LENGTH: 428
<212> TYPE: DNA
<213> ORGANISM: Chlamydia trachomatis

<400> SEQUENCE: 21
ctcgagaaga tttatcgtac gcaaatatca tctttgcggt tgcgtgtcct gtgaccttca          60
ttatgtcgga gtctgagcac cctaggcgtt tgtactccgt cacagcggtt gctcgaagca         120 cgtgcgggt tatcttaaaa gggattgcag cttgtagtcc tgcttgagag aacgtgcggg          180
cgatttgcct taaccccacc attttttccgg agcgagttac gaagacaaaa cctcttcgtt        240
gaccgatgta ctcttgtaga aagtgcataa acttctgagg ataagttata ataatcctct         300
tttctgtctg acggttctta agctgggaga agaaatggt agcttgttgg aaacaaatct          360
gactaatctc caagcttaag acttcagagg agcgtttacc tccttggagc attgtctggg        420
cgatcaac                                                                 428

<210> SEQ ID NO 22
<211> LENGTH: 22
<212> TYPE: DNA
<213> ORGANISM: Artificial Sequence
<220> FEATURE:
<223> OTHER INFORMATION: NG-LF: Synthesized Primer/Probe

<400> SEQUENCE: 22
cgggaaaaat acaatatcgc cc                                                   22

-continued

```
<210> SEQ ID NO 23
<211> LENGTH: 22
<212> TYPE: DNA
<213> ORGANISM: Artificial Sequence
<220> FEATURE:
<223> OTHER INFORMATION: FAM-NG-LB: Synthesized Primer/Probe

<400> SEQUENCE: 23
cgacaaaacg gcacatttat gg                                              22

<210> SEQ ID NO 24
<211> LENGTH: 22
<212> TYPE: DNA
<213> ORGANISM: Artificial Sequence
<220> FEATURE:
<223> OTHER INFORMATION: NG-LBc-Q1: Synthesized Primer/Probe

<400> SEQUENCE: 24
ccataaatgt gccgttttgt cg                                              22

<210> SEQ ID NO 25
<211> LENGTH: 34
<212> TYPE: DNA
<213> ORGANISM: Artificial Sequence
<220> FEATURE:
<223> OTHER INFORMATION: ARITA2-FIP: Synthesized Primer/Probe

<400> SEQUENCE: 25
cgcttggata gtcggatgca agggtcaatg gtac                                 34

<210> SEQ ID NO 26
<211> LENGTH: 33
<212> TYPE: DNA
<213> ORGANISM: Artificial Sequence
<220> FEATURE:
<223> OTHER INFORMATION: ARITA2-BIP: Synthesized Primer/Probe

<400> SEQUENCE: 26
acggtgtatg cttcggtgtg cgaacctatc agc                                  33

<210> SEQ ID NO 27
<211> LENGTH: 18
<212> TYPE: DNA
<213> ORGANISM: Artificial Sequence
<220> FEATURE:
<223> OTHER INFORMATION: ARITA2-F3: Synthesized Primer/Probe

<400> SEQUENCE: 27
ggacaatcga agccagaa                                                   18

<210> SEQ ID NO 28
<211> LENGTH: 18
<212> TYPE: DNA
<213> ORGANISM: Artificial Sequence
<220> FEATURE:
<223> OTHER INFORMATION: ARITA2-B3: Synthesized Primer/Probe

<400> SEQUENCE: 28
atcacggatc gtatgtgg                                                   18

<210> SEQ ID NO 29
<211> LENGTH: 18
<212> TYPE: DNA
<213> ORGANISM: Artificial Sequence
<220> FEATURE:
<223> OTHER INFORMATION: ARITA2-LF5: Synthesized Primer/Probe
```

<400> SEQUENCE: 29
gctagctaag tgccatcc                                                    18

<210> SEQ ID NO 30
<211> LENGTH: 18
<212> TYPE: DNA
<213> ORGANISM: Artificial Sequence
<220> FEATURE:
<223> OTHER INFORMATION: Ale-ARITA2-LB: Synthesized Primer/Probe

<400> SEQUENCE: 30
aacgatcgca ctaagcat                                                    18

<210> SEQ ID NO 31
<211> LENGTH: 18
<212> TYPE: DNA
<213> ORGANISM: Artificial Sequence
<220> FEATURE:
<223> OTHER INFORMATION: ARITA2-LBc-Q0: Synthesized Primer/Probe

<400> SEQUENCE: 31
atgcttagtg cgatcgtt                                                    18

<210> SEQ ID NO 32
<211> LENGTH: 451
<212> TYPE: DNA
<213> ORGANISM: Neisseria gonorrhoeae

<400> SEQUENCE: 32
gacattctgg acaaactggt cgatctcgcc caattgacgg gcagtgcgga tgtgcagtgc      60
cttttgggcg gacaatggtc ggtacggcat gaaaccttgc aatgcgaagg gctggtacac     120
attgttacgg cgggcagcgg ttatctctgc atcgacggcg aaacttcccc gcgtccggtc     180
ggcacgggcg atattgtatt tttcccgcgc ggcttgggtc atgtgttgag ccacgacgga     240
aaatacggag aaagtttaca accggacata cgacaaaacg gcacatttat ggtcaaacag     300
tgcggcaacg gctggatat gagcctgttt tgcgcccgtt ccgctacga cacccacgcc       360
gatttgatga acgggctgcc ggaaaccgtt tttctgaaca ttgcccatcc aagtttgcag     420
tatgtggttt caatgctgca actggaaagc g                                    451

<210> SEQ ID NO 33
<211> LENGTH: 569
<212> TYPE: DNA
<213> ORGANISM: Artificial Sequence
<220> FEATURE:
<223> OTHER INFORMATION: Synthesized DNA

<400> SEQUENCE: 33
gggtcaatcg tagggacaat cgaagccaga atgcaagggt caatggtacg cagaatggat      60
ggcacttagc tagccagtta ggatccgact atccaagcgt gtatcgtacg gtgtatgctt     120
cggagtaacg atcgcactaa gcatggctca atcctaggct gataggttcg cacatagcat     180
gccacatacg atccgtgatt gctagcgtga ttcgtaccga gaactcacgc cttatgactg     240
cccttatgtc accgcttatg tctcccgata tcacacccgt tatctcagcc ctaatctctg     300
cggtttagtc tggccttaat ccatgcctca tagctaccct cataccatcg ctcatacctt     360
ccgacattgc atccgtcatt ccaacccctga ttcctacgg ctaacctagc ctctatccta     420
cccagttagg ttgcctctta gcatccctgt tacgtacgct cttaccatgc gtcttacctt     480

```
ggcactatcg atgggagtat ggtagcgagt atggaacgga ctaacgtagg cagtaagcta    540
gggtgtaagg ttgggactaa ggatgccag                                      569
```

<210> SEQ ID NO 34
<211> LENGTH: 34
<212> TYPE: DNA
<213> ORGANISM: Artificial Sequence
<220> FEATURE:
<223> OTHER INFORMATION: CT-FP: Synthesized Primer/Probe

<400> SEQUENCE: 34

```
tttatatata tataaagcgt ttgtactccg tcac                                 34
```

<210> SEQ ID NO 35
<211> LENGTH: 37
<212> TYPE: DNA
<213> ORGANISM: Artificial Sequence
<220> FEATURE:
<223> OTHER INFORMATION: CT-TP: Synthesized Primer/Probe

<400> SEQUENCE: 35

```
gcgggcgatt tgccttaact cggtcaacga agaggtt                              37
```

<210> SEQ ID NO 36
<211> LENGTH: 22
<212> TYPE: DNA
<213> ORGANISM: Artificial Sequence
<220> FEATURE:
<223> OTHER INFORMATION: CT-OP1: Synthesized Primer/Probe

<400> SEQUENCE: 36

```
cctcagaagt ttatgcactt tc                                              22
```

<210> SEQ ID NO 37
<211> LENGTH: 18
<212> TYPE: DNA
<213> ORGANISM: Artificial Sequence
<220> FEATURE:
<223> OTHER INFORMATION: CT-OP2: Synthesized Primer/Probe

<400> SEQUENCE: 37

```
atgtcggagt ctgagcac                                                   18
```

<210> SEQ ID NO 38
<211> LENGTH: 19
<212> TYPE: DNA
<213> ORGANISM: Artificial Sequence
<220> FEATURE:
<223> OTHER INFORMATION: Ale-CT-BP: Synthesized Primer/Probe

<400> SEQUENCE: 38

```
ggagcgagtt acgaagaca                                                  19
```

<210> SEQ ID NO 39
<211> LENGTH: 10
<212> TYPE: DNA
<213> ORGANISM: Artificial Sequence
<220> FEATURE:
<223> OTHER INFORMATION: CT-BPc-Q0: Synthesized Primer/Probe

<400> SEQUENCE: 39

```
aactcgctcc                                                            10
```

```
<210> SEQ ID NO 40
<211> LENGTH: 19
<212> TYPE: DNA
<213> ORGANISM: Artificial Sequence
<220> FEATURE:
<223> OTHER INFORMATION: Ale-CT-LB: Synthesized Primer/Probe

<400> SEQUENCE: 40
ggagcgagtt acgaagaca                                                    19

<210> SEQ ID NO 41
<211> LENGTH: 10
<212> TYPE: DNA
<213> ORGANISM: Artificial Sequence
<220> FEATURE:
<223> OTHER INFORMATION: CT-LBc-Q0: Synthesized Primer/Probe

<400> SEQUENCE: 41
aactcgctcc                                                              10

<210> SEQ ID NO 42
<211> LENGTH: 22
<212> TYPE: DNA
<213> ORGANISM: Artificial Sequence
<220> FEATURE:
<223> OTHER INFORMATION: TAM-NG-LB: Synthesized Primer/Probe

<400> SEQUENCE: 42
cgacaaaacg gcacatttat gg                                                22

<210> SEQ ID NO 43
<211> LENGTH: 10
<212> TYPE: DNA
<213> ORGANISM: Artificial Sequence
<220> FEATURE:
<223> OTHER INFORMATION: NG-LBc-Q2: Synthesized Primer/Probe

<400> SEQUENCE: 43
cgttttgtcg                                                              10

<210> SEQ ID NO 44
<211> LENGTH: 18
<212> TYPE: DNA
<213> ORGANISM: Artificial Sequence
<220> FEATURE:
<223> OTHER INFORMATION: FAM-ARITA2-LB: Synthesized Primer/Probe

<400> SEQUENCE: 44
aacgatcgca ctaagcat                                                     18

<210> SEQ ID NO 45
<211> LENGTH: 18
<212> TYPE: DNA
<213> ORGANISM: Artificial Sequence
<220> FEATURE:
<223> OTHER INFORMATION: ARITA2-LBc-Q1: Synthesized Primer/Probe

<400> SEQUENCE: 45
atgcttagtg cgatcgtt                                                     18
```